(12) United States Patent
Cui et al.

(10) Patent No.: US 9,924,883 B2
(45) Date of Patent: Mar. 27, 2018

(54) BIOMIMETIC COATING FOR NEURAL IMPLANTS

(71) Applicants: Xinyan T. Cui, Wexford, PA (US);
Carl F. Lagenaur, Pittsburgh, PA (US);
Erdrin Azemi, Sunnyvale, CA (US);
Noah R. Snyder, Glenshaw, PA (US)

(72) Inventors: Xinyan T. Cui, Wexford, PA (US);
Carl F. Lagenaur, Pittsburgh, PA (US);
Erdrin Azemi, Sunnyvale, CA (US);
Noah R. Snyder, Glenshaw, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 770 days.

(21) Appl. No.: 14/317,271

(22) Filed: Jun. 27, 2014

(65) Prior Publication Data
US 2015/0005607 A1    Jan. 1, 2015

Related U.S. Application Data

(60) Provisional application No. 61/841,223, filed on Jun. 28, 2013.

(51) Int. Cl.
*A61B 5/04* (2006.01)
*A61N 1/05* (2006.01)
*A61B 5/00* (2006.01)

(52) U.S. Cl.
CPC ........ *A61B 5/04001* (2013.01); *A61N 1/0534* (2013.01); *A61N 1/0551* (2013.01);
(Continued)

(58) Field of Classification Search
CPC .............. A61N 5/04001; A61N 1/0529; A61N 1/0531; A61N 1/0534; A61N 1/0536;
(Continued)

(56) References Cited

U.S. PATENT DOCUMENTS 8,355,802 B2    1/2013    Keitel et al.
8,676,343 B2    3/2014    Bloemer et al.
(Continued)

FOREIGN PATENT DOCUMENTS

WO    WO 2005/114720    12/2005
WO    WO 2013/018088    2/2013

OTHER PUBLICATIONS

Kenwrick, S., Watkins, A., De Angelis, E. (2000) Neural Cell Recognition Molecule L1: Relating Biological Complexity to Human Disease Mutations. Hum Mol Gen, 2000. vol. 9, No. 6, pp. 879-886.*

(Continued)

*Primary Examiner* — Lee S Cohen
*Assistant Examiner* — Eunhwa Kim
(74) *Attorney, Agent, or Firm* — Klarquist Sparkman, LLP

(57) ABSTRACT

Disclosed herein are neural probes comprising an L1 polypeptide functional fragment thereof on the exterior surface of the probe, devices including such electrodes, and methods of their use. The disclosed embodiments are useful, for example, for in methods of recording and/or stimulating neural signals in a subject.

10 Claims, 26 Drawing Sheets
(19 of 26 Drawing Sheet(s) Filed in Color)

(52) U.S. Cl.
CPC .............. *A61B 5/688* (2013.01); *A61B 5/6868* (2013.01); *A61B 2562/125* (2013.01); *A61N 1/0526* (2013.01); *A61N 1/0529* (2013.01)

(58) Field of Classification Search
CPC ................ A61B 1/0534; A61B 1/0551; A61B 2562/125; A61B 5/6868; A61B 5/688; A61B 5/04001
See application file for complete search history.

(56) References Cited

U.S. PATENT DOCUMENTS

| | | | |
|---|---|---|---|
| 2006/0225274 A1* | 10/2006 | Greenberg | ............ A61N 1/0551 29/846 |
| 2009/0280153 A1 | 11/2009 | Hunter et al. | |
| 2011/0301665 A1* | 12/2011 | Mercanzini | .......... A61N 1/0531 607/45 |

OTHER PUBLICATIONS

Araki, et al. "BIT/SHPS-1 enhances brain-derived neurotrophic factor-promoted neuronal survival in cultured cerebral cortical neurons." *Journal of Neurochemistry* 75.4 (2000): 1502-1510.
Azemi, et al. "The surface immobilization of the neural adhesion molecule L1 on neural probes and its effect on neuronal density and gliosis at the probe/tissue interlace." *Biomaterials* 32.3 (2011): 681-692.
Azemi, et al. "Surface immobilization of neural adhesion molecule L1 for improving the biocompatibility of chronic neural probes: In vitro characterization." *Acta Biomaterialia* 4.5 (2008): 1208-1217.
Babcock, et al. "Chemokine expression by glial cells directs leukocytes to sites of axonal injury in the CNS." *The Journal of Neuroscience* 23.21 (2003): 7922-7930.
Bennett, et al. "A distinct subgroup of small DRG cells express GDNF receptor components and GDNF is protective for these neurons after nerve injury." *The Journal of Neuroscience* 18.8 (1998): 3059-3072.
Bhatia, et al. "Use of thiol-terminal silanes and heterobifunctional crosslinkers for immobilization of antibodies on silica and surfaces." *Analytical Biochemistry* 178.2 (1989):408-413.
Blackrock Microsystems microelectrode arrays product description, available at http://www.blackrockmicro.com/content.aspx?id=11, last accessed May 11, 2015.
Brisson, et al. "Function of oxidative cross-linking of cell wall structural proteins in plant disease resistance." *The Plant Cell Online* 6.12 (1994): 1703-1712.
Chang, et al. "Cell and protein compatibility of parylene-C surfaces." *Langmuir* 23.23 (2007): 11718-11725.
Chestek, et al. "Long-term stability of neural prosthetic control signals from silicon cortical arrays in rhesus macaque motor cortex." *Journal of Neural Engineering* 8.4 (2011): 045005.
Cheung. "Implantable microscale neural interfaces." *Biomedical Microdevices* 9.6 (2007): 923-938.
Choquet, et al. "Extracellular matrix rigidity causes strengthening of integrin-cytoskeleton linkages." *Cell* 88.1 (1997): 39-48.
Cui, et al. "In vivo studies of polypyrrole/peptide coated neural probes." *Biomaterials* 24.5 (2003): 777-787.
Dierendonck, et al. "Single-step formation of degradable intracellular biomolecule microreactors." *Acs Nano* 5.9 (2011): 6886-6893.
Edell, et al. "Factors influencing the biocompatibility of insertable silicon microshafts in cerebral cortex." *Biomedical Engineering, IEEE Transactions on* 39.6 (1992): 635-643.
Figge, et al. "Neurite outgrowth triggered by the cell adhesion molecule L1 requires activation and inactivation of the cytoskeletal protein cofilin."*Molecular and Cellular Neuroscience* 49.2 (2012): 196-204.
Fraser, el al. "Recording from the same neurons chronically in motor cortex," *Journal of Neurophysiology* 107.7 (2012): 1970-1978.

GenBank Accession No. AAI43497 (CHL1) as present in the database on Jun. 20, 2013.
GenBank Accession No. BC047244.1 (NCAM1) as present in the database on Jun. 20, 2013.
GenBank Accession No. NP_000416.1 (L1) as present in the database on Jun. 20, 2013.
GenBank Accession No. O94856 (Neurofascin) as present in the database on Jun. 20, 2013.
Golda, et al. "Oxygen plasma functionalization of parylene C coating for implants surface: Nanotopography and active sites for drug anchoring." *Materials Science and Engineering: C* 33.7 (2013): 4221-4227.
Grill, et al. "Implanted neural interfaces: biochallenges and engineered solutions." *Annual Review of Biomedical Engineering* 11 (2009): 1-24.
Hanani. "Satellite glial cells in sensory ganglia: from form to function." *Brain Research Reviews* 48.3 (2005): 457-476.
Haspel, et al. "Disulfide-mediated dimerization of L1 Ig domains." *Journal of Neuroscience Research* 66.3 (2001): 347-355.
Hu, el al. "Immune cell involvement in dorsal root ganglia and spinal cord after chronic constriction or transection of the rat sciatic nerve." *Brain, Behavior, and Immunity* 21.5 (2007): 599-616.
Irintchev, et al. "The Injured and regenerating nervous system immunoglobulin superfamily members as key players." *The Neuroscientist* 18.5 (2012): 452-466.
Ito, et al. "Enhanced expression of Ibal, ionized calcium-binding adapter molecule 1, after transient focal cerebral ischemia in rat brain." *Stroke* 32.5 (2001): 1208-1215.
Karumbaiah, et al. "The upregulation of specific interleukin (IL) receptor antagonists and paradoxical enhancement of neuronal apoptosis due to electrode induced strain and brain micromotion." *Biomaterials* 33.26 (2012): 5983-5996.
Keast, et al. "Glutamate and aspartate immunoreactivity in dorsal root ganglion cells supplying visceral and somatic targets and evidence for peripheral axonal transport." *Journal of Comparative Neurology* 424.4 (2000): 577-587.
Kenwrick, el al. "Neural cell recognition molecule L1: relating biological complexity to human disease mutations," *Human Molecular Genetics* 9.6 (2000): 879-886.
Kim, et al. "Conducting polymers on hydrogel-coated neural electrode provide sensitive neural recordings in auditory cortex." *Acta Biomaterialia* 6.1 (2010): 57-67.
Kolarcik, et al. "In vivo effects of L1 coating on inflammation and neuronal health at the electrode-tissue interface in rat spinal cord and dorsal root ganglion." *Acta Biomaterialia* 8.10 (2012): 3561-3575.
Kozai, el al. "In vivo two-photon microscopy reveals immediate microglial reaction to implantation of microelectrode through extension of processes," *Journal of Neural Engineering* 9.6 (2012): 066001.
Kozai, et al, "Ultrasmall implantable composite microelectrodes with bioactive surfaces for chronic neural interfaces," *Nature Materials* 11.12 (2012): 1065-1073.
Kozai, et al, "L1 coating improves neural electrode integration as revealed by multi-photon microscopy," abstract submitted in Apr. 2013 to Biomedical Engineering Society (BMES) meeting in Sep. 2013.
Lagenaur, et al, "Monoclonal 12F8 antibody identifies a subclass of N-CAM active in promotion of neurite outgrowth," *Society for Neuroscience Abstract* vol. 14. p. 2253 (1988).
Lagenaur, et al. "An L1-like molecule, the 8D9 antigen, is a potent substrate for neurite extension." *Proceedings of the National Academy of Sciences* 84.21 (1987): 7753-7757.
Lago, et at. "Neurobiological assessment of regenerative electrodes for bidirectional interfacing injured peripheral nerves." *Biomedical Engineering, IEEE Transactions on* 54.6 (2007): 1129-1137.
Lahann, et al. "Synthesis of Amino [2.2] paracyclophanes—beneficial monomers for bioactive coating of medical implant materials." *Angewandte Chemie International Edition* 40:16 (2001): 2947-2947.
Lemmon, et al. "L1-mediated axon outgrowth occurs via a homophilic binding mechanism." *Neuron* 2.6 (1989): 1597-1603.

(56) References Cited

OTHER PUBLICATIONS

Lewicki. "A review of methods for spike sorting: the detection and classification of neural action potentials." *Network: Computation in Neural Systems* 9.4 (1998): R53-R78.

Ludwig, et al. "Chronic neural recordings using silicon microelectrode arrays electrochemically deposited with a poly (3, 4-ethylenedioxythiophene)(PEDOT) film." *Journal of Neural Engineering* 3.1. (2006): 59-70.

Luo, et al. "Electrochemically controlled release based on nanoporous conducting polymers." *Electrochemistry Communications* 11.2 (2009): 402-404.

Luo, et al. "Sponge-like nanostructured conducting polymers for electrically controlled drug release." *Electrochemistry Communications* 11.10 (2009): 1956-1959.

Luo, et al. "Pure graphene oxide doped conducting polymer nanocomposite for bio-interfacing." *Journal of Materials Chemistry B* 1.9 (2013): 1340-1348.

Maness, et al. "Neural recognition molecules of the immunoglobulin superfamily: signaling transducers of axon guidance and neuronal migration." *Nature Neuroscience* 10.1 (2006): 19-26.

Mori, et al. "Iba1-expressing microglia respond to herpes simplex virus infection in the mouse trigeminal ganglion." *Molecular Brain Research* 120.1. (2003): 52-56.

Musallam, et al. "A floating metal microelectrode array for chronic implantation."*Journal of Neuroscience Methods* 160.1 (2007): 122-127.

Nimmerjahn, et al. "Resting microglial cells are highly dynamic surveillants of brain parenchyma in vivo." *Science* 308.5726 (2005): 1314-1318.

Nosworthy, et al. "A new surface for immobilizing and maintaining the function of enzymes in a freeze-dried state." *Biomacromolecules* 10.9 (2009): 2577-2583.

Ohsawa, et al. "The expression of bone matrix protein mRNAs around β-TCP particles implanted into bone." *Journal of Biomedical Materials Research* 52.3 (2000): 460-466.

Panetsos, et al. "Neural prostheses: electrophysiological and histological evaluation of central nervous system alterations due to long-term implants of sieve electrodes to peripheral nerves in cats." *Neural Systems and Rehabilitation Engineering, IEEE Transactions on* 16.3 (2008): 223-232.

Pardue, et al. "Immunohistochemical studies of the retina following long-term implations with subretinal microphotodiode arrays." *Experimental Eye Research* 73.3 (2001): 333-343.

Pettersen, et al. "Amplitude variability and extracellular low-pass filtering of neuronal spikes." *Biophysical Journal* 94.3 (2008): 784-802.

Polikov, et al. "Response of brain tissue to chronically implanted neural electrodes." *Journal of Neuroscience Methods* 148.1 (2005): 1-18.

Purcell, et al. "In vivo evaluation of a neural stem cell-seeded prosthesis." *Journal of Neural Engineering* 6.2 (2009): 026005.

Purcell, et al. "Flavopiridol reduces the impedance of neural prostheses in vivo without affecting recording quality." *Journal of Neuroscience Methods* 183.2 (2009): 149-157.

Rao, et al. "Adhesion molecule-modified biomaterials for neural tissue engineering." *Frontiers in Neuroengineering* 2 (2009).

Rennaker, et al. "Minocycline increases quality and longevity of chronic neural recordings." *Journal of Neural Engineering* 4.2 (2007): L1.

Rothschild. "Neuroengineering tools/applications for bidirectional interfaces, brain-computer interfaces, and neuroprosthetic implants—a revieve of recent progress." *Frontiers in Neuroengineering* 3 (2010).

Ryu, et al. "Human cortical prostheses: lost in translation?." *Neurosurgical Focus* 27.1 (2009): E5.

Schmid, et al. "L1 and NCAM adhesion molecules as signaling coreceptors in neuronal migration and process outgrowth." *Current Opinion in Neurobiology* 18.3 (2008): 240-250.

Schwartz. "Cortical neural prosthetics," *Annu. Rev. Neurosci.* 27 (2004): 487-507.

Schwartz, et al. "Brain-controlled interfaces: movement restoration with neural prosthetics." *Neuron* 52.1 (2006): 205-220.

Seymour, et al. "Fabrication of polymer neural probes with subcellular features for reduced tissue encapsulation." *Engineering in Medicine and Biology Society, 2006. EMBS'06, 28th Annual International Conference of the IEEE*. IEEE, 2006.

Sharma, et al. "Scar-mediated inhibition and CSPG receptors in the CNS." *Experimental Neurology* 237.2 (2012): 370-378.

Sia, et al. "Microfluidic devices fabricated in poly (dimethylsiloxane) for biological studies." *Electrophoresis* 24.21 (2003): 3563-3576.

Sofroniew, et al. "Astrocytes: biology and pathology." *Acta Neuropathologica* 119.1 (2010): 7-35.

Stence, et al. "Dynamics of microglial activation: A confocal time-lapse analysis in hippocampal slices," *Glia* 33.3 (2001): 256-266.

Stensaas, et al. "Histopathological evaluation of materials implanted in the cerebral cortex." *Acta Neuropathologica* 41.2 (1978): 145-155.

Straley, et al. "Design and adsorption of modular engineered proteins to prepare customized, neuron-compatible coatings." *Frontiers in Neuroengineering* 2 (2009).

Strehin, et al. "A versatile pH sensitive chondroitin sulfate—PEG tissue adhesive and hydrogel." *Biomaterials* 31.10 (2010): 2788-2797.

Szarowski, et al. "Brain responses to micro-machined silicon devices." *Brain Research* 983.1 (2003): 23-35.

Thilakarathne, et al. "Protein polymer conjugates: improving the stability of hemoglobin with poly (acrylic acid)." *Langmuir* 27.12 (2011): 7663-7671.

Turner, et al. "Cerebral astrocyte response to micromachined silicon implants." *Experimental Neurology* 156.1 (1999): 33-49.

Wadhwa, et al. "Electrochemically controlled release of dexamethasone from conducting polymer polypyrrole coated electrode." *Journal of Controlled Release* 110.3 (2006): 531-541.

Webb, et al. "Substrate-bound human recombinant L1 selectively promotes neuronal attachment and outgrowth in the presence of astrocytes and fibroblasts." *Biomaterials* 22.10 (2001): 1017-1028.

Winslow, et al. "Quantitative analysis of the tissue response to chronically implanted microwire electrodes in rat cortex." *Biomaterials* 31.7 (2010): 1558-1567.

Zhang, et al. "Chemical surface modification of parylene C for enhanced protein immobilization and cell proliferation." *Acta Biomaterialia* 7.10 (2011): 3746-3756.

\* cited by examiner

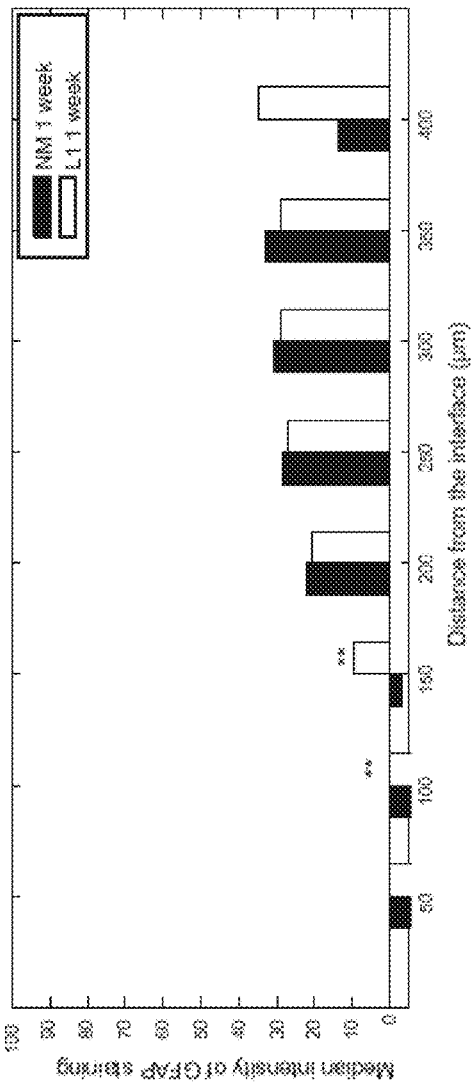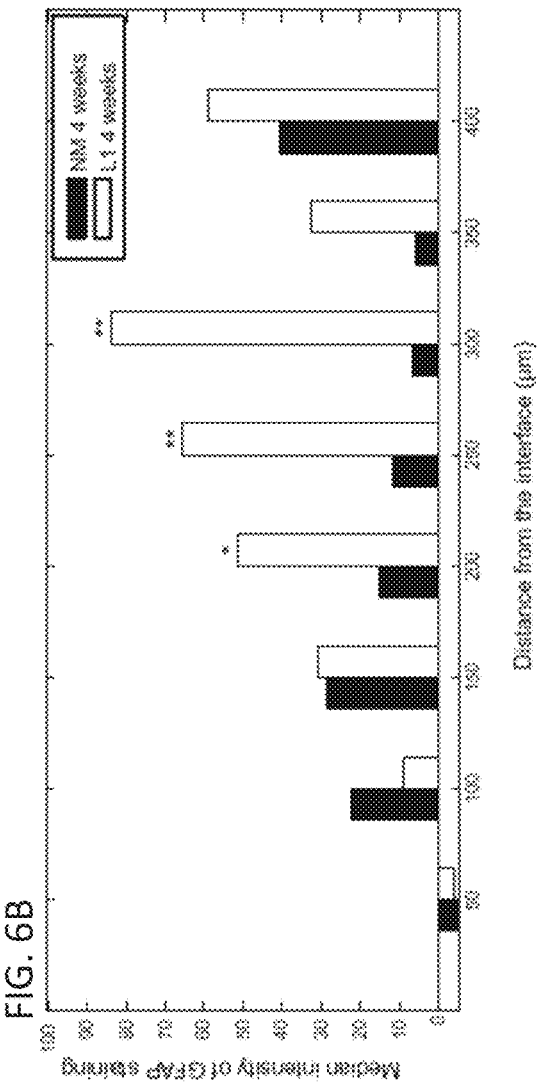

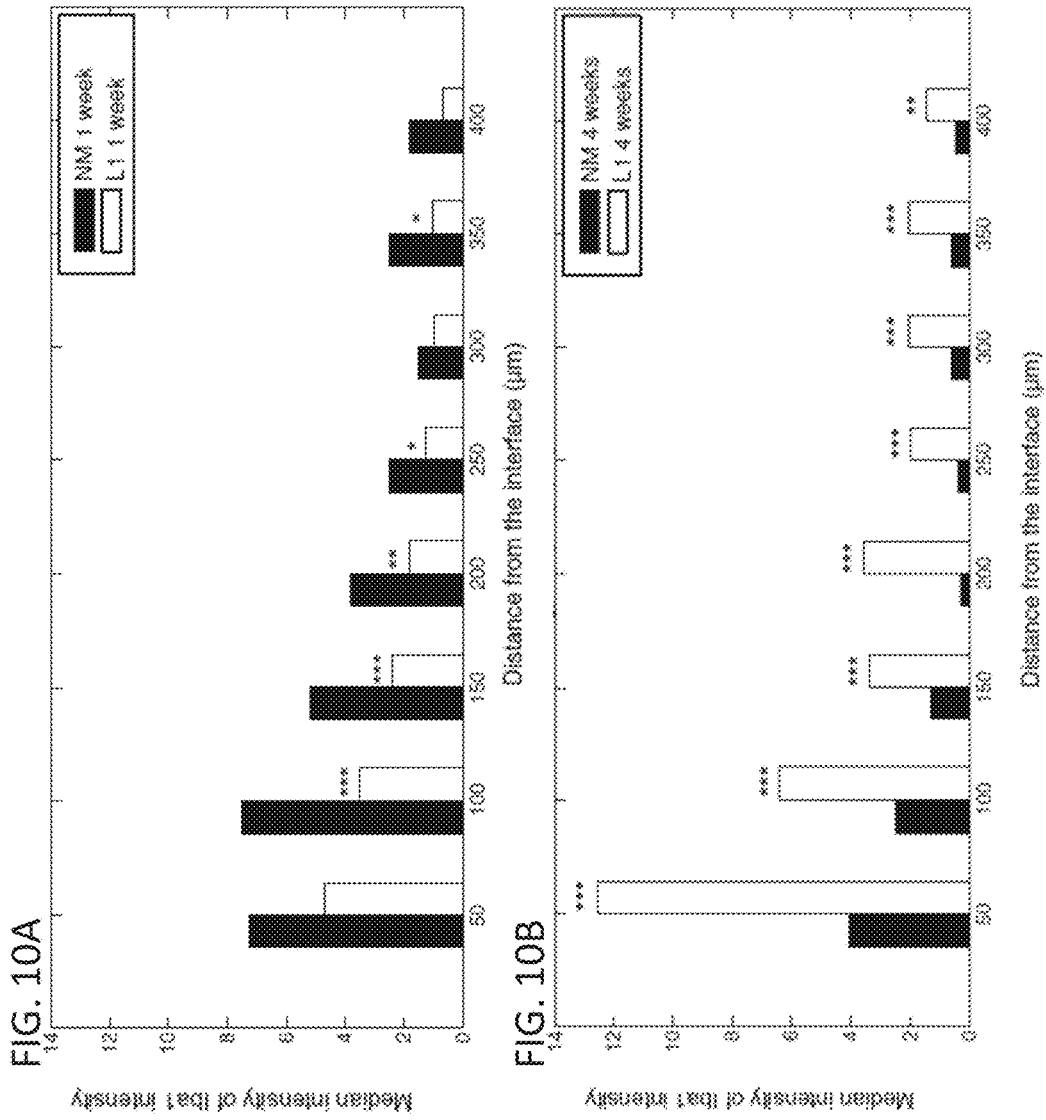

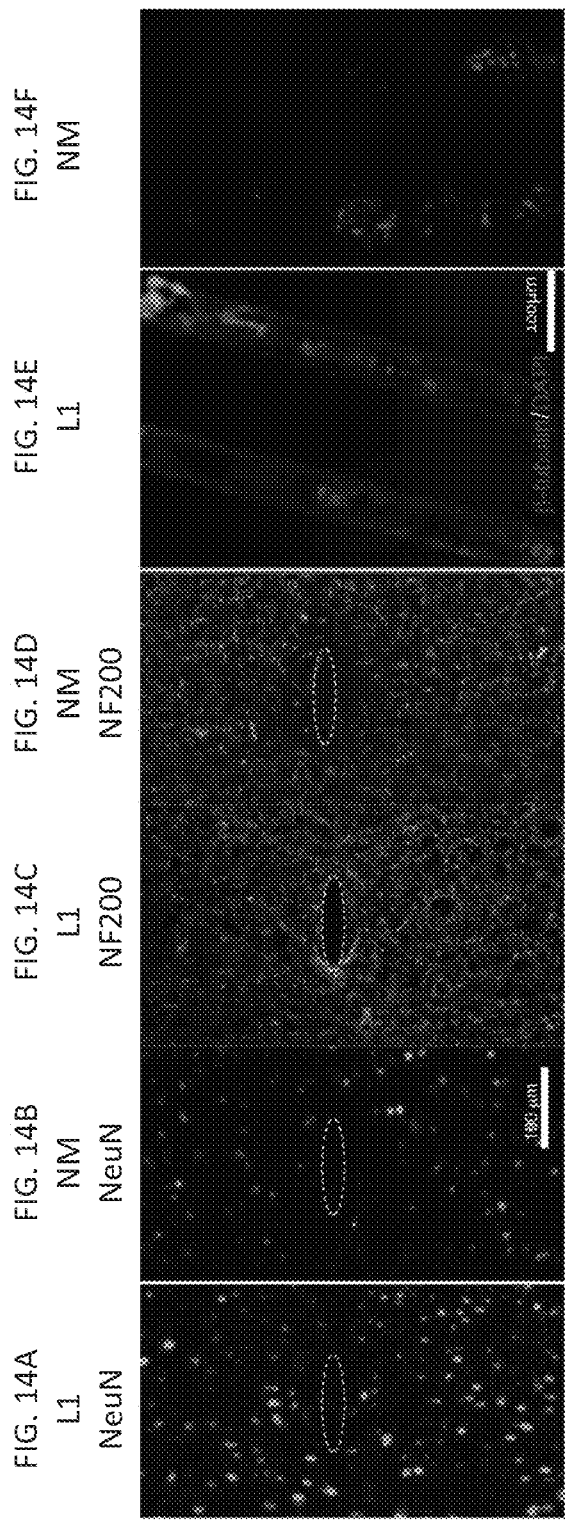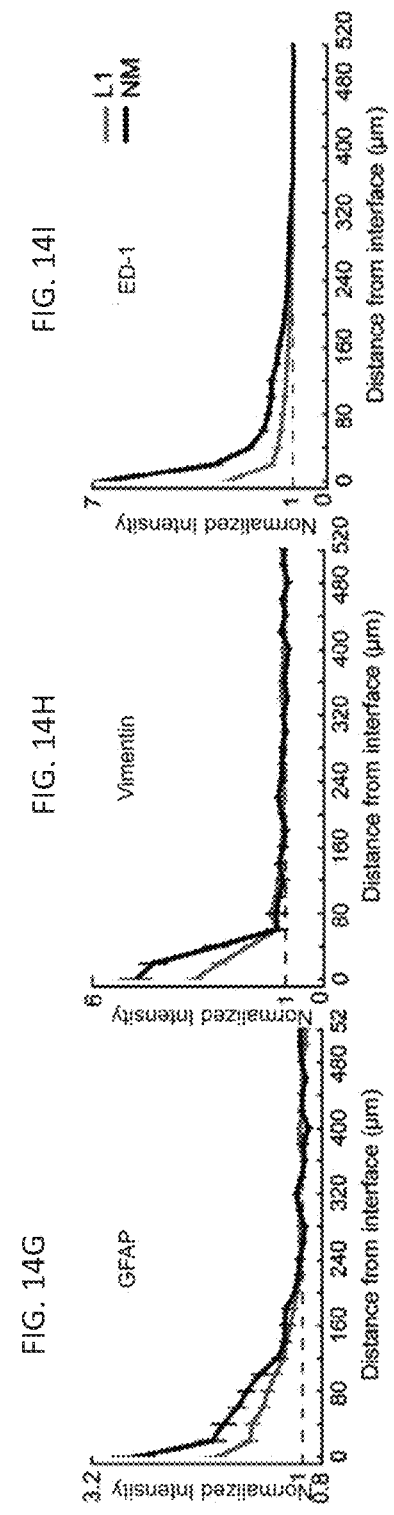

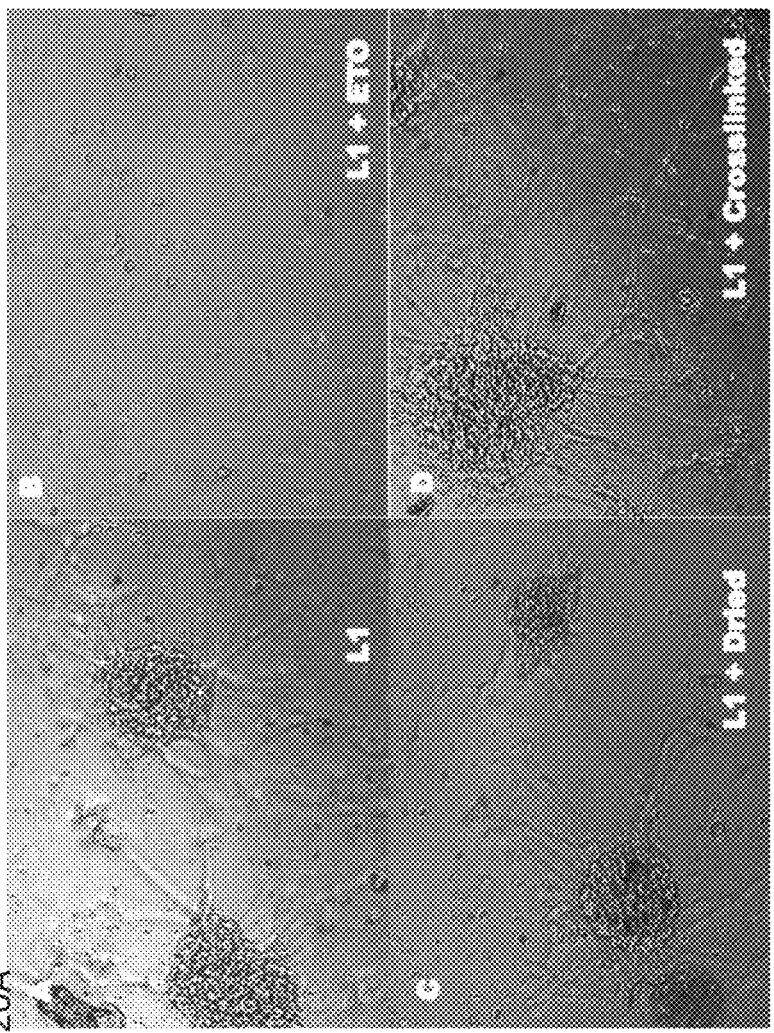

FIG. 21A
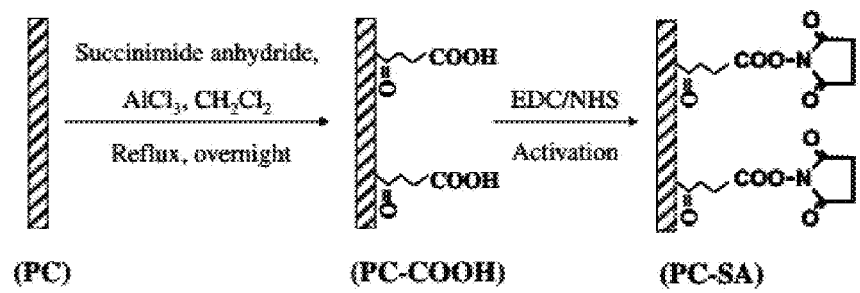
FIG. 21B
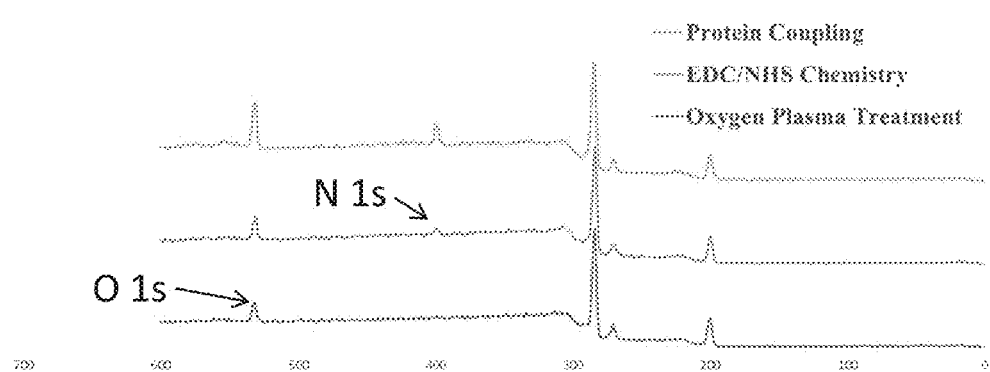
FIG. 21C
| Surface | O:Cl Ratio | N:Cl Ratio |
|---|---|---|
| Oxygen Plasma Treatment | 2.04 | 1.38 |
| EDC/NHS Chemistry | 2.34 | 1.89 |
| Protein Coupling | 3.61 | 2.57 |

BIOMIMETIC COATING FOR NEURAL IMPLANTS

CROSS REFERENCE TO RELATED APPLICATIONS

This application claims priority to U.S. Provisional Application No. 61/841,223, filed Jun. 28, 2013, which is incorporated by reference in its entirety.

ACKNOWLEDGMENT OF GOVERNMENT SUPPORT

This invention was made with government support under Grant No. NS062019 awarded by the National Institutes of Health and Grant No. N66001-12-C-4027 from the Defense Advances Research Projects Agency. The government has certain rights in the invention.

FIELD

The present disclosure relates to the field of physiological monitoring and stimulation of neural signals. In some embodiments, a neural probe including a protein coating is provided to increase the quality and quantity of recorded and/or stimulated neural signals.

BACKGROUND

Chronic neural implants, such as drug delivery devices, diagnostic sensors or neural probes, ideally minimize detrimental tissue responses and impairment of neural function throughout the entire implantation life of the implant. This challenge is particularly critical for neural probes, which are implanted in neural tissue and include electrodes that interface with biological host neurons. The recording and stimulation performance of currently available neural probes and devices including them decreases over time when chronically implanted for long-term clinical applications. Thus, a need exists for improved neural probes and devices incorporating such probes for chronic implantation and long-term clinical application to facilitate recording and stimulation performance that is more reliably maintained for prolonged periods of time.

SUMMARY

Disclosed herein are neural probes comprising one or more electrodes, an insulating layer, and an effective amount of an L1 polypeptide or functional fragment thereof on an exterior surface of the probe, devices including such probes, and methods of their use. In several embodiments, the insulating layer is a parylene C insulating layer and the L1 polypeptide or functional fragment thereof can be conjugated to the parylene C insulating layer. The probes and devices are unexpectedly useful for neural recording and/or stimulation. Unlike prior electrodes and devices, the disclosed embodiments allow for neural recordings of increased quality and quantity of neural recordings over time, and for a surprisingly long duration for which an implanted device can be used for effective neural recording and stimulation.

In several embodiments, a method of recording and/or stimulating a neural signal in a subject is provided. The method comprises implanting a neural probe for recording and/or stimulating the neural signal into neuronal tissue in the subject. The probe comprises one or more electrodes comprising a surface exposed to the exterior of the probe and insulated electrical conductors having non-insulated ends, wherein the electrical conductors extend through the probe and one or more of the non-insulated ends contact the electrodes. The probe also comprises a parylene C insulating layer coating a portion of the exterior surface of the probe, except for the surface of the electrodes exposed to the exterior of the probe, and an effective amount of L1 polypeptide or a functional fragment thereof on the exterior surface of the probe. The method further includes connecting the probe to a recording and/or stimulating apparatus via one or more electrical leads; and recording and/or stimulating the neural signal from the neuronal tissue. In additional embodiments, the method comprises recording and/or stimulating the neural signal after the probe has been implanted in the neuronal tissue for at least one year, for example the method can comprise recording at least four sortable neural units from at least one electrode on the probe after the probe has been implanted in the neuronal tissue for at least one year.

In other embodiments, a neural probe for recording and/or stimulating a neural signal in a subject is provided. The neural probe comprises one or more electrodes comprising a surface exposed to the exterior of the probe and insulated electrical conductors having non-insulated ends, wherein the electrical conductors extend through the probe and one or more of the non-insulated ends contact the electrodes. The probe also comprises a parylene C insulating layer coating a portion of the exterior surface of the probe, except for the surface of the electrodes exposed to the exterior of the probe, and an effective amount of L1 polypeptide or a functional fragment thereof on the exterior surface of the probe.

In some embodiments, the effective amount of the L1 polypeptide or functional fragment thereof comprises an amount of the L1 polypeptide or a functional fragment thereof sufficient to allow recording of at least four sortable neural units from at least one electrode after the probe has been implanted for at least six months. In further embodiments, the L1 polypeptide or functional fragment thereof is conjugated to the insulating layer. In more embodiments, the probe comprises from about 0.1 ng/mm$^2$ to about 2.0 ng/mm$^2$ L1 polypeptide or functional fragment thereof on the exterior surface. In some embodiments, the L1 polypeptide comprises or consists of the amino acid sequence set forth as SEQ ID NO: 1, or an amino acid sequence at least 90% identical to SEQ ID NO: 1. In additional embodiments, the functional fragment of the L1 polypeptide comprises or consists of the extracellular domain of L1, such as a polypeptide including an amino acid sequence at least 90% identical to amino acids 20-1120 of SEQ ID NO: 1. In some embodiments, the L1 polypeptide is purified from neuronal tissue.

In several embodiments, the neural probe or a plurality thereof is included in a device for recording and/or stimulating a neural signal in a subject. In some embodiments, the device is a microarray for recording and/or stimulating a neural signal, or a deep brain stimulator. Methods of making the disclosed neural probes and devices are also disclosed.

The foregoing and other objects, features, and advantages of the embodiments will become more apparent from the following detailed description, which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 6A and 6B show a set of graphs illustrating GFAP staining intensity as a function of distance from the electrode-tissue interface in the spinal cord. MATLAB was used to determine the decline in GFAP staining intensity at 1 week (A) and 4 week (B) time points. The perimeter of the implant site was defined using the DAPI-stained images. Threshold values based on 95% of the background staining for each section were established and GFAP staining above this threshold measured as a function of distance from the implant site. The median intensity values were calculated in 50 μm bins and compared via the rank sum test. Significant increases were observed with the L1 coating at both 1 week and 4 weeks. *$p<0.05$; **$p<0.01$.

FIG. 10 shows a set of graphs illustrating Iba1 staining intensity as a function of distance from the electrode-tissue interface in DRG following implant of NM and L1-coated neural probes. MATLAB was used to determine the decline in Iba1 staining intensity at 1 week (A) and 4 week (B) time points. The perimeter of the implant site was defined using the DAPI-stained images. Threshold values based on 95% of the background staining for each section were established, and Iba1 staining above this threshold measured as a function of distance from the implant site. The median intensity values were calculated in 50 μm bins and compared via the rank sum test. Significant decreases were observed with the L1 coating at the 1 week time point. At 4 weeks, the L1 coating was associated with significant increases in Iba1 staining. *$p<0.05$; $p<0.01$; *$p<0.001$.

FIGS. 14A-14I shows a series of immunofluorescence images and graphs illustrating brain tissue response to non-modified and L1 coated NeuroNexus probes (from the NeuroNexus training kit, with linear silicon shank) in comparison to uncoated controls. Neuronal density is maintained at the vicinity of the probe track (A) while a kill zone is found around the control (B), as illustrated by NeuN staining. Axonal growth is enhanced around the L1 probe (C) while control probes had a lower neurofilament staining (D), as illustrated by NF200 staining. Explanted L1 probes show direct neuron attachment as indicated by β-III-tubulin staining (E) while the control probes were covered with cells that are not neuronal (F), as illustrated by β-tubulin (green) and DAPI (blue) staining. Quantitative image analysis showed different markers of reactive tissue responses. The intensities of the staining were averaged across sections and animals, normalized to control tissue and plotted against distance to the probe-tissue interface for GFAP (G), vimentin (H) and ED-1(I).

FIGS. 20A-20D show light microscopy images illustrating the L1 coating stability under varying conditions. (A) L1 coated parylene C, (B) L1 coating exposed to overnight ethylene oxide sterilization, (C) L1 coating dried at room temperature, and (D) L1 'lightly' crosslinked with enzymatic production of superoxide.

FIGS. 21A-21C show a schematic diagram, graph and table illustrating attachment of L1 to paralyene C coated substrates using ethyl(dimethylaminopropyl) carbodiimide (EDC)/N-Hydroxysuccinimide (NHS) crosslinking following oxygen plasma treatment.

SEQUENCE LISTING

Figure 1A:
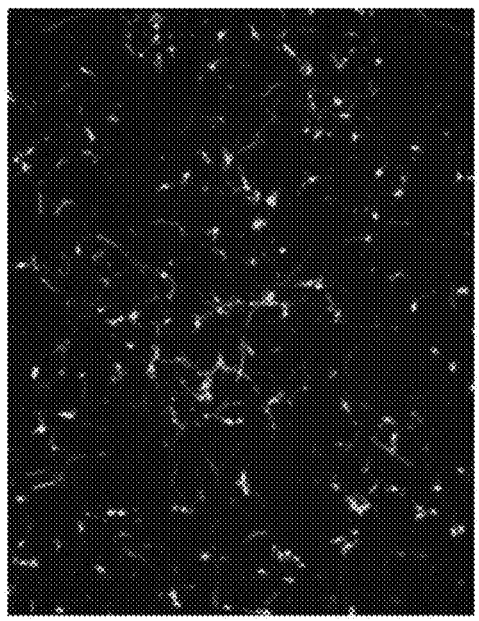
FIGS. 1A-1D show a graph and a set of images illustrating the quantification of cell adhesion with different probe surface modifications. Parylene-C-treated microwires coated with L1, Plasma, or Laminin were added to primary neuron, microglia or astrocyte cultures and cell-type specific staining was used to identify the cell types attached to each surface. Cell numbers were calculated by dividing the total number of cells by the surface area. Significant increases in neuronal adhesion were observed with L1 and laminin. Error bars represent the mean±standard error of the mean (SEM). $p<0.01$; *$p<0.001$.
Figure 1B:
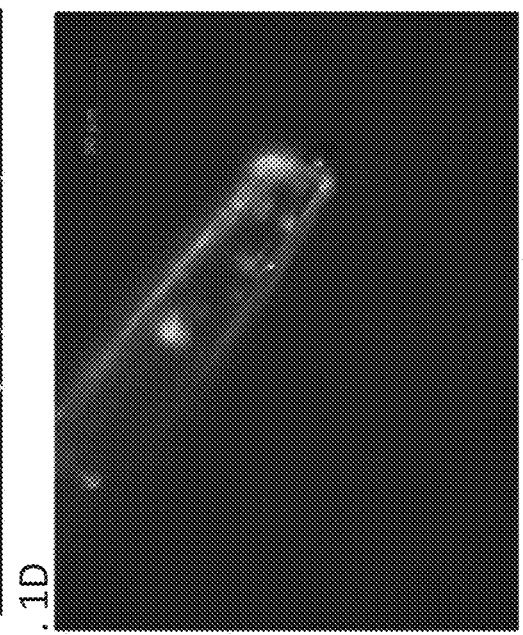
Figure 1C:
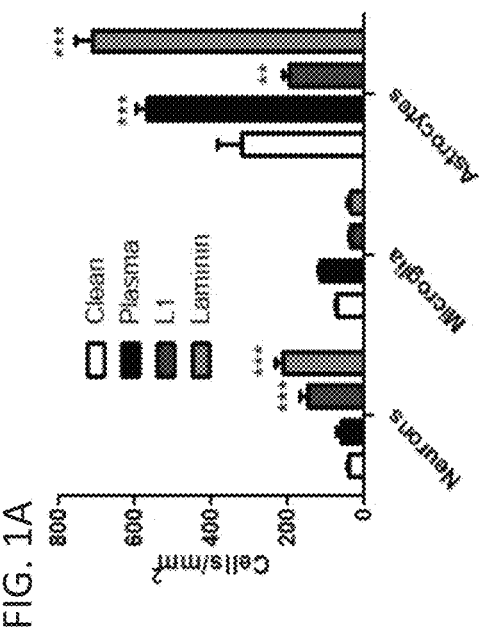
Figure 1D:
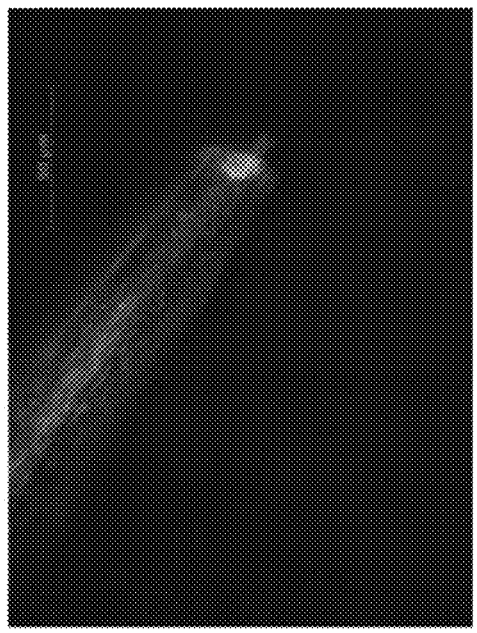

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~40 kb), which was created on Jun. 27, 2014, which is incorporated by reference herein. In the accompanying sequence listing:

DETAILED DESCRIPTION

I. Introduction

The recording and stimulation performance of currently available neural recording and stimulation devices decreases over time. For example, clinical grade Blackrock arrays in monkey motor cortex were found to have a 2.4% drop per month in signal amplitude (see, e.g., Chestek et al., "Long-term stability of neural prosthetic control signals from silicon cortical arrays in rhesus macaque motor cortex," J Neural Eng., 8(4): p. 045005, 2011, incorporated by reference herein in its entirety). Many factors contribute to failure in chronic implants, including implantation procedure, implant size and geometry, mechanical mismatch, connector or packaging failure, and material degradation. While most of these factors have been improved over the years of accumulated experience and continue to show promising improvements, the most significant challenge is the issue of biocompatibility. In repeated studies by multiple groups, brain tissue response, particularly neuronal loss and chronic inflammation around the implant have been observed in the vicinity of implanted electrodes, which are believed to contribute to chronic recording failure.

Implanted neural probes include electrodes that detect neuronal action potentials by detecting extracellular electrical potential changes (10's to 100's of microvolt) in reference to a ground. The closer the electrode is to a neuron, the better signal strength and quality of neural signals that can be recorded from the electrode. It is reported that 50-100 μm is the maximum distance that a microelectrode can obtain measurable signals from a neuron. For high quality long-term stable recording, the proximity of electrodes to neurons needs to be maintained over time. However, repeated immunohistology studies by multiple groups have shown "kill zones" around neural implants, where neural densities have significantly lowered around the implant (see, e.g, Edell et al., IEEE Trans. Biomed. Eng., 1992. 39: p. 635-643; and Szarowski et al., Brain Research, 2003. 983(1-2): p. 23-35; Turner et al., Experimental neurology, 1999. 156: p. 33-49, each of which is incorporated by reference herein). The electrode then has to detect neural signal from further away (beyond the kill zone) leading to lower yield of single-unit and recorded amplitude of neural signals.

Many different biomaterial strategies have been developed to improve the tissue response to neural probe implantation but the success in improved recording has been limited (see, e.g., Kim et al., Acta Biomater. 6(1): p. 57-62; Ludwig et al., J Neural Eng, 2006. 3(1): p. 59-70; Seymour and Kipke, Conf Proc IEEE Eng Med Biol Soc, 2006. 1: p. 4606-9; Purcell et al., J Neural Eng, 2009. 6(2): p. 026005; Purcell et al., J Neurosci Methods, 2009. 183(2): p. 149-57; Kozai et al., Nat Mater, 2012. 11(12): p. 1065-73; and Rennaker et al., J Neural Eng, 2007. 4(2): p. L1-5, each of which is incorporated herein).

It is generally believed that many factors contribute to the low yield and poor longevity of current neural implants, including, but not limited to, insertion trauma, surface chemistry, mechanical mismatch, persistent blood-brain leakage associated with the implants, and material failure. It is expected that it would take a combinatorial approach that addresses more than one of the above problems to achieve a substantial improvement in recording performance (see, e.g., Polikov, Tresco, and Reichert, J Neurosci Methods, 2005. 148(1): p. 1-18.). Surprisingly, the disclosed strategies to improve the recording and stimulation performance of neural probes utilizing a simple improvement—including L1 polypeptide, a brain-derived neuronal adhesion molecule, or a functional fragment thereof, on the exterior surface of the neural probe. In several embodiments, the probe includes a parylene C insulating layer, and the L1 polypeptide or functional fragment thereof is conjugated to the exterior surface of the parylene C layer. The disclosed improvements in neural probe technology unexpectedly provide for increased quality and quantity of neural recordings over time, and for a surprisingly long duration for which an implanted probe can be used for effective neural recording and stimulation.

II. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references. As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In addition, the materials, methods, and examples are illustrative only and not intended to be limiting. The scope of the claims should not be limited to those features exemplified. To facilitate review of the various embodiments, the following explanations of terms are provided:

Coat: A layer of material that partially or fully covers a surface. For example, an insulating layer can fully coat the exterior surface of an electrical conductor with a non-conductive material to facilitate conduction of neural signals along the conductor.

In several embodiments, the neural probes disclosed herein include an external surface with a coat of L1-polypeptide or functional fragment thereof on an external surface. An "L1-coated probe" includes an effective amount of L1 polypeptide or a functional fragment on its exterior surface. The probe does not need to be completely coated with L1 (an in many cases is partially coated); the amount of L1 polypeptide or functional fragment thereof included in an "L1-coat" on the external surface of a probe can vary according to the application parameters, e.g., time of use, exposure, level of signals, levels of noise, desired protein density, etc. Coating material can be applied to an underlying surface in various ways known in the art and describe herein. Non-limiting examples of methods that can be used to apply the L1 polypeptide or functional fragment thereof to the external surface of the probe include coating methods such as dipping, spraying, painting, vacuum deposition, conjugation to the external surface of the probe (e.g., by conjugation to the insulating layer, discussed in more detail below), or by any other method known to those of ordinary skill in the art.

Conservative variants: "Conservative" amino acid substitutions are those substitutions that do not substantially alter the biological function of a protein, such as substitutions that do not substantially decrease the bioactivity of a L1 polypeptide. For example, a human L1 polypeptide can include at most about 1, at most about 2, at most about 5, at most about 10, at most about 15, at most about 20, at most about 30, at most about 40, or at most about 50 conservative substitutions and still retain bioactivity needed to improve recording and/or stimulation of neural signals as disclosed herein. The term conservative variation also includes the use of a substituted amino acid in place of an unsubstituted parent amino acid.

Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Effective amount: The amount of an agent (such as a L1 polypeptide or functional fragment thereof) that alone, or together with one or more additional agents, induces the desired response, such as, for example, increased recording and/or stimulation of neural signals as disclosed herein.

Electrode: An electric conductor through which an electric current can pass. An electrode can also be a collector and/or emitter of an electric current. In some embodiments, an electrode is a solid and comprises a conducting metal as the conductive layer. Non-limiting examples of conducting metals include noble metals and alloys, such as stainless steel and tungsten. An "array of electrodes" refers to a device with at least two electrodes formed in any pattern. The electrodes can be either interconnected or independently wired.

Implanting: Completely or partially placing a neural probe or device including a neural probe within a subject, for example, using surgical techniques. A device or probe is partially implanted when some of the device or probe reaches, or extends to the outside of, a subject.

Implantable probes and devices may be implanted into neural tissue, such as the central nervous system, more particularly the brain, for treatment of different medical conditions and for various time periods. A neural probe or device can be implanted for varying durations, such as for a short term duration (e.g., one or two days or less) or for long-term or chronic duration (e.g., one month or more).

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

L1: A type-1 transmembrane protein also known as L1CAM that is a member of the immunoglobulin superfamily. L1 is known to be involved in axon outgrowth and fasciculation, neuronal migration and survival, synaptic plasticity and regeneration after trauma, and can interact with itself (homophilic) but also with a variety of heterophilic ligands such as integrins, CD24, neurocan, neuropilin-1 and other members of the neural cell adhesion family. (For review, see Schmid and Maness, *Curr Opin. Neurobiol.*, 18, 245-250, 2008; Maness et al., Nat Neurosci, 10:19-26, 2007, and Figge et al., Mol Cell Neurosci, 2011).

The L1 family of cell adhesion molecules includes at least four different L1-like proteins, including L1, CHL1 (close homologue of L1), Neurofascin, and NrCAM (NgCAM related cell adhesion molecule). The amino acid sequence of these proteins are known, and are publically available as GenBank Accession Nos. NP_000416.1 (L1), BC047244.1 (NCAM1), AAI43497 (CHL1), O94856 (Neurofascin), each of which is incorporated by reference herein in its entirety. Several embodiments include a functional fragment of L1. As used herein, a "functional fragment of L1" is a polypeptide including less than the full amino acid sequence of mature L1, and which can be conjugated to a parylene C insulated electrode to generate a L1-coated electrode that provides a similar effect on neural signal recording as that of a control electrode including a parylene C insulating layer conjugated to L1 purified from neural tissue (as described in Example 1, below).

Standard methods in the art can be used to produce an L1 polypeptide or functional fragment thereof, including expression of recombinant L1 or a functional fragment thereof using molecular biology techniques, or purification of L1 from neural tissue (e.g., as described in Lagenaur and Lemmon, V, *An L1-like molecule, the 8D9 antigen is a potent substrate for neurite extension*. Proc. Natl. Acad. Sci. USA, 84:7753-7757, 1987).

Neural probe: A device or component of a device including one or more electrodes that can be placed in contact with neuronal tissue in an animal host and can record and/or stimulate neural signals from or to the neuronal tissue. Neural probes typically include conductive and non-conductive surfaces designed for contact with neuronal tissue when implanted in a subject, and can include one or more electrodes that can be independently monitored from other conductive surfaces on or off the probe) for recording and/or stimulating neural signals. In several embodiments, the disclosed probes are included in a device (such as an array or a deep brain stimulator) for recording and/or stimulating a neural signal in a subject.

Neural signal: An electrical signal originating in the nervous system of a subject. "Recording a neural signal" refers to recording an electrical signal that independently exists outside of the membrane or wall of a cell. "Stimulating a neural signal" refers to application of an electrical current to the neural tissue of a subject in such a way as to cause neurons in the subject to produce an electrical signal (e.g., an action potential). An extracellular electrical signal can, however, originate in a cell, such as one or more neural cells. An extracellular electrical signal is contrasted with an intracellular electrical signal, which originates, and remains, in a cell. An extracellular electrical signal can comprise a collection of extracellular electrical signals generated by one or more cells. The person of ordinary skill in the art is familiar with methods for recording electrical signals using a device including an implanted electrode.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer and/or constructed using standard molecular biology techniques. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Polypeptide: Any chain of amino acids, regardless of length or post-translational modification (e.g., glycosylation or phosphorylation). In one embodiment, the polypeptide is a L1 polypeptide or a functional fragment thereof. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Polypeptide modifications: polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Purified: The term purified does not require absolute purity; rather, it is intended as a relative term. Thus, for example, a purified peptide preparation is one in which the peptide or protein (such as L1 protein) is more enriched than the peptide or protein is in its natural environment within a cell or tissue. In one embodiment, a preparation is purified such that the protein or peptide represents at least 50% of the total peptide or protein content of the preparation, such as at least 80%, at least 90%, at least 95% or greater of the total peptide or protein content.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is a protein encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

An example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

Subject: Living multi-cellular vertebrate organisms, a category that includes human and non-human mammals, including non-human primates, rats, mice, guinea pigs, cats, dogs, cows, horses, and the like. Thus, the term "subject" includes both human and veterinary subjects.

III. L1 Coated Probes and Methods of Making and Using Same

A. Probes and Devices for Recording and/or Stimulating Neural Signals

Figure 25A:
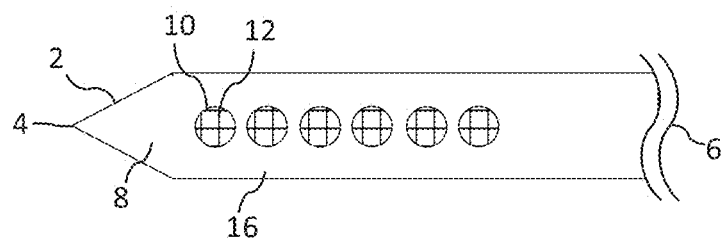
FIGS. 25A-25D illustrate an exemplary method of making a neural probe as provided herein.
Figure 25B:
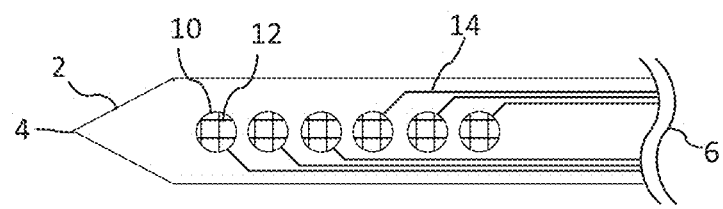

Several embodiments include a neural probe including one or more electrodes for recording and/or stimulating neural signals in a subject. FIGS. 25A-25D illustrate an exemplary probe 2 for use in the disclosed embodiments. As shown in FIG. 25A, the probe 2 can include a distal end 4, a proximal portion 6, and an exterior surface 8. The probe also includes one or more electrodes 10, each electrode having a surface 12 exposed to the exterior of the probe. The one or more electrodes 10 are each connected to an insulated electrical conductor 14 (shown in FIG. 25B) that extends through the probe and has first and second non-insulated ends. The first non-insulated end can be in electrical contact with an electrode 10, and the second non-insulated end can be in electrical contact with a connection portion of the probe (not shown) located at the proximal end of the probe. The connection portion of the probe can be connected to one or more leads for communication of electrical signals from the surface 12 of each electrode via the one or more insulated electrical conductors 14 and the lead to a recording or stimulating apparatus. Alternatively, the connection portion of the probe can be directly connected to the recording and/or stimulation apparatus. The probe includes an insulating layer 16 on its external surface that covers the external portion of the probe except for the surface 12 of the one or more electrodes. The insulating layer can cover the one or more insulated electrical conductors 14. FIG. 25A shows the probe with the insulating layer, and FIG. 25B shows the probe without the insulating layer for illustration purposes.

Figure 25C:
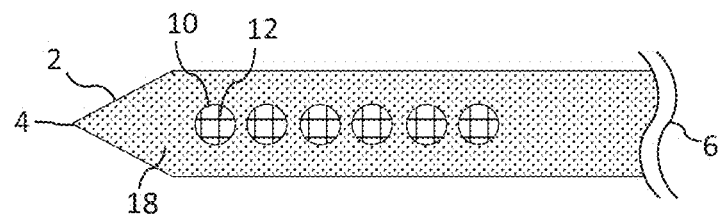
Figure 25D:
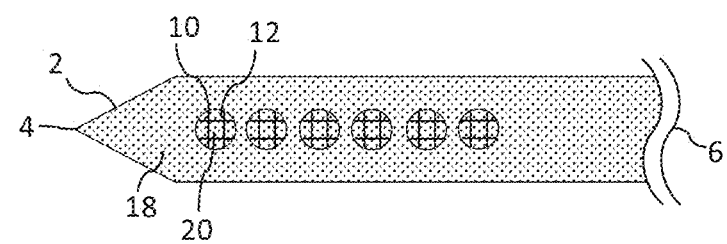

In the disclosed embodiments, the probe includes an effective amount of L1 polypeptide or a functional fragment thereof on its external surface. The L1 polypeptide or functional fragment thereof can be included in or on the external surface of the probe in any configuration that exposes the L1 polypeptide or functional fragment in a way that allows tissue surrounding an implanted probe to contact the L1 polypeptide or functional fragment thereof. Non-limiting examples of methods that can be used to apply the L1 polypeptide or functional fragment thereof to the external surface of the probe include coating methods such as dipping, spraying, painting, vacuum deposition, conjugation to the external surface of the probe (e.g., by conjugation to the insulating layer, discussed in more detail below), or by any other method known to those of ordinary skill in the art. In another embodiment, the L1 polypeptide or functional fragment thereof can be included in a composition used to make the insulating layer of the probe, and the composition can be applied thereon (e.g., using coating methods) to form the insulating layer of the probe. FIG. 25C illustrates an embodiment of the probe including an effective amount of L1 or a functional fragment thereof (shown with shading 18) in or on the external surface of the probe, wherein the L1 or functional fragment thereof does not cover the surface 12 of the electrode 10 exposed to the exterior of the probe; however, the L1 polypeptide or functional fragment can also be located on the surface 12 of the electrode (shown as shading 20 in FIG. 25D).

In several embodiments, the probe includes an insulating layer on its exterior surface. An "insulating layer" is a layer of non-conductive material deposited onto the exterior surface of the probe. The person of ordinary skill in the art will appreciate that, when the probe is used for recording and/or stimulation of neural signals, the non-conductive insulating layer does not coat the entire surface of the probe, the one or more electrodes included on the probe are exposed to the exterior surface of the probe to record and/or stimulate neural signals in surrounding neural tissue.

Non-limiting examples of materials for non-conductive insulating layers include parylene, silicon oxide, silicon nitride, polyimide, alumina, Teflon (PTFE), fluoropolymer, silicone, flurosilicone, or a combination of two or more thereof. In some embodiments, the insulation layer comprises or consists of parylene. In some embodiments, the parylene is parylene C, parylene A, parylene D, parylene N, parylene AF-4, or a combination of two or more thereof. In some embodiments, the insulating layer comprises or consist of parylene C. Methods of making electrodes for recording and/or stimulating a neural signal that are coated (fully or partially) with an insulting layer (including a parylene C insulating layer) are known in the art; see, e.g., U.S. Pat. No. 8,355,802 and WO 2005/114720, which are incorporated by reference herein in their entirety.

The probe includes an effective amount of L1 polypeptide or functional fragment thereof on its exterior surface. In some embodiments, the L1 polypeptide or functional fragment thereof can be conjugated the exterior surface of the probe (e.g., by conjugation to the insulating layer of the probe). The effective amount of L1 or functional fragment can vary depending on the particular application. In some embodiments, an effective amount of L1 polypeptide or functional fragment is an amount of the L1 polypeptide or functional fragment (e.g., a surface density of L1 polypeptide) sufficient to reduce the deleterious effects on neural recording quality over time (for example over a year), observed with a corresponding electrode that is not conjugated to an effective amount of L1 polypeptide. In additional embodiments, an effective amount of L1 polypeptide or functional fragment thereof includes an amount of L1 polypeptide or a functional fragment thereof on the exterior surface of the probe sufficient to allow recording of at least four sortable neural units from at least one electrode after the probe has been implanted for at least six months.

In some embodiments, the effective amount of L1 or functional fragment includes from about 0.1 ng/mm$^2$ to about 10.0 ng/mm$^2$ (such as about 0.1 ng/mm$^2$ to about 0.5 ng/mm$^2$, about 0.5 ng/mm$^2$ to about 1.0 ng/mm$^2$, about 1.0 ng/mm$^2$ to about 1.5 ng/mm$^2$, about 0.5 ng/mm$^2$ to about 2.0 ng/mm$^2$, about 1.0 ng/mm$^2$ to about 2.0 ng/mm$^2$, about 1.0 ng/mm$^2$ to about 5.0 ng/mm$^2$, about 1.5 ng/mm$^2$ to about 2.0 ng/mm$^2$, about 3.0 ng/mm$^2$ to about 5.0 ng/mm$^2$, about 5.0 ng/mm$^2$ to about 7.0 ng/mm$^2$, about 5.0 ng/mm$^2$ to about 10.0 ng/mm$^2$, about 7.0 ng/mm$^2$ to about 10.0 ng/mm$^2$, or about 1.0 ng/mm$^2$ to about 3.0 ng/mm$^2$) L1 polypeptide or functional fragment thereof on the exterior surface of the probe. In some embodiments, the effective amount of L1 or functional fragment includes from about 0.5 to about 1.0 ng/mm$^2$ L1 or functional fragment on the exterior surface of the probe. In some embodiments, the effective amount of L1 includes at least 0.2 ng/mm$^2$ L1 or functional fragment on the exterior surface of the probe (such as at least 0.3, 0.4, 0.5, 0.6, 0.7, 0.8, 0.9, 1.0, 1.5, 2.0 ng/mm$^2$ L1 or functional fragment, or more, on the exterior surface of the probe). Methods of determining the amount of L1 polypeptide on the exterior surface of the probe are known in the art. For example, a density of protein functionalization of ~0.66 ng/mm$^2$ has been observed for the protein functionalization of silica-based surfaces (Bhatia et al., Analytical Biochemistry 178 408-413, 1989, incorporated by reference herein). In some embodiments, dual polarization interferometry can be used to determine the surface bound L1 mass (see, e.g., Azemi et al., Surface immobilization of neural adhesion molecule L1 for improving the biocompatibility of chronic neural probes: In vitro characterization. Acta Biomaterialia, 2008. 4(5): p. 1208-1217, which is incorporated by reference herein in its entirety). Additional methods are also available, including, but not limited to, immunostaining of functionalized surfaces, attenuated total reflectance Fourier transform infrared spectroscopy (ATR-FTIR), X-ray photo-electron spectroscopy (XPS).

The disclosed probes can be included on a device designed for recording and/or stimulating a neural signal in a subject with neuronal tissue, such as any mammal, including humans, non-human primates, pigs, sheep, cows, rodents and the like.

Numerous types and styles of probes including one or more electrodes for recording and/or stimulating a neural signal are available, and known to the person of ordinary skill in the art. Any probe (or device containing the probe) for recording and/or stimulating neural signals in a subject may be used with the disclosed embodiments. In several embodiments, the probe includes more than one electrode, such as an array of electrodes. In additional embodiments, a device is provided that can include one or more probes, each of which can include one or more electrodes. Non-limiting examples include deep brain stimulators, EcoG grids, electrode arrays, microarrays (e.g., Utah and Michigan microarrays), and microwire electrodes and arrays. Probes (and devices including them can be inserted into the body, for example transcutaneously, intervertebally, or transcranially, to a target site in the body (for example, in the brain) where neural signals are to be recorded or stimulated.

Commercial sources of probes and devices for recording and/or stimulating neural signals in a subject, including probes coated with an insulating layer (such as Parylene C), are known. For example, such electrodes and devices are available commercially from Blackrock Microsystems (Salt Lake City, Utah) and NeuroNexus (Ann Arbor, Mich.).

B. L1 Polypeptides and Fragments Thereof

The disclosed probes include an L1 polypeptide or a functional fragment thereof on an exterior surface. In some embodiments the probe is coated with an insulating layer (such as a Parylene C insulating layer), wherein an exterior surface on the insulating layer is conjugated to the L1 polypeptide or a functional fragment thereof.

L1 (also known as L1CAM) is a 200-220 kD glycoprotein and is a member of the immunoglobulin superfamily. This type-1 transmembrane protein includes at least four immunoglobulin like ("Ig-like") domains at the amino terminal end of the polypeptide followed by five fibronectin type III homologous repeats, a single transmembrane region and a short intracellular domain (see FIG. 19). The Ig domains are known to be involved with L1-L1 homodimerization (Haspel et al., J Neurosci Res., 66:347-355, 2001, incorporated by reference herein in its entirety). At least two splicing variants are known encoding for 1257 and 1253 amino acids proteins. L1 is involved in axon outgrowth and fasciculation, neuronal migration and survival, synaptic plasticity and regeneration after trauma. L1 can interact with itself (homophilic) but also with a variety of heterophilic ligands such as integrins, CD24, neurocan, neuropilin-1 and other members of the neural cell adhesion family. (For review, see Schmid and Maness, L1 and NCAM adhesion molecules as signaling coreceptors in neuronal migration and process outgrowth," Curr Opin. Neurobiol., 18, 245-250, 2008; Maness "Neural recognition molecules of the immunoglobulin superfamily: signaling transducers of axon guidance and neuronal migration," Nat Neurosci, 10:19-26, 2007; Figge et al., "Neurite outgrowth triggered by the cell adhesion molecule L1 requires activation and inactivation of the cytoskeletal protein cofilin," Mol Cell Neurosci, 2011; each of which is incorporated by reference herein in its entirety).

Without being bound by theory, in the disclosed embodiments, the L1 polypeptide or functional fragment thereof on the exterior surface of the probe can interact with L1 polypeptide on the surface of cells in the neural tissue of a subject in which the probe is implanted. It is believed that the Ig-like domains 1-4 are involved in the L1-L1 binding.

Figure 19:
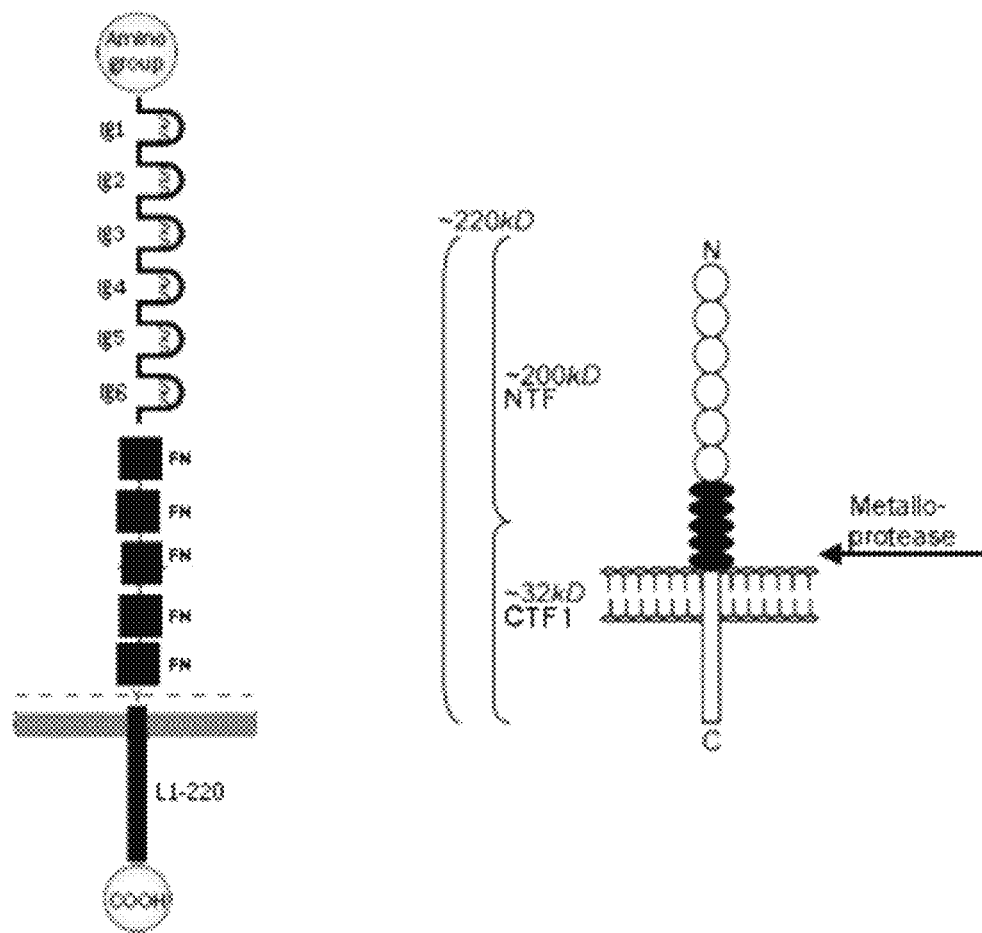
FIG. 19 shows a schematic diagram depicting the domains of L1.

Each is maintained by a disulfide bond (shown in FIG. 19 as s-s). The more cell-membrane proximal fibronectin type domains may contribute to signaling to the cell bearing the L1 but might not be expected to contribute to L1-L1 interaction.

The L1 family of cell adhesion molecules includes at least four different L1-like proteins, which are members of the immunoglobulin superfamily (IgSF CAMs). The members of the L1-family in humans include L1, CHL1 (close homologue of L1), Neurofascin and NrCAM (NgCAM related cell adhesion molecule). Any of the L1 family members (or a functional fragment of such family members) can also be used in the disclosed embodiments in place of L1 (or functional fragment thereof).

In some embodiments the L1 polypeptide or functional fragment thereof includes or consists of one or more of the Ig-like domain of L1, such as 1, 2, 3, or all 4 of the Ig1, Ig2, Ig3, and Ig4 Ig-like domains of L1. In some embodiments, the L1 polypeptide or functional fragment thereof includes or consists of the Ig1, Ig2, Ig3, and Ig4 Ig-like domains of L1. The person of skill in the art can readily determine the amino acid sequence of the Ig-like domains of L1 (for example, this information is available in the GenBank Accession entry for No. NP_000416.1 ). In some embodiments, that L1 polypeptide or functional fragment thereof includes or consists of the L1 extracellular domain. Exemplary regions of the L1 polypeptide as set forth in SEQ ID NO: 1 (which corresponds to the L1 sequence shown in GenBank Accession No. NP_000416.1) are shown in Table 1, below.

TABLE 1

Regions of L1

| Region | SEQ ID NO: 1 amino acids |
|---|---|
| Signal peptide | 1-19 |
| Ig1 | 53-130 |
| Ig2 | 134-228 |
| Ig3 | 260-330 |
| Ig4 | 347-422 |
| Extracellular region | 20-1120 |
| Transmembrane domain | 1121-1143 |
| Cytosolic region | 1144-1257 |
| Mature L1 polypeptide | 20-1257 |

Exemplary L1 polypeptide sequences are known. For example, L1 sequences are deposited as GenBank Accession Number NP_000416.1 (incorporated by reference herein as present in the database on Jun. 20, 2013):

(SEQ ID NO: 1)
MVVALRYVWPLLLCSPCLLIQIPEEYEGHHVMEPPVITEQSPRRLVVFPT

DDISLKCEASGKPEVQFRWTRDGVHFKPKEELGVTVYQSPHSGSFTITGN

NSNFAQRFQGIYRCFASNKLGTAMSHEIRLMAEGAPKWPKETVKPVEVEE

GESVVLPCNPPPSAEPLRIYWMNSKILHIKQDERVTMGQNGNLYFANVLT

SDNHSDYICHAHFPGTRTIIQKEPIDLRVKATNSMIDRKPRLLFPTNSSS

HLVALQGQPLVLECIAEGFPTPTIKWLRPSGPMPADRVTYQNHNKTLQLL

KVGEEDDGEYRCLAENSLGSARHAYYVTVEAAPYWLHKPQSHLYGPETA

RLDCQVQGRPQPEVTWRINGIPVEELAKDQKYRIQRGALILSNVQPSDTM

VTQCEARNRHGLLLANAYIYVVQLPAKILTADNQTYMAVQGSTAYLLCKA

-continued
FGAPVPSVQWLDEDGTTVLQDERFFPYANGTLGIRDLQANDTGRYFCLAA

NDQNNVTIMANLKVKDATQITQGPRSTIEKKGSRVTFTCQASFDPSLQPS

ITWRGDGRDLQELGDSDKYFIEDGRLVIHSLDYSDQGNYSCVASTELDVV

ESRAQLLVVGSPGPVPRLVLSDLHLLTQSQVRVSWSPAEDHNAPIEKYDI

EFEDKEMAPEKWYSLGKVPGNQTSTTLKLSPYVHYTFRVTAINKYGPGEP

SPVSETVVTPEAAPEKNPVDVKGEGNETTNMVITWKPLRWMDWNAPQVQY

RVQWRPQGTRGPWQEQIVSDPFLVVSNTSTFVPYEIKVQAVNSQGKGPEP

QVTIGYSGEDYPQAIPELEGIEILNSSAVLVKWRPVDLAQVKGHLRGYNV

TYWREGSQRKHSKRHIHKDHVVVPANTTSVILSGLRPYSSYHLEVQAFNG

RGSGPASEFTFSTPEGVPGHPEALHLECQSNTSLLLRWQPPLSHNGVLTG

YVLSYHPLDEGGKGQLSFNLRDPELRTHNLTDLSPHLRYRFQLQATTKEG

PGEAIVREGGTMALSGISDFGNISATAGENYSVVSWVPKEGQCNFRFHIL

FKALGEEKGGASLSPQYVSYNQSSYTQWDLQPDTDYEIHLFKERMFRHQM

AVKTNGTGRVRLPPAGFATEGWFIGFVSAIILLLLVLLILCFIKRSKGGK

YSVKDKEDTQVDSEARPMKDETFGEYRSLESDNEEKAFGSSQPSLNGDIK

PLGSDDSLADYGGSVDVQFNEDGSFIGQYSGKKEKEAAGGNDSSGATSPI

NPAVALE

Exemplary NCAM1 polypeptide sequences are known. For example, NCAM1 sequences are deposited as GenBank Accession Number BC047244.1 (incorporated by reference herein as present in the database on Jun. 20, 2013):

(SEQ ID NO: 2)
MLQTKDLIWTLFFLGTAVSLQVDIVPSQGEISVGESKFFLCQVAGDAKDK

DISWFSPNGEKLTPNQQRISVVWNDDSSSTLTIYNANIDDAGIYKCVVTG

EDGSESEATVNVKIFQKLMFKNAPTPQEFREGEDAVIVCDVVSSLPPTII

WKHKGRDVILKKDVRFIVLSNNYLQIRGIKKTDEGTYRCEGRILARGEIN

FKDIQVIVNVPPTIQARQNIVNATANLGQSVTLVCDAEGFPEPTMSWTKD

GEQIEQEEDDEKYIFSDDSSQLTIKKVDKNDEAEYICIAENKAGEQDATI

HLKVFAKPKITYVENQTAMELEEQVTLTCEASGDPIPSITWRTSTRNISS

EEKASWTRPEKQETLDGHMVVRSHARVSSLTLKSIQYTDAGEYICTASNT

IGQDSQSMYLEVQYAPKLQGPVAVYTWEGNQVNITCEVFAYPSATISWFR

DGQLLPSSNYSNIKIYNTPSASYLEVTPDSENDFGNYNCTAVNRIGQESL

EFILVQADTPSSPSIDQVEPYSSTAQVQFDEPEATGGVPILKYKAEWRAV

GEEVWHSKWYDAKEASMEGIVTIVGLKPETTYAVRLAALNGKGLGEISAA

SEFKTQPVQGEPSAPKLEGQMGEDGNSIKVNLIKQDDGGSPIRHYLVRYR

ALSSEWKPEIRLPSGSDHVMLKSLDWNAEYEVYVVAENQQGKSKAAHFVF

RTSAQPTAIPANGSPTSGLSTGAIVGILIVIFVLLLVVVDITCYFLNKCG

LFMCIAVNLCGKAGPGAKGKDMEEGKAAFSKDESKEPIVEVRTEEERTPN

HDGGKHTEPNETTPLTEPEKGPVEAKPECQETETKPAPAEVKTVPNDATQ

TKENENKA

Exemplary CHCL1 polypeptide sequences are known. For example, CHCL1 sequences are deposited as GenBank Accession Number AAI43497 (incorporated by reference herein as present in the database on Jun. 20, 2013):

(SEQ ID NO: 3)
MEPLLLGRGLIVYLMFLLLKFSKAIEIPSSVQQVPTIIKQSKVQVAFPFD

EYFQIECEAKGNPEPTFSWTKDGNPFYFTDHRIIPSNNSGTFRIPNEGHI

SHFQGKYRCFASNKLGIAMSEEIEFIVPSVPKFPKEKIDPLEVEEGDPIV

LPCNPPKGLPPLHIYWMNIELEHIEQDERVYMSQKGDLYFANVEEKDSRN

DYCCFAAFPRLRTIVQKMPMKLTVNSSNSIKQRKPKLLLPPTESGSESSI

TILKGEILLLECFAEGLPTPQVDWNKIGGDLPKGREAKENYGKTLKIENV

SYQDKGNYRCTASNFLGTATHDFHVIVEEPPRWTKKPQSAVYSTGSNGIL

LCEAEGEPQPTIKWRVNGSPVDNHPFAGDVVFPREISFTNLQPNHTAVYQ

CEASNVHGTILANANIDVVDVRPLIQTKDGENYATVVGYSAFLHCEFFAS

PEAVVSWQKVEEVKPLEGRRYHIYENGTLQINRTTEEDAGSYSCWVENAI

GKTAVTANLDIRNATKLRVSPKNPRIPKLHMLELHCESKCDSHLKHSLKL

SWSKDGEAFEINGTEDGRIIIDGANLTISNVTLEDQGIYCCSAHTALDSA

ADITQVTVLDVPDPPENLHLSERQNRSVRLTWEAGADHNSNISEYIVEFE

GNKEEPGRWEELTRVQGKKTTVILPLAPFVRYQFRVIAVNEVGRSQPSQP

SDHHETPPAAPDRNPQNIRVQASQPKEMIIKWEPLKSMEQNGPGLEYRVT

WKPQGAPVEWEEETVTNHTLRVMTPAVYAPYDVKVQAINQLGSGPDPQSV

TLYSGEDYPDTAPVIHGVDVINSTLVKVTWSTVPKDRVHGRLKGYQINWW

KTKSLLDGRTHPKEVNILRFSGQRNSGMVPSLDAFSEFHLTVLAYNSKGA

GPESEPYIFQTPEGVPEQPTFLKVIKVDKDTATLSWGLPKKLNGNLTGYL

LQYQIINDTYEIGELNDINITTPSKPSWHLSNLNATTKYKFYLRACTSQG

CGKPITEESSTLGEGSKGIGKISGVNLTQKTHPVEVFEPGAEHIVRLMTK

NVVGDNDSIFQDVIETRGREYAGLYDDISTQGWFIGLMCAIALLTLLLLT

VCFVKRNRGGKYSVKEKEDLHPDPEIQSVKDETFGEYSDSDEKPLKGSLR

SLNRDMQPTESADSLVEYGEGDHGLFSEDGSFIGAYAGSKEKGSVESNGS

STATFPLRA

Exemplary polypeptide sequences are known. For example, Neurofascin sequences are deposited as GenBank Accession Number O94856 (incorporated by reference herein as present in the database on Jun. 20, 2013):

(SEQ ID NO: 4)
MARQPPPPWVHAAFLLCLLSLGGAIEIPMDPSIQNELTQPPTITKQSAKD

HIVDPRDNILIECEAKGNPAPSFHWTRNSRFFNIAKDPRVSMRRRSGTLV

IDFRSGGRPEEYEGEYQCFARNKFGTALSNRIRLQVSKSPLWPKENLDPV

VVQEGAPLTLQCNPPPGLPSPVIFWMSSSMEPITQDKRVSQGHNGDLYFS

NVMLQDMQTDYSCNARFHFTHTIQQKNPFTLKVLTTRGVAERTPSFMYPQ

GTASSQMVLRGMDLLLECIASGVPTPDIAWYKKGGDLPSDKAKFENFNKA

LRITNVSEEDSGEYFCLASNKMGSIRHTISVRVKAAPYWLDEPKNLILAP

GEDGRLVCRANGNPKPTVQWMVNGEPLQSAPPNPNREVAGDTIIFRDTQI

SSRAVYQCNTSNEHGYLLANAFVSVLDVPPRMLSPRNQLIRVILYNRTRL

-continued
DCPFFGSPIPTLRWFKNGQGSNLDGGNYHVYENGSLEIKMIRKEDQGIYT

CVATNILGKAENQVRLEVKDPTRIYRMPEDQVARRGTTVQLECRVKHDPS

LKLTVSWLKDDEPLYIGNRMKKEDDSLTIFGVAERDQGSYTCVASTELDQ

DLAKAYLTVLADQATPTNRLAALPKGRPDRPRDLELTDLAERSVRLTWIP

GDANNSPITDYVVQFEEDQFQPGVWHDHSKYPGSVNSAVLRLSPYVNYQF

RVIAINEVGSSHPSLPSERYRTSGAPPESNPGDVKGEGTRKNNMEITWTP

MNATSAFGPNLRYIVKWRRRETREAWNNVTVWGSRYVVGQTPVYVPYEIR

VQAENDFGKGPEPESVIGYSGEDYPRAAPTEVKVRVMNSTAISLQWNRVY

SDTVQGQLREYRAYYWRESSLLKNLWVSQKRQQASFPGDRLRGVVSRLFP

YSNYKLEMVVVNGRGDGPRSETKEFTTPEGVPSAPRRFRVRQPNLETINL

EWDHPEHPNGIMIGYTLKYVAFNGTKVGKQIVENFSPNQTKFTVQRTDPV

SRYRFTLSARTQVGSGEAVTEESPAPPNEATPTAAPPTLPPTTVGATGAV

SSTDATAIAATTEATTVPIIPTVAPTTIATTTTVATTTTTAAATTTTES

PPTTTSGTKIHESAPDEQSIWNVTVLPNSKWANITWKHNFGPGTDFVVEY

IDSNHTKKTVPVKAQAQPIQLTDLYPGMTYTLRVYSRDNEGISSTVITFM

TSTAYTNNQADIATQGWFIGLMCAIALLVLILLIVCFIKRSRGGKYPVRE

KKDVPLGPEDPKEEDGSFDYSDEDNKPLQGSQTSLDGTIKQQESDDSLVD

YGEGGEGQFNEDGSFIGQYTVKKDKEETEGNESSEATSPVNAIYSLA

One skilled in the art will appreciate that these sequences can be altered, while still retaining the desired function. Thus in some examples the sequences used have at least 90%, at least 95%, at least 96%, at least 97%, at least 98%, or at least 99% sequence identity to SEQ ID NO: 1 (or SEQ ID NO: 2, SEQ ID NO: 3, or SEQ ID NO: 4) or a portion thereof, such as the Ig1. Ig2, Ig3, or Ig4 domains (or all 4 of these domains), the extracellular domain, or the mature L1 polypeptide. In some embodiments, the L1 polypeptide or functional fragment thereof includes or consists of the amino sequence set forth as SEQ ID NO: 1 or amino acids 20-1120 of SEQ ID NO: 1, or an amino acid sequence including at least 85% (such as at least 90%, 95%, 96%, 97%, 98, or 99%) sequence identity to the amino acid sequence set forth as SEQ ID NO: 1 or amino acids 20-1120 of SEQ ID NO: 1.

It is understood in the art that some variations can be made in the amino acid sequence of a protein without affecting the activity of the protein. Such variations include insertion of amino acid residues, deletions of amino acid residues, and substitutions of amino acid residues. These variations in sequence can be naturally occurring variations or they can be engineered through the use of genetic engineering techniques known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety. Thus, in additional embodiments, the L1 polypeptide includes one or more amino acid substitutions compared to the native L1 polypeptide (such as the polypeptide sequence set forth as SEQ ID NO: 1). For example, in some embodiments, the L1 polypeptide includes up to 20 amino acid substitutions compared to the native L1 polypeptide sequence.

In some embodiments, NCAM or functional fragment thereof is linked to an electrode. NCAM has similar (but distinct) cell adhesive activity as L1. Purification of NCAM is described in Lagenaur, C., Yip, j., and Lemmon, V. (1988) "Monoclonal 12F8 antibody identifies a subclass of N-CAM active in promotion of neurite outgrowth. Soc. Neurosci. Abstr. 14, 2253. The GenBank Accession number for human NCAM is AAH47244.1. In some embodiments, the NCAM polypeptide includes or consists of the amino sequence set forth as SEQ ID NO: 1, or an amino acid sequence including at least 85% (such as at least 90% or 95%) sequence identity to the amino acid sequence set forth as SEQ ID NO: 1.

Standard methods in the art can be used to produce the L1 polypeptide or functional fragment thereof or variant or homologue thereof. For example, recombinant DNA technology can be used to generate a nucleic acid encoding the L1 polypeptide, from which the peptide can be expressed and purified. Typically, the nucleic acid encoding the L1 polypeptide is expressed in eukaryotic cells.

In some embodiments the L1 polypeptide is purified from neural tissue (e.g., brain tissue) using immunoaffinity chromatography, for example, as described in Lagenaur and Lemmon, V, *An L1-like molecule, the 8D9 antigen is a potent substrate for neurite extension*. Proc. Natl. Acad. Sci. USA, 1987. 84: p. 7753-7757, the disclosure of which is incorporated by reference herein in its entirety. The term purified does not require absolute purity; rather, it is intended as a relative term. Thus, for example, a purified L1 polypeptide preparation is one in which the L1 polypeptide is more enriched than the L1 polypeptide is in its natural environment within a cell. In one embodiment, a L1 polypeptide preparation is purified such that the L1 polypeptide represents at least 50% (such as at least 60, 70, 80, or 90%) of the total polypeptide content of the preparation.

A polypeptide is a polymer of amino acid residues that are joined together through amide bonds. The amino acids included in a polypeptide can be subject to post-translational modification (e.g., glycosylation, sulfation or phosphorylation), and "polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

In other embodiments, the L1 polypeptide or functional fragment can be produced using recombinant DNA methodologies, e.g., by expressing a nucleic acid molecule encoding a recombinant L1 polypeptide in a host cell, and purifying the L1 polypeptide. Nucleic acid molecules encoding the L1 polypeptide or a fragment thereof provided herein can readily be produced by one of skill in the art. For example, these nucleic acids can be produced using the amino acid sequences provided herein, sequences available in the art, and the genetic code.

L1 polypeptides and functional fragment thereof are provided above. One of skill in the art can readily use the genetic code to construct a variety of nucleic acid molecules encoding the L1 polypeptide or a fragment thereof, including functionally equivalent nucleic acids, such as nucleic acids which differ in sequence but which encode the same polypeptide, or encode a fusion protein including the polypeptide and another protein.

Nucleic acid sequences encoding the L1 polypeptide or functional fragment thereof can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 500 bases, longer sequences can be obtained by the ligation of shorter sequences.

Exemplary nucleic acids can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

Any of the nucleic acids encoding any of the polypeptides disclosed herein (or fragment thereof) can be expressed in a recombinantly engineered cell such as bacteria, plant, yeast, insect and mammalian cells. In some embodiments, the polypeptides can be expressed as a fusion protein. The nucleic acid sequences can optionally encode a leader sequence.

It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the disclosed L1 polypeptide or functional fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

The expression of nucleic acids encoding the L1 polypeptide or functional fragment thereof can be achieved by operably linking the DNA or cDNA to a promoter (which is either constitutive or inducible), followed by incorporation into an expression cassette. The promoter can be any promoter of interest, such as a cytomegalovirus promoter. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

Once expressed, the polypeptides can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The polypeptides need not be 100% pure. Once purified, partially or to homogeneity as desired, if to be used therapeutically, the polypeptides should be substantially free of endotoxin.

Methods for expression of polypeptides and/or refolding to an appropriate active form, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

D. Polypeptide Conjugation

In several embodiments, an effective amount of L1 polypeptide or functional fragment thereof can be conjugated to the exterior surface of a neural probes for recording and/or stimulating a neural signal, for example by conjugation to the exterior surface of the insulating layer included on the neural probe. In some embodiments, the probe includes a parylene C insulating layer on its exterior surface, and the L1 polypeptide or functional fragment thereof is conjugated to the exterior surface of the parylene C insulating layer. Methods of conjugating (e.g., covalently bonding one molecule to another) a polypeptide to the surface of a neural probe, or the surface of an insulating layer (such as an insulating layer including parylene C) are known in the art, and are further described herein.

For example, for probes including a silicon oxide insulation layer on their exterior surface, silane chemistry and a GMBS crosslinker may be used to covalently attach the L1 polypeptide or functional fragment thereof to the exterior of the insulation layer (see, e.g., Azemi et al., Acta Biomaterialia, 2008. 4(5): p. 1208-1217, which is incorporated by reference herein).

Additionally, several coating strategies to immobilize proteins on a parylene C surface have been developed. A first approach utilizes air plasma to modify the parylene C surface with polar hydroxyl groups at the surface (see, e.g., Chang et al., Langmuir, 2007. 23(23): p. 11718-25; and Sia and Whitesides, Electrophoresis, 2003. 24(21): p. 3563-76, each of which is incorporated by reference herein in its entirety). The probes are then soaked in a protein solution containing the L1 polypeptide or functional fragment thereof (e.g., a solution with 50-150 µg/mL L1) for about 1 hour. The successful attachment of the desired protein may be characterized using known methods, for example immunostaining and the bioactivity of the bound protein can be verified in cell culture (see, e.g., Kolarcik et al., Acta Biomater, 2012. 8(10): p. 3561-75, which is incorporated by reference herein in its entirety).

Figures 15A, 15B:
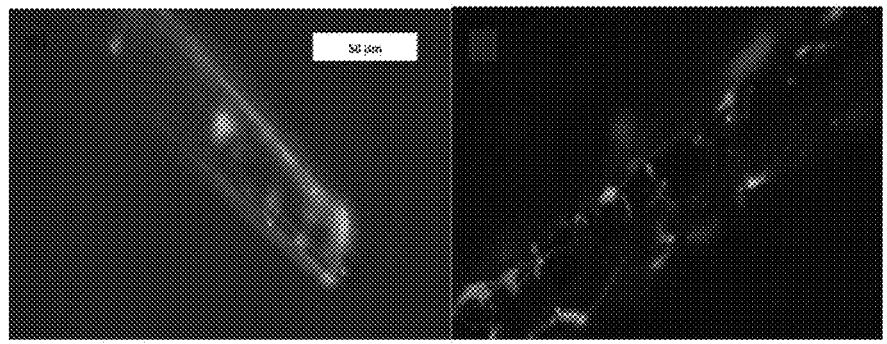
FIGS. 15A-15F show a series of immunofluorescence images, schematic diagrams and a graph illustrating L1 coating on parylene C coated neural probes. (A) Green fluorescent antibody staining verifying the protein presence on the microwire probe. (B) Neurons growing on L1 coated microwire shown by staining of β-tubulin (green) and nuclei (DAPI, blue). (C) Quantification of different cell attachment and (D) neurons growing on L1 coated parylene C surfaces that were pre-soaked in media at physiological condition for 5 days, the L1's biological effect is reserved. (E) Illustration of a first approach for covalently attaching L1 to the neural probe where carboxylic acid groups are created followed by protein/peptide binding. (F) Illustration of an additional approach for covalently attaching L1 to neural probes where reactive parylene is created with amine groups for protein binding.
Figure 15C:
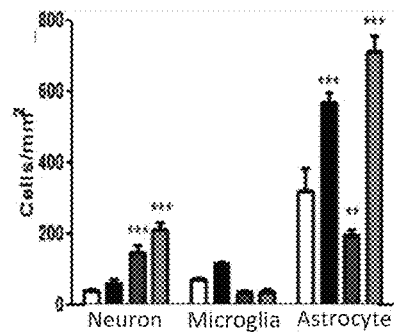
Figure 15D:
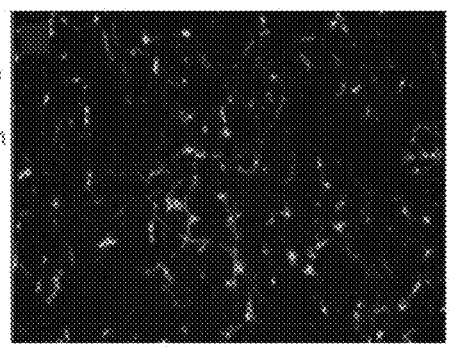
Figure 15E:
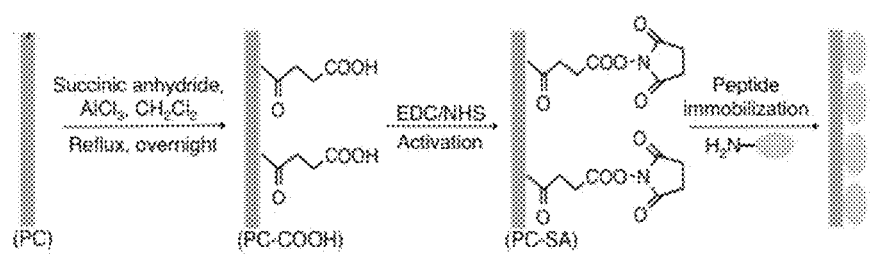

Additional methods have also been developed for conjugation of proteins to parylene C surfaces. For example, surface treatment of a parylene C coated neural probe with succinic anhydride adds carboxylic acid groups on the exterior surface of the probe, which can then react with amine on proteins (see, e.g., FIG. 15E) (see, e.g., Zhang et al., Acta Biomater, 2011. 7(10): p. 3746-56, which is incorporated by reference herein in its entirety). Another method involves the synthesis of diamino(2.2)paracyclophane by nitration of (2.2)paracyclophane and subsequent reduction of the nitro groups. The diamino(2,2)paracyclophane can then form a parylene coating in a CVD chamber which has amine groups available for protein binding (see FIG. 2F; and Lahann et al., Angew Chem Int Ed Engl, 2001. 40(16): p. 2947, which is incorporated by reference herein in its entirety).

Figures 16A, 16B:
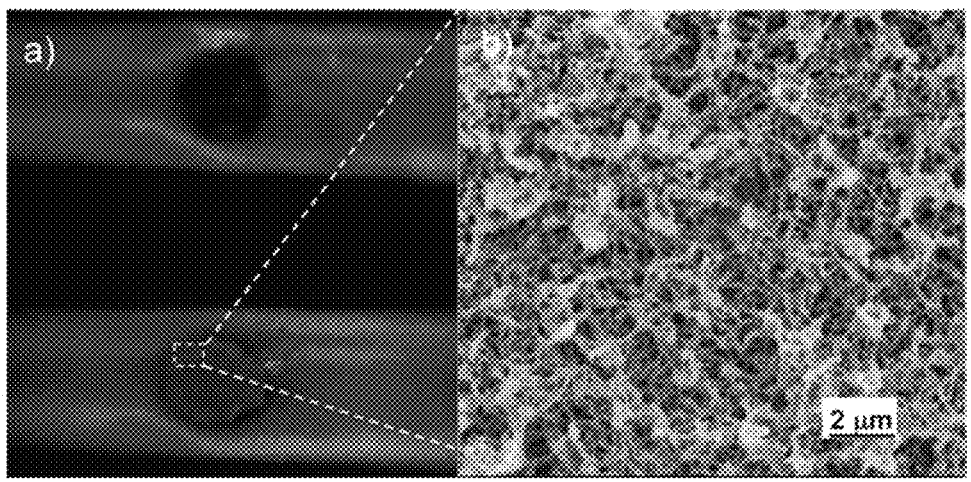
FIGS. 16A-16D illustrate the coating of an electrode site with conductive polymer functionalized with biomolecules for attracting neuronal growth to the neural electrodes. (A) Polyethylenedioxythiophene (PEDOT) coating doped with L1 on the bottom electrode, anti-L1 staining (red) showed that presence of L1 on the PEDOT coating by the red fluorescence. (B) Scanning Electron Microscopy (SEM) of PEDOT/L1, (C) scheme of PEDOT/GO functionalization and (D) PEDOT/GO functionalized with neuroadhesive peptide promoted neuron attachment (β-tubulin III, green and nuclei (DAPI), blue staining is shown).
Figures 16C, 16D:
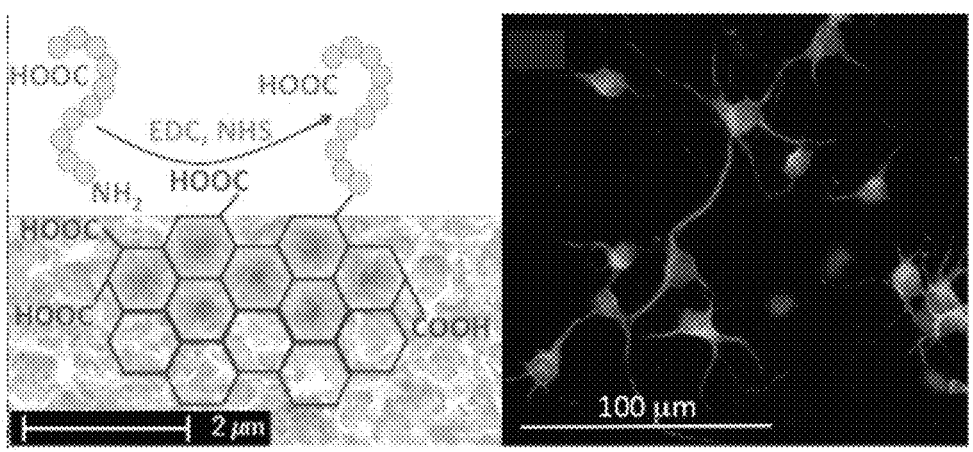

In some embodiments, the L1 polypeptide or functional fragment thereof can be conjugated to a conductive surface of an electrode included on the neural probe, such as an exterior surface of the electrode, for example to promote neuronal attachment as close as possible to the conductive surface of the electrode. For example, the L1 polypeptide may be conjugated to the conductive surface of the electrode using direct co-deposition of conducting polymer and L1 on conductive sites on the electrode (see, FIGS. 16A-16B). In further embodiments, L1 polypeptide can be conjugated to the conductive surface of the electrode using polyethylenedioxythiophene (PEDOT) doped with graphene oxide (GO), which can then be covalently linked to protein via carboxylic acid groups on GO (see FIGS. 16C-16D). Methods of conjugating polypeptides to conductive surfaces of an electrode are described, e.g., in Luo et al., J Mat. Chem. B, 2013. 1(1): p. 1340-1348, which is incorporated by reference herein in its entirety.

In additional embodiments, the L1 polypeptide or functional fragment can be covalently attached to the carboxyl functional groups of poly(acrylic acid) (PAA) and lightly cross-linked (e.g., with EDC chemistry), resulting in a stable and soluble L1-polymer conjugate. For silicon oxide substrates, the L1-polymer conjugate can then be covalently attached to the silicon oxide surface using traditional silanization/GMBS methods as described herein. For parylene C substrates, the L1-polymer conjugate can be conjugated to a parylene C coated probe after that probe is treated with plasma oxygen (as described herein), or crosslinked to the exterior surface of a parylene C coated probe via EDC/NHS cross-linking after that probe is treated with plasma oxygen.

The probes and devices can be stored before use as needed. In some embodiments, a probe or device including an L1 polypeptide or functional fragment thereof on its exterior surface can be freeze-dried following conjugation of the L1 polypeptide or functional fragment to increase storage shelf-life. The probe cab then be maintained at freezing temperatures (e.g., −20° C.) in the presence of desiccant as needed, after which the probe can be rehydrated with sterile PBS prior to use. In additional embodiments, prior to freeze-drying, probe can be treated with a cross-linking agent (e.g., free radical oxidation using superoxide), to crosslink L1 polypeptide or the functional fragment thereof, to increase the stability (and shelf-life) of the L1 polypeptide or functional fragment.

In additional embodiments, a protective coating composed of layer-by-layer-deposited mannitol and polyelectrolytes can be used to seal the prepared L1-coated probe to improve stability prior to storage (or freeze-drying). Stored L1 coated probes can then be rehydrated with sterile PBS to dissolve the protective coating. Alternatively, polyethylene glycol gel may be applied to preserve the bioactivity of the underlying protein upon freeze-drying and storage.

E. Recording and/or Stimulating Neural Signals

In several embodiments, a disclosed probe (or device including the probe) can be used for chronic recording and/or stimulation of neural signals from a subject. For example the probe (or device including the probe) can be implanted into neuronal tissue of the subject, and used to record and/or stimulate neural signals from the subject for a period of at least 1 month (such as at least 2, 6, 12, 18, 24, 30 or 36 or more months) without deterioration of quality or quantity of the recorded or stimulated neural signal. In several such embodiments the probe includes a parylene C insulating layer, the exterior surface of which is conjugated to an L1 polypeptide or functional fragment thereof as disclosed herein.

Methods and systems for implanting probes into neuronal tissue of a subject (e.g., central neuronal tissue such as the brain or spinal cord, or peripheral neuronal tissue, such as the dorsal root ganglia) are known to the person of ordinary skill in the art, and further described herein. Further, methods and systems for recording and/or stimulating neural signals from an probe implanted in neuronal tissue in a subject are known.

As illustrated herein, using neural probes that lack L1, a recording increase (quality and yield) is expected over the first few weeks after the probe is implanted into neuronal tissue of a subject. Without being bound by theory, this initial increase (lasting a few weeks) is believed to be due to recovery of tissue from insertion trauma. After the initial increase the recording quality stabilizes and eventually begins to decrease at longer time points. In contrast, using the disclosed probes that include an effective amount of L1 polypeptide or functional fragment thereof on their exterior surface, an increase in neural signal that continues for several months (e.g., at least 2 (such as at least 3, 4, 5, 6, 7, 8, 9, 10, 11, 12, 13, 14, 15, 16, 17, 18, 24, 30, 36, or more months) was recorded. Furthermore, using probes including the L1 or functional fragment, an increased number of sortable units per channel and higher amplitude of signal is possible compared to probes without L1.

In some embodiments use of the disclosed probe (or device including the probe) allows for an increase in the recorded neural signal over time. For example, in some embodiments, use of the disclosed probe (or device including the probe) allows for an increase in the total number of sortable neural units over time; for example, an increase of at least 10%, 20%, 30%, 40%, 50%, 60%, 70%, 80%, 90%, or 100% or more of an increase in total number of sortable neural recording units over time. In some embodiments, use of the disclosed probe (or device including the probe) allows for an increase in the average number of sortable neural units per channel of the probe over time; for example, an increase of at least 10%, 20%, 30%, 40%, 50%, 60%, 70%, 80%, 90%, or 100% or more of an increase in the average number of sortable neural recording units per channel of the probe over time. In some embodiments the increase over time is measured at 4 weeks post implantation compared to 20 weeks post implantation.

Methods of identifying neural recording units in data recorded from an electrode (or array of electrodes) implanted in a subject are known to the person of ordinary skill in the art (see, e.g., Lewicki, "A review of methods for spike sorting: the detection and classification of neural action potentials," Network: Comput. Neural Syst., 9, R53-R78, 1998, which is incorporated by reference herein in its entirety). In some embodiments, raw neural recording data is first band passed filtered between 300 Hz to 10 kHz. Following data filtering, waveforms that cross the TDT automatic threshold are selected for further spike sorting analysis. Hoop-based spike discrimination is carried out online as the experimenter selects time-voltage windows based on waveform shape. Waveforms that fall within this selected window are classified as belonging to the same sort. Manual inspection of the sorted units in principal component analysis space is used to assess the appropriateness of the selected windows. Online spike sorting progresses by relying upon template matching to properly sort units that fall into one of the above mentioned time-voltage windows.

The probe and/or device is typically linked to circuitry for recording and/or stimulating a neural signal via the one or more electrodes included on the probe. The person of ordinary skill in the art is familiar with circuitry for use with the disclosed devices. In some embodiments, the integrated circuits can be fully implanted (typically implantable in a subcutaneous pocket within a patient's body) or partially implanted in the patient, but are not limited thereto. The operable linkage to the probe or device can be by way of one or more leads, although any operable linkage capable of transmitting the measured neural signal from the electrodes to the circuitry, or a stimulation signal from the circuitry to the electrodes, can be used.

In some embodiments, the integrated circuitry includes a stimulator linked to the device and suitably designed for application of various current, voltage, pulse rate, waveforms etc., for generating a neural signal in one or more neurons in proximity to the electrode or electrodes included on the device. For example, the stimulator can be separate from the integrated circuitry or it can be included in the same housing as the integrated circuitry.

EXAMPLES

The following examples are provided to illustrate particular features of certain embodiments, but the scope of the claims should not be limited to those features exemplified.

Example 1

In Vivo Effects of L1 Coating on Inflammation and Neuronal Health at the Electrode/Tissue Interface in Rat Spinal Cord and DRG The example illustrates use of L1 coated neural probes for improved recording of neural signals over time.

Abstract. The spinal cord and dorsal root ganglion (DRG) are target implantation regions for neural prosthetics, but the tissue-electrode interface in these regions is not well-studied. To improve understanding of these locations, the tissue reactions around implanted electrodes were characterized. L1, an adhesion molecule shown to maintain neuronal density and reduce gliosis in brain tissue, was evaluated in spinal cord and DRG implants. Following L1 immobilization onto neural probes, the bioactivities of the coatings were verified in vitro using neuron, astrocyte and microglia cultures. Non-modified and L1-coated probes were implanted into adult rats for 1 or 4 weeks. Hematoxylin and eosin staining along with cell-type specific antibodies were used to characterize the tissue response. In the spinal cord and DRG, cells aggregated at the electrode-tissue interface. Microglia staining was more intense around the implant site and decreased with distance from the interface. Neurofilament staining in both locations was decreased or absent around the implant when compared to surrounding tissue. With L1, neurofilament staining was significantly increased while neuronal cell death decreased. The results indicate that L1-modified probes may result in an improved chronic neural interface and will be evaluated in recording and stimulation studies.

Introduction. Neural prosthetic devices implanted into the nervous system to bypass and/or restore sensory-motor or cognitive functions have enormous clinical potential. There are a variety of situations in which such devices can be of use with proposed applications in the fields of gerontology, rehabilitative medicine, psychiatry, neurology and clinical research (Rothschild, *Front Neuroeng*, 3:112, 2010). More specifically, neural interface systems (NIS) can be used for communication (Ryu and Shenoy, *Neurosurg Focus*, 27:E5, 2009), to restore lost functional movement (Song et al., *Conf Proc IEEE Eng Med Biol Soc*, 2007:445-8, 2007), to reinnervate target locations for bladder control and for the treatment of neurological conditions like epilepsy (Morrell, *Curr Opin Neurol*, 19:164-8, 2006; Skarpaas and Morrell, *Neurotherapeutics*, 6:238-43, 2009) and Parkinson's Disease (Pena et al., *IEEE Trans Neural Syst Rehabil Eng*,15: 421-4, 2007) among others. While much effort has been devoted to brain interfaces, both the spinal cord and DRG are target implantation regions for these promising rehabilitative and therapeutic devices as well. For example, spinal cord stimulation has been investigated for pain control (Waltz, *Stereotact Funct Neurosurg*, 69:288-99, 1997) and restoration of motor functions (Mushahwar et al., *IEEE Trans Neural Syst Rehabil Eng*, 10:68-81, 2002; Moritz et al., *J Neurophysiol*, 97:110-20, 2007), while the DRG is an attractive site for recording or stimulating primary afferent neurons to provide sensory feedback (Weber et al., *J Neural Eng*, 4:S168-80, 2007; Gaunt et al., *J Neural Eng*, 6:055009, 2009).

Irrespective of the implant location, these neural interfaces must remain stable throughout the lifespan of the user. However, biocompatibility issues have limited the success of chronically implanted devices (Schwartz, *Annu Rev Neurosci*, 27:487-507, 2004; Schwartz et al., *Neuron*, 52:205-20, 2006; Cheung, *Biomed Microdevices*, 9:923-38, 2007; Polikov et al., *J Neurosci Methods*, 148:1-18, 2005). The fate of implanted devices is often determined by the effective integration with the surrounding neural tissue, a current and major roadblock in neuroengineering (Rothschild, *Front Neuroeng*, 3:112, 2010; Rao and Winter, *Front Neuroeng*, 2:6, 2009; Straley and Heilshorn, *Front Neuroeng*, 2:9, 2009; Grill et al., *Annu Rev Biomed Eng*, 11:1-24, 2009). In brain tissue, immune and inflammatory reactions including gliosis at the implant site result in decreased performance of microelectrodes. Gliosis is thought to be mediated by macrophages, activated microglia and reactive astrocytes resulting in the formation of a glial sheath that can encapsulate and isolate the implanted probe from the surrounding tissue (Azemi et al., *Acta Biomater*, 4:1208-17, 2008). In addition, significant decreases in neuronal density in the area immediately surrounding the implant site (the "kill zone") are problematic. In the peripheral system, manipulation or damage to a neural structure also leads to anatomic, metabolic and physiological alterations (Panetsos et al., *IEEE Trans Neural Syst Rehabil Eng*, 16:223-32, 2008). However, the reactions surrounding these peripheral interfaces highlight the potential for nerve regeneration and recovery following initial damage (Panetsos et al., *IEEE Trans Neural Syst Rehabil Eng*, 16:223-32, 2008; Pardue et al., *Exp Eye Res*, 73:333-43, 2001; Lago et al., *IEEE Trans Biomed Eng*, 54:1129-37, 2007). Although valuable for multiple applications, the spinal cord and DRG are less well-studied than the brain and peripheral nerve.

Surface modifications of implanted electrodes are one approach used to promote favorable interactions between the neural implants and neural cells, and a variety of biomaterial designs have been investigated (Ryu and Shenoy, *Neurosurg Focus*, 27:E5, 2009; Rao and Winter, *Front Neuroeng*, 2:6, 2009). L1, a transmembrane cell surface glycoprotein, mediates cell-cell recognition by interacting with L1 molecules on the surfaces of neighboring cells ("hemophilic interactions") or with non-L1 molecules on the surfaces of these cells ("heterophilic interactions") (Maness and Schachner, *Nat Neurosci*, 10:19-26, 2007; Figge et al., *Mol Cell Neurosci*, 49:196-204, 2011). It is one of the molecular cues that promotes neurite outgrowth (Lemmon et al., *Neuron*, 2:1597-603, 1989; Lagenaur and Lemmon, *Proc Natl Acad Sci USA*, 84:7753-7, 1987) thereby contributing to the formation of the complex neuronal connections of the nervous system (Figge et al., *Mol Cell Neurosci*, 49:196-204, 2011). It is also involved in neuronal migration and synaptic plasticity with essential roles in the maintenance of nervous system functions (Maness and Schachner, *Nat Neurosci*, 10:19-26, 2007; Kenwrick et al., *Hum Mol Genet*, 9:879-86, 2000).

Materials and Methods

Neural Probes and Surface Modification. Standard tip tungsten microelectrodes (MicroProbes, Gaithersburg, Md.) were used for both in vitro experiments and in vivo implants. Each microelectrode was cut to a 3 mm length for chronic insertion into the neural tissue. The shaft diameter of these tips was approximately 0.081 mm (with a parylene-C coating of 3 μm) and an exposed tip diameter of 1-2 μm (25:1 taper).

L1 protein was purified from brain tissue as described previously (Azemi et al., *Acta Biomater*, 4:1208-17, 2008; Lagenaur and Lemmon, *Proc Natl Acad Sci USA*, 84:7753-7, 1987, each of which is incorporated by reference herein in its entirety) and concentrations determined using the FluoroProfile (Sigma-Aldrich, St. Louis, Mo.) epicocconone-based reagent kit (Mackintosh et al., *Proteomics*, 5:4673-7, 2005) using bovine serum albumin (BSA; Sigma-Aldrich) standards. All coating experiments were carried out in a sterile environment at room temperature. A two-step approach similar to that used by Musalla and colleagues was utilized (Musallam et al., *J Neurosci Methods*, 160:122-7, 2007). More specifically, parylene-C-insulated microwires were treated with plasma for 10 seconds. Then two different protein solutions, L1 (100 μg/mL) or laminin (40 μg/mL, Sigma-Aldrich), were added onto the parylene-C/plasma-modified surfaces for 1 hour at 4° C. The coating conditions included the following: 1.) untreated parylene-C, 2.) parylene-C+plasma treatment, 3.) parylene-C+plasma treatment+L1 and 4.) parylene-C+plasma treatment+laminin.

Neural probes for the in vivo studies were sterilized with ethylene oxide (EtO). The L1 group was treated with plasma for 10 seconds on each side and L1 deposited as described above for 1 hour at 4° C. The resulting L1-immobilized probes were rinsed with phosphate buffered saline (PBS, pH 7.4) and stored at 4° C. in sterile PBS until implantation. The L1 coating was performed the same day of the implantation.

Cell Culture. L1 immobilization was confirmed by staining with the 5H7 L1 monoclonal primary antibody and fluorophore-conjugated secondary antibody as described (Azemi et al., *Acta Biomater*, 4:1208-17, 2008). The stability of the coatings was tested at two time points. For the day 0 time point, cells were plated on the same day as the coating was applied. For the day 5 time point, cells were added to the coated surface 5 days after the coating had been soaked in Dulbecco's Modified Eagle Medium (DMEM) without serum at 37° C. and 5% $CO_2$.

Rat cortices from embryonic day 18 (E18) Sprague-Dawley rats were obtained from BrainBits, LLC (Springfield, Ill.) and neuronal cultures prepared as described by Brewer and colleagues (Brewer, *J Neurosci Res*, 42:674-83, 1995). Cells were resuspended in neurobasal base media (Invitrogen, Carlsbad, Calif.) supplemented with B27 (Invitrogen), glutamine (Sigma-Aldrich) and glutamate (Sigma-Aldrich). Cells were plated on surface-modified parylene-C at a density of $1.5 \times 10^5$ cells/cm$^2$ and maintained in culture for 3 days at 37° C. and 5% $CO_2$.

Astrocyte-enriched cultures were prepared as described previously (Azemi et al., *Acta Biomater*, 4:1208-17, 2008). Briefly, rat cortices were digested with trypsin and the resulting cell suspension maintained in DMEM (Invitrogen) supplemented with 10% fetal calf serum (FCS; Thermo Scientific, Pittsburgh, Pa.) at 37° C. and 5% $CO_2$. Glial cells were passaged weekly for up to 4 weeks. For surface modification experiments, glial cells were trypsinized, resuspended in DMEM/10% FCS and plated at a density of $1.5 \times 10^5$ cells/cm$^2$. Astrocytes were subsequently cultured for 2 days prior to fixation.

Highly Aggressively Proliferating Immortalized (HAPI) cells (Cheepsunthorn et al., *Glia*, 35:53-62, 2001) were kindly provided by Dr. Xiaoming Hu, Department of Neurology, University of Pittsburgh and cultured as described previously (Luo et al., *Biomaterials*, 32:6316-23, 2011). Briefly, HAPI cells were maintained in DMEM/F12 lacking HEPES and Phenol Red (Invitrogen) supplemented with L-glutamine (Sigma-Aldrich) and 10% fetal bovine serum (FBS; Thermo Scientific). After thawing, cells were passaged once prior to plating at a density of $1 \times 10^5$ cells/cm$^2$ and incubated for 24 hours at 37° C. and 5% $CO_2$ before fixation.

Prior to immunohistochemical labeling, cells were fixed with 4% paraformaldehyde (PFA; Sigma-Aldrich) for 10 minutes. After blocking for 45 minutes with 4% goat serum in phosphate buffered saline (PBS), monoclonal antibodies for neuronal class III β-tubulin (2 µg/mL; Invitrogen), glial fibrillary acidic protein (0.4 µg/mL; GFAP; DakoCytomation, Carpinteria, Calif.) and ED1 (4 µg/mL; Fisher Scientific, Pittsburgh, Pa.) were added for 1 hour at room temperature. After washing with PBS, fluorescence-conjugated secondary antibodies were added for 1 hour. Cell nuclei were stained with Hoechst 33258 (2 µg/mL; Sigma-Aldrich) in PBS. Ten samples for each coating condition were used for each experiment and experiments were repeated at least three times.

Digital images of the stained cells were taken using a fluorescence microscope (Zeiss Axioskop, Zeiss, USA). Neuronal attachment was determined by counting the number of neurons that showed co-localization of class III β-tubulin and Hoescht and had at least one neurite longer than the cell body dimensions. Astrocyte attachment was determined for cells that showed co-localization of GFAP and Hoescht. Microglia attachment was determined by the co-localization of ED1 and Hoescht. The entire probe was imaged and all cells on the surface of the probes were counted by a non-objective examiner. The cell number was reported by dividing the total number of cells by the projected surface area. Statistical analyses were performed using GraphPad Prism 5 (GraphPad Software, Inc., La Jolla, Calif.). Comparisons involving multiple groups were accomplished using two-way analysis of variance (ANOVA) followed by Bonferroni post-hoc analysis. A p value ≤0.05 was considered statistically significant.

Surgical Procedure. All surgical procedures were done in accordance with those outlined by the United States Department of Agriculture and approved by the Institutional Animal Care and Use Committee of the University of Pittsburgh. Animals were housed in the facilities of the University of Pittsburgh Department of Laboratory Animal Resources and given free access to food and water.

Twenty-four adult male Sprague-Dawley rats (300±50 g) were used throughout this study. Three or four animals per time point were implanted in the spinal cord and/or DRG with either non-modified or L1-coated microelectrode tips (outlined in Table 2). Both 1 week and 4 week time points were investigated in an effort to characterize the acute (1 week) and chronic (4 weeks) tissue responses.

Animals were anesthetized with 2.5% isofluorane in oxygen at 1 L/min for 5 minutes prior to surgery and then maintained for the duration of the procedure with 1-2% isofluorane. Anesthesia level was closely monitored during the procedure by observing changes in respiratory rate, heart rate, body temperature and absence of the pedal reflex. Ophthalmic ointment was applied to the eyes while animals were under anesthesia.

Animals were placed in a stereotaxic frame and the hair over the incision site removed. The skin was disinfected with isopropyl alcohol and betadine and a sterile environment maintained throughout the procedure. The lumbar spine was exposed through a dorsal midline incision using surgical elevators to clear soft tissue from bone. A unilateral laminectomy exposed the left side of the lumbar spinal cord and DRG. Every attempt was made to minimize removal and/or cutting of muscles and bone surrounding the area of implant. Once exposed, non-modified or L1-coated probes (~3 mm length) were inserted (1-4/spinal cord and 1-2/DRG) under a surgical microscope using a micromanipulator equipped with a vacuum tool; probes were held in place with the vacuum tool, positioned by moving the micromanipulator and then lowered into place. After the muscle and skin were sutured, the animal recovered under close supervision in the surgical procedure room. Rats were monitored closely for signs of pain or distress and post-operative pain managed with buprenorphine (0.3 mg/kg). The same surgeon performed all surgeries to minimize variability associated with the surgery and probe implantation.

Tissue Preparation and Immunofluorescence. At the designated time points, animals were anesthetized with a ketamine/xylazine cocktail (100/20 mg/kg) via the intraperitoneal (IP) cavity. Animals were then transcardially perfused with cold (4° C.) PBS followed by 4% (w/v) PFA in PBS. The spinal cord/DRG tissue was removed, post-fixed for up to 3 days and then equilibrated in 30% sucrose. Dissected tissue was then cryoprotected using the optimal cutting temperature (OCT) compound (Tissue-Tek, Torrance, Calif.). Serial sections were cut at a 10 μm thickness.

Monoclonal antibodies were used to detect neurofilament 200 kD (NF200; Millipore, Billerica, Mass.), vimentin (Clone V-9; Millipore) and neuronal nuclei (NeuN; Millipore). Polyclonal antibodies were used to detect Iba1 (Wako Chemicals USA, Inc., Richmond, Va.), glial fibrillary acidic protein (GFAP; DakoCytomation) and cleaved caspase-3 (Asp175; Cell Signaling Technology, Boston, Mass.). These antibodies were used at a dilution of 1:500 (NF200, Iba1, Vimentin, GFAP, NeuN) or 1:50 (cleaved caspase-3) and the appropriate fluorescence-conjugated antibody used at a dilution of 1:500.

Tissue sections were stained at the same time for each antibody/antibody pair to minimize variability. Hematoxylin and eosin (H and E) staining along with markers to visualize mature axons (NF200), microglia (Iba1), astrocytes/fibroblasts/endothelial cells (vimentin), astrocytes (GFAP), neuronal nuclei (NeuN) and cell death (cleaved caspase-3) (antibodies outlined in Table 3) were used.

Tissue sections were hydrated in PBS and non-specific binding blocked with 0.5% BSA. Primary antibodies were then diluted in BSA and added for approximately 1 hour. After washing with BSA, fluorophore-conjugated secondary antibodies (goat anti-mouse Alexa Fluor 488 and goat anti-rabbit Alexa Fluor 594) diluted in BSA were added for approximately 1 hour and Hoescht used as the nuclear stain. Fluoromount-G (Southern Biotechnology Associates, Birmingham, Ala.) was used for mounting and to preserve fluorescence. Negative controls lacking primary antibody were included for each secondary antibody.

Quantitative Tissue and Statistical Analyses. Confocal fluorescent microscopy was used to evaluate the cellular reactions associated with the implanted probes. Images were acquired using an Olympus Fluoview 1000 I Confocal Microscope (Olympus America, Center Valley, Pa.) at the Center for Biologic Imaging at the University of Pittsburgh. For each antibody, images were acquired using the same exposure time and in a single session to reduce variability during data analysis. Images were centered on the implant site and multiple images acquired. Images were also taken at a significant distance from the implant and used to define the average background staining intensities for each stain on every tissue sample.

For quantification of NF200 staining, custom MATLAB software (MathWorks, Boston, Mass.) was used to determine the size of the kill zone. More specifically, the perimeter of each implant site was defined using the corresponding DAPI-stained image and the NF200-stained image used to identify the presence of NF200 staining (indicative of intact neuronal processes). The size of the kill zone was then calculated in 10° bins around the 360° perimeter of the implant site by subtracting the location of the implant site from the location of NF200 staining. These 36 distance measures were used to calculate the mean kill zone size and compared via the rank sum test.

For quantification of Iba1 and GFAP staining, DAPI-stained images were again used to determine the perimeter of the implant site. Threshold values based on 95% of the background staining for each section were established. The amount of staining above this threshold value was then quantified and reported as a function of distance from the implant site. The median intensity values were binned every 50 μm from the implant site and compared via the rank sum test.

For NeuN/caspase-3 stained images, the number of NeuN/caspase-3 positive cells was quantified and reported as a percentage of the total number of NeuN positive cells.

Comparisons between any two groups of data were accomplished using the unpaired t test at the 95% confidence interval. A p value ≤0.05 was considered statistically significant.

Results

In Vitro Studies. determine if the L1 coating could increase neuronal density and decrease gliosis, the cellular attachment of neurons, astrocytes and microglia for different surface conditions were quantified and compared (FIG. 1). Parylene-C insulated probes were selected as the implant model because a number of widely used neural electrode arrays include parylene-C as an insulator. A two-step approach to immobilize proteins onto the parylene-C surface was used. Plasma treatment was first used to provide a charged polar group at the surface to facilitate protein binding. Protein was then adsorbed onto the activated surface. The effectiveness of protein immobilization was verified by testing the cellular response in culture. In comparison to the uncoated probes, a higher number of neurons were observed on the L1- and laminin-coated probes while there were fewer activated microglia (FIG. 1). L1 is a neuron-specific adhesion molecule that promotes growth and adhesion via hemophilic binding while laminin is an extracellular matrix protein that binds to multiple cells types via the integrin receptors. Therefore, the coating method was effective in immobilizing proteins and maintaining their respective biological functionality. In addition, the cellular responses associated with wires coated with the proteins and soaked in media for 5 days were similar to those observed with freshly-coated wires indicating good coating stability. As the L1-coated microwires demonstrated the desired properties for an improved neural tissue interface in vitro, this surface modification for subsequent in vivo work.

Figure 2A:
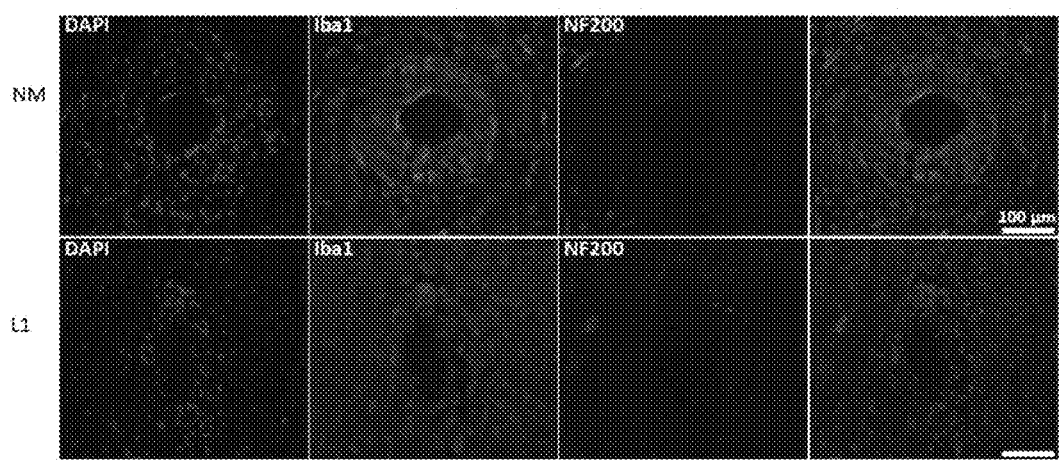
FIGS. 2A and 2B show a set of immunofluorescence images illustrating neurofilament 200 kD (NF200; red; a neuronal cell marker) and Iba-1 (green; a non-neuronal cell marker) expression in the spinal cord following implant of non-modified (NM) and L1-coated neural probes. NF200 staining was lacking in the area immediately surrounding the implant site and differences were assessed by measuring the size of the area void of this staining. Iba1-positive cells were localized around the implant site and this immunoreactivity quantified and compared. (A) Representative images at the 1 week (or acute) time point. (B) Representative images at the 4 week (or chronic) time point. Scale bars represent 100 μm.
Figure 2B:
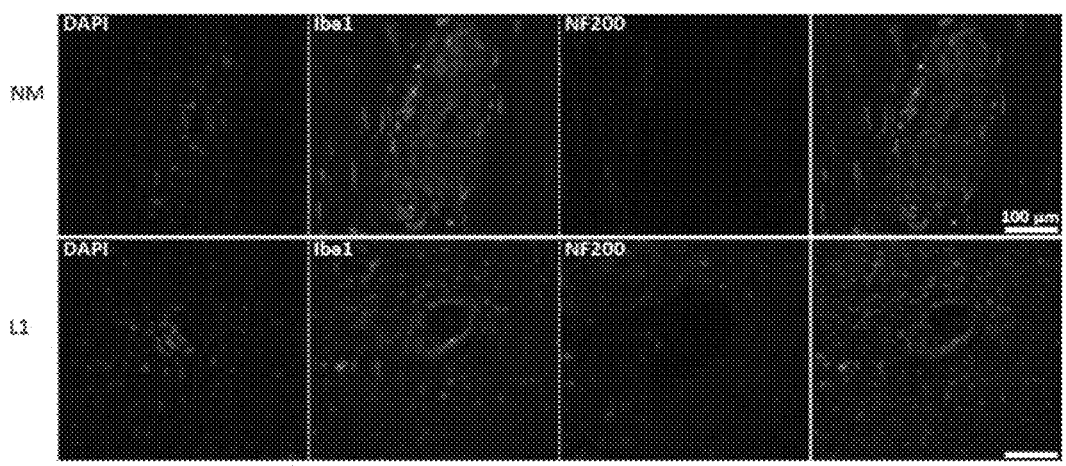
Figure 3:
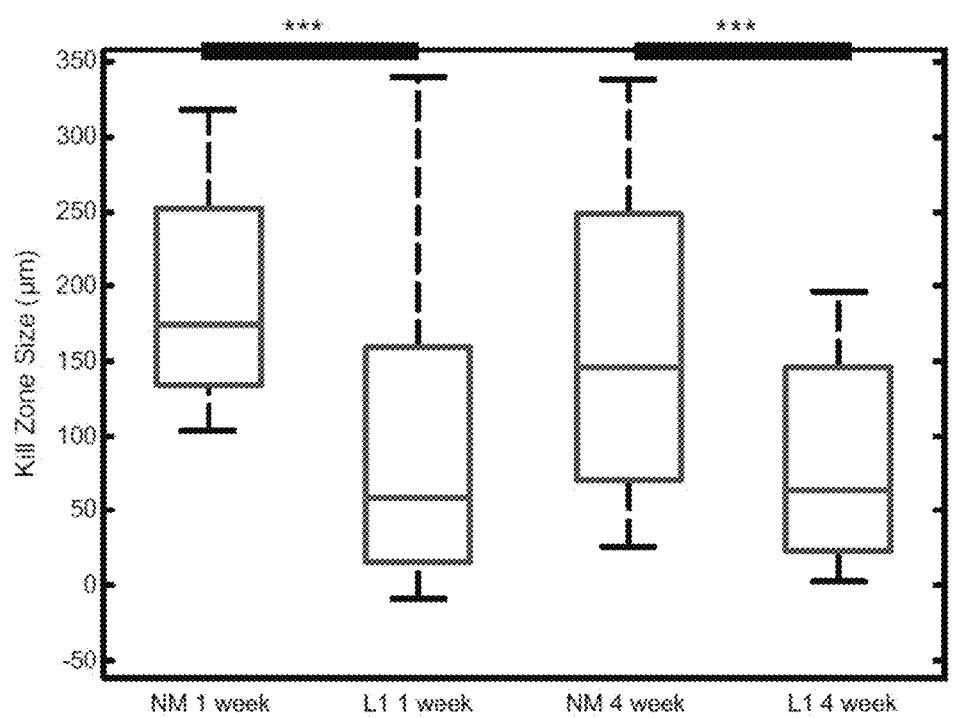
FIG. 3 shows a graph illustrating quantification of the kill zone size in the spinal cord in non-modified and L1 coated neural probes. 4',6-diamidino-2-phenylindole (DAPI)-stained images were used to define the perimeter of each implant and NF200-stained images used to identify the presence of neuronal processes. Kill zone size was computed in 10 degree bins around the 360 degree perimeter of the implant site by calculating the distance between the location of NF200 staining and the location of the implant. These distance measures were used to calculate the mean kill zone size and compared via the rank sum test. Significant decreases in kill zone size were observed with the L1 coating at both 1 week and 4 week time points. ***$p<0.001$.

Characterization of the tissue response in the spinal cord. A number of histological stains were performed to evaluate and characterize the tissue reaction in response to the NM and L1-coated probes (antibodies outlined in Table 3). First, to determine the degree of neuronal and axonal loss around the implant site, NF200 was used. In the spinal cord, NF200 staining is decreased or absent in the area immediately surrounding the implant site (FIG. 2). This area, termed the kill zone, was evident at both 1 week (FIG. 2A) and 4 week (FIG. 2B) time points. MATLAB was used to quantify kill zone sizes which were then compared via the rank sum test. In the spinal cord and at both time points, the size of the kill zone was significantly reduced (p<0.001) with the L1 coating as compared to the NM microelectrodes (FIG. 3).

Figures 4A, 4B:
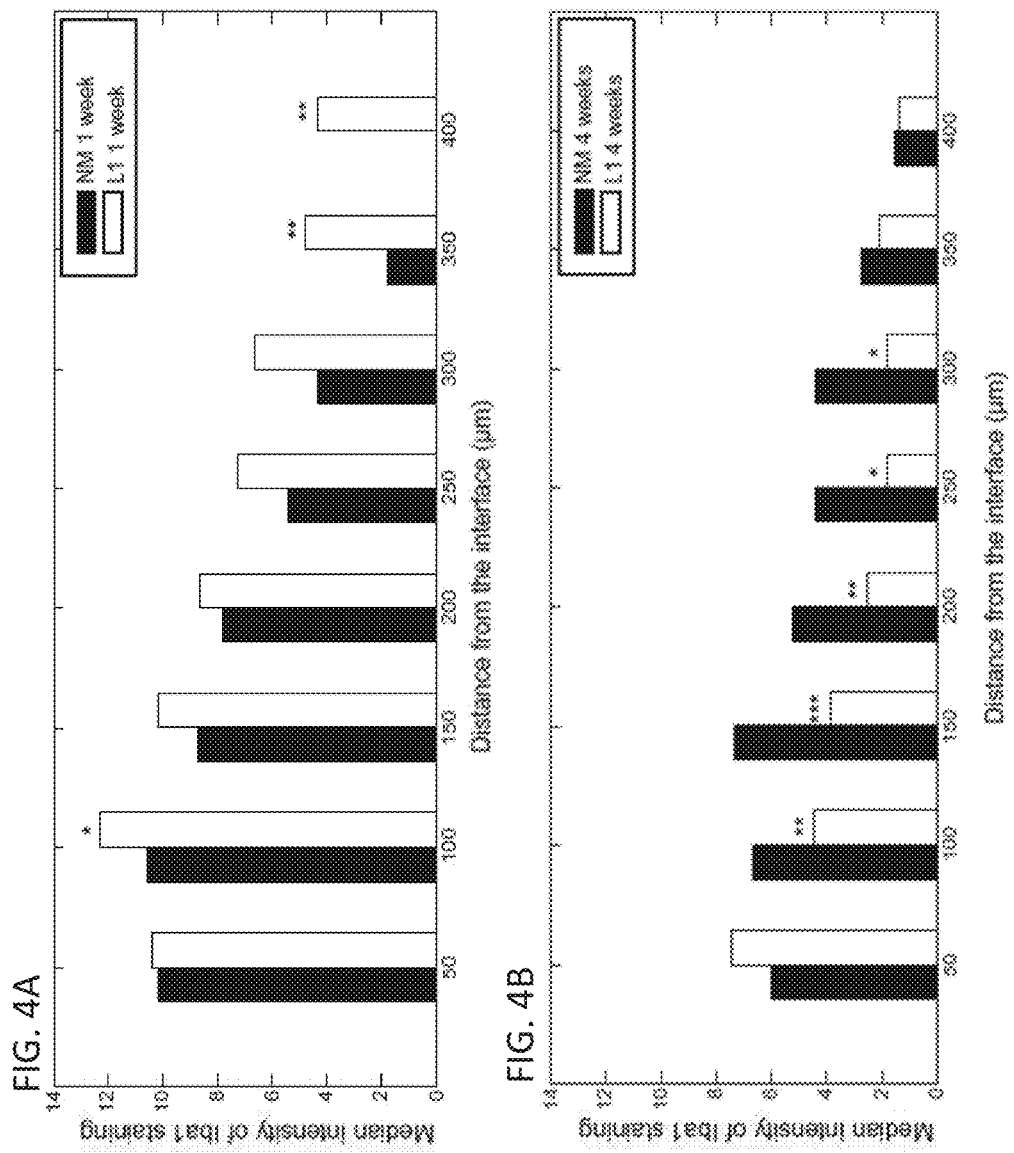
FIGS. 4A and 4B show a set of graphs illustrating Iba1 staining intensity as a function of distance from the electrode-tissue interface in the spinal cord. MATLAB was used to determine the decline in Iba1 staining intensity at 1 week (A) and 4 week (B) time points. The perimeter of the implant site was defined using the DAPI-stained images. Threshold values based on 95% of the background staining for each section were established, and Iba1 staining above this threshold measured as a function of distance from the implant site. The median intensity values were calculated in 50 μm bins and compared via the rank sum test. Significant increases were observed with the L1 coating at the 1 week time point. At 4 weeks, the L1 coating was associated with significant decreases in Iba1 staining. *$p<0.05$; $p<0.01$; *$p<0.001$.

The non-neuronal cell response was also characterized, including the reactions associated with microglia/macrophages, astrocytes and fibroblasts using Iba1, GFAP and vimentin antibodies, respectively. Cells that stained positive for Iba1 were localized to the area immediately surrounding the implant. The staining intensity was greatest at the interface and decreased in intensity further from the implant (FIG. 4). MATLAB was again utilized to assess the decay in Iba1 staining. For this analysis, decay as a function of distance from the implant site was graphically represented and the median intensity values in 50 μm bins were compared via the rank sum test (as shown in FIG. 4). In the spinal cord, there was little difference between NM and L1-coated probes at the 1 week time point (FIG. 4A).

However, at 4 weeks, the intensity of Iba1 staining was significantly higher with the NM probes (FIG. 4B).

Figure 5A:
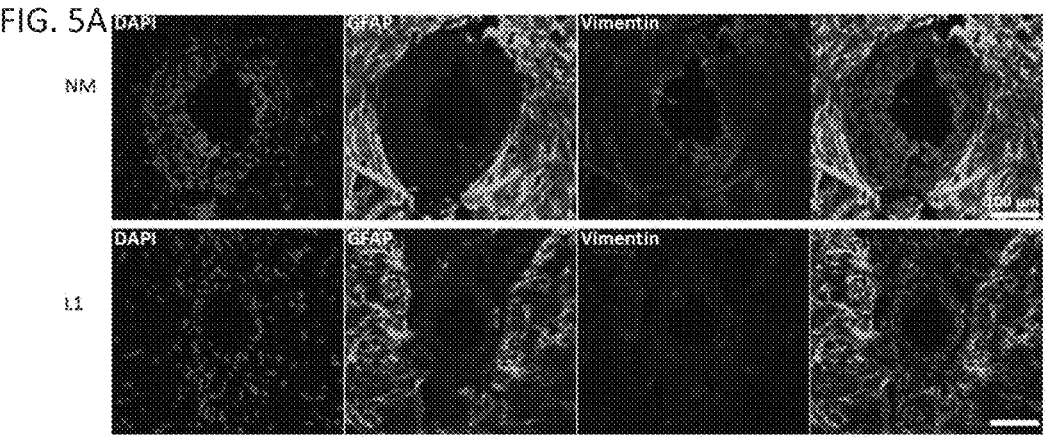
FIGS. 5A and 5B show a set of immunofluorescence images illustrating Glial fibrillary acidic protein (GFAP; green; an astrocyte marker) and vimentin (red) expression in spinal cord following implant of NM and L1-coated neural probes. GFAP staining was characterized by the formation of a sheath not located to the area immediately surrounding the implant. Vimentin-positive cells were localized around the implant site with some co-localization with GFAP. (A) Representative images at the 1 week (or acute) time point. (B) Representative images at the 4 week (or chronic) time point. Scale bars represent 100 μm.
Figure 5B:
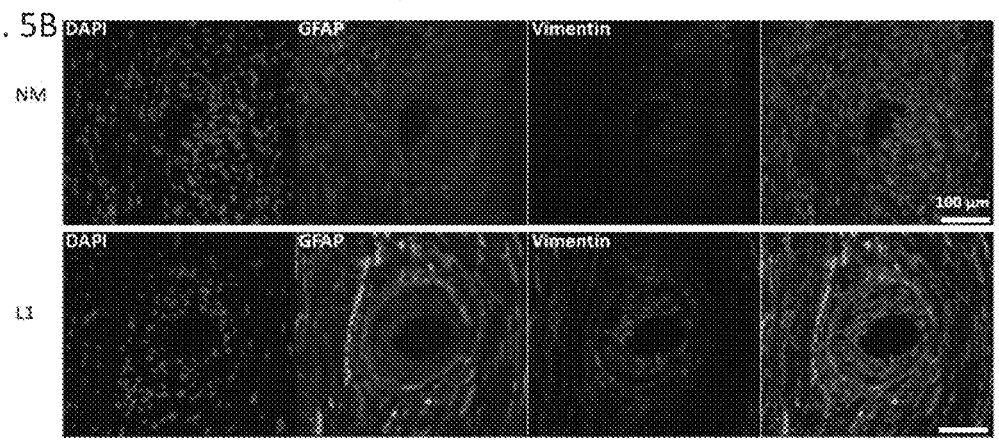

GFAP-positive cells, identified as reactive astrocytes, resulted in the formation of a sheath a short distance from the electrode-tissue interface (FIG. 5). Vimentin-positive cells were localized at and around the implant site with some co-localization with GFAP. Cells that were vimentin positive and GFAP negative were identified as microglia, endothelial cells and fibroblasts. To quantify GFAP staining, the same MATLAB analyses used for Iba1 staining quantification were used. In the spinal cord, there was little difference in GFAP staining intensity between acute and chronic time points (FIG. 6) although there were significant differences between the NM and L1 electrodes between 50-150 µm at 1 week and 150-300 µm at 4 weeks.

Figure 7:
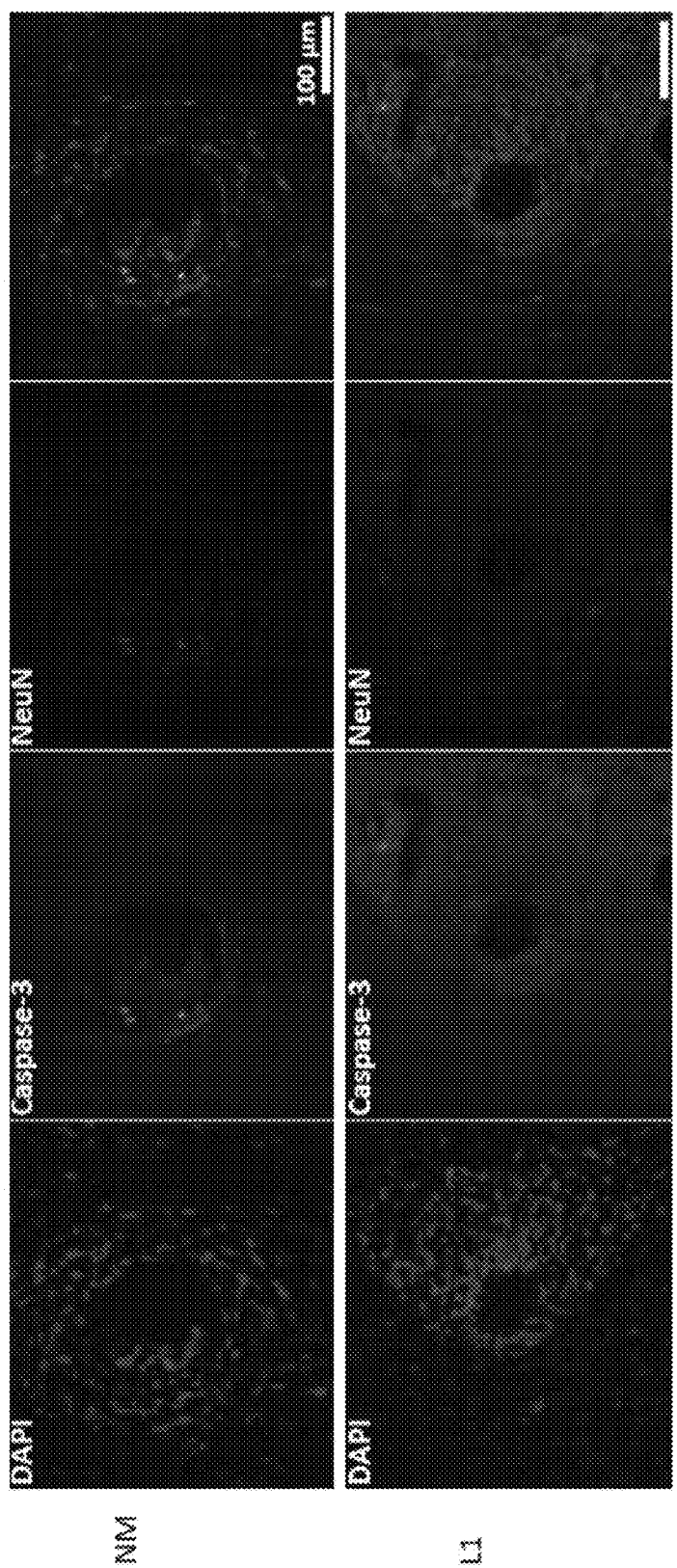
FIG. 7 shows a set of immunofluorescence images illustrating the co-localization of neuronal nuclei (NeuN, red) and activated caspase-3 (green) in the spinal cord following implant of NM and L1-coated neural probes. The number of NeuN/caspase-3 positive cells was quantified and reported as a percentage of the total number of NeuN positive cells. Scale bars represent 100 μm.

Finally, to determine the impact on neuronal cell death, the colocalization of NeuN and activated caspase-3 was determined (representative images provided in FIG. 7). In the spinal cord, L1-coated probes were associated with a decrease in the percentage of neuronal cell death as assessed by the number of NeuN/caspase-3 positive cells versus NeuN positive cells at both acute and chronic time points (Table 4).

Figure 8A:
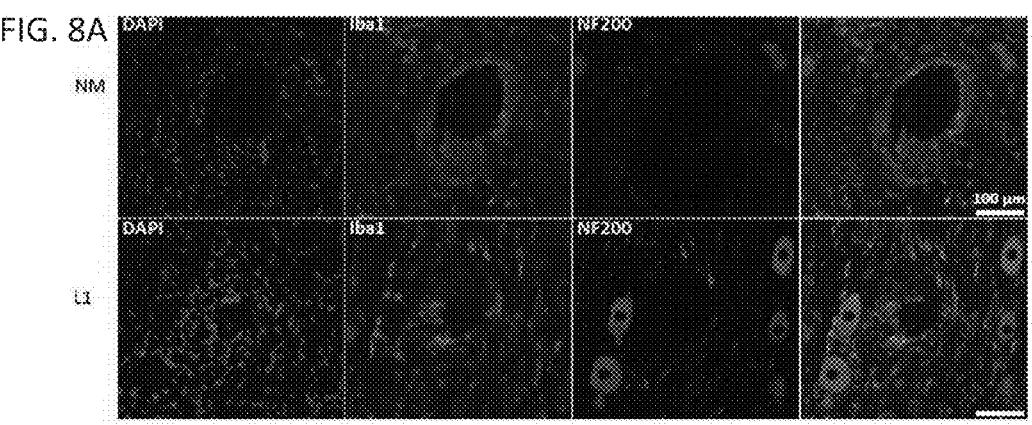
FIGS. 8A and 8B show a set of immunofluorescence images illustrating NF200 (red) and Iba-1 (green) expression in the dorsal root ganglion (DRG) following implant of NM and L1-coated neural probes. NF200 staining was lacking in the area immediately surrounding the implant site and differences assessed by measuring the size of the area void of this staining. Iba1-positive cells were localized around the implant site and this increased immunoreactivity quantified and compared. (A) Representative images at the 1 week (or acute) time point. (B) Representative images at the 4 week (or chronic) time point. Scale bars represent 100 μm.
Figure 8B:
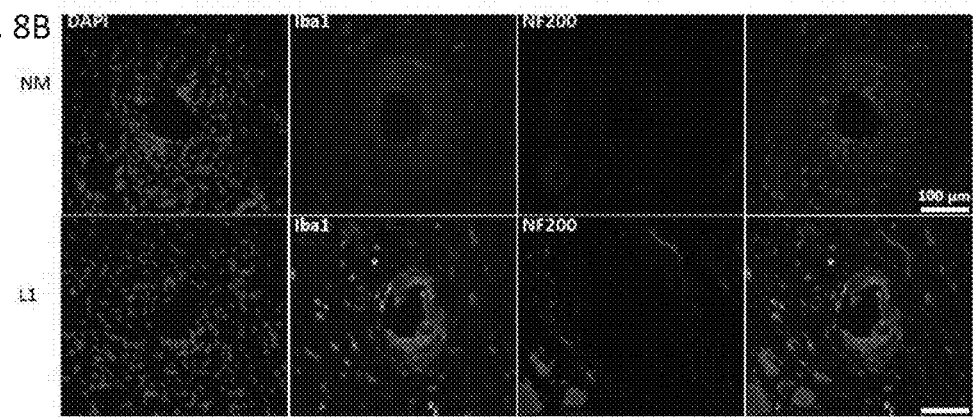
Figure 9:
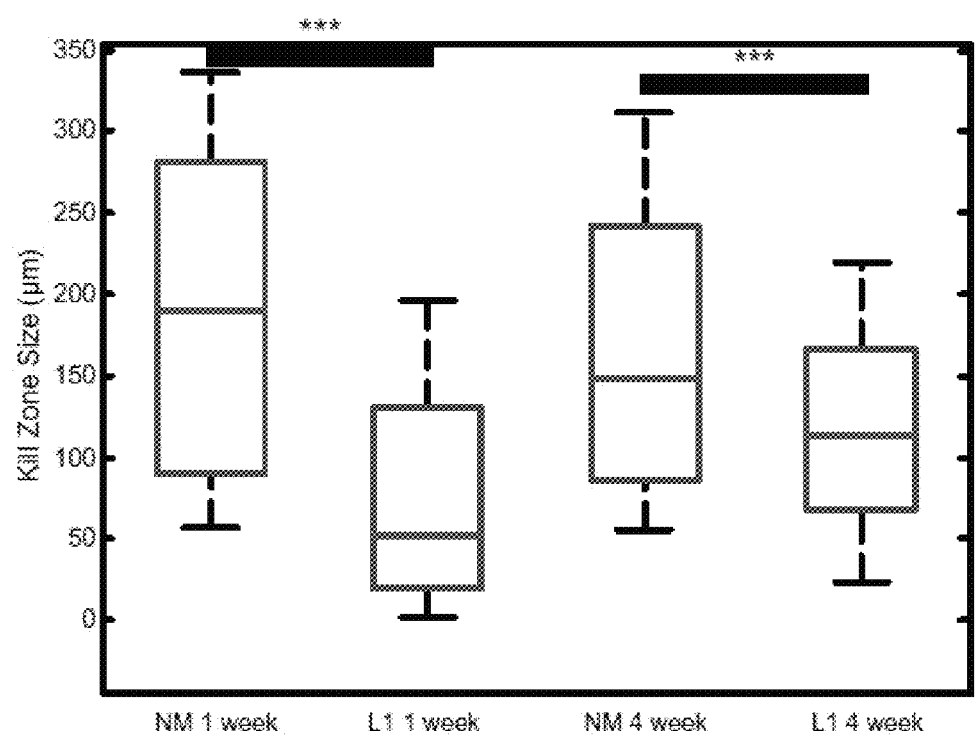
FIG. 9 shows a graph illustrating quantification of the kill zone size in the DRG in non-modified and L1 coated neural probes. DAPI-stained images were used to define the perimeter of each implant and NF200-stained images used to identify the presence of neuronal processes. Kill zone size was computed in 10 degree bins around the 360 degree perimeter of the implant site by calculating the distance between the location of NF200 staining and the location of the implant. These distance measures were used to calculate the mean kill zone size and compared via the rank sum test. Significant decreases in kill zone size were observed with the L1 coating at both 1 week and 4 week time points. ***$p<0.001$.

Characterization of the tissue Response in the DRG. The same histological stains used in the spinal cord were also used to assess the tissue response in the DRG. For NF200, staining intensity was decreased or absent in the area immediately surrounding the implant site (FIG. 8). Again, this kill zone was evident at both acute (FIG. 8A) and chronic (FIG. 8B) time points. In the DRG as in the spinal cord, the size of the kill zone was significantly reduced at both time points with the L1 coating as compared to the NM microelectrodes (p<0.001; FIG. 9).

For Iba1 staining, a significant decrease in staining intensity was observed at the 1 week time point in the DRG with the L1 coating (FIGS. 8A and 10A). Interestingly, the intensity of Iba1 staining was higher in the L1-modified group in the DRG at the 4 week time point when compared with the NM probes (FIGS. 8B and 10B).

Figure 11A:
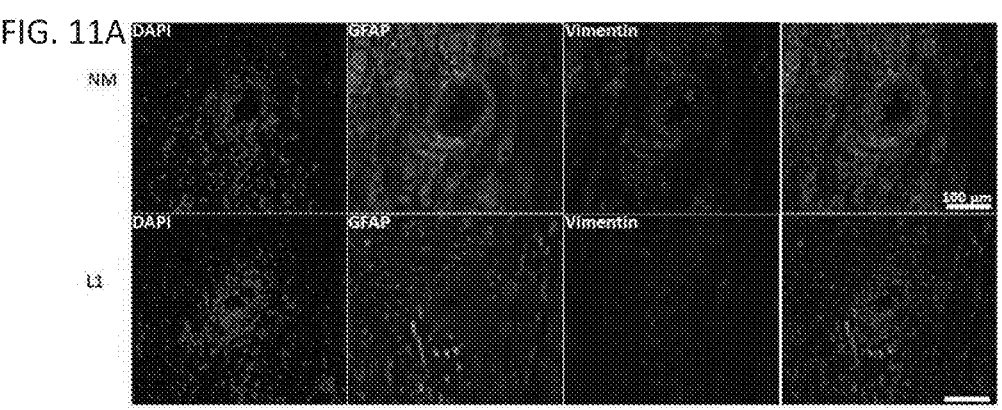
FIGS. 11A and 11B show a set of immunofluorescence images illustrating GFAP (green) and vimentin (red) expression in the DRG following implant of NM and L1-coated neural probes. GFAP staining was characterized by the formation of a sheath not located to the area immediately surrounding the implant. Vimentin-positive cells were localized around the implant site with some co-localization with GFAP. (A) Representative images at the 1 week (or acute) time point. (B) Representative images at the 4 week (or chronic) time point. Scale bars represent 100 μm.
Figure 11B:
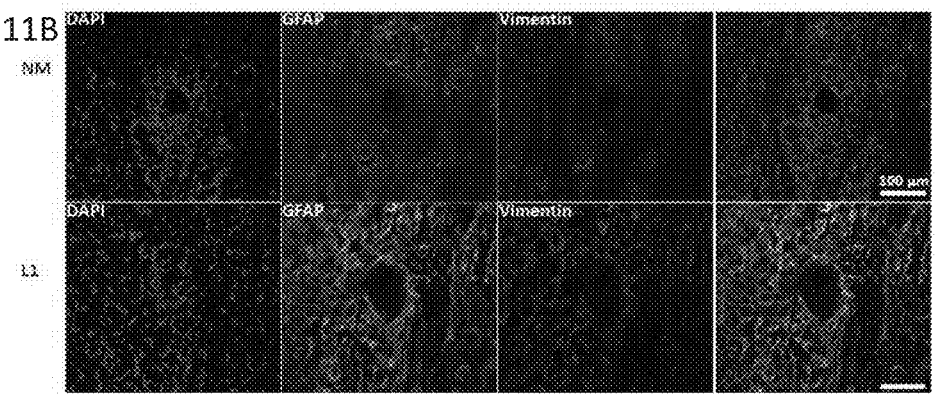
Figure 12A:
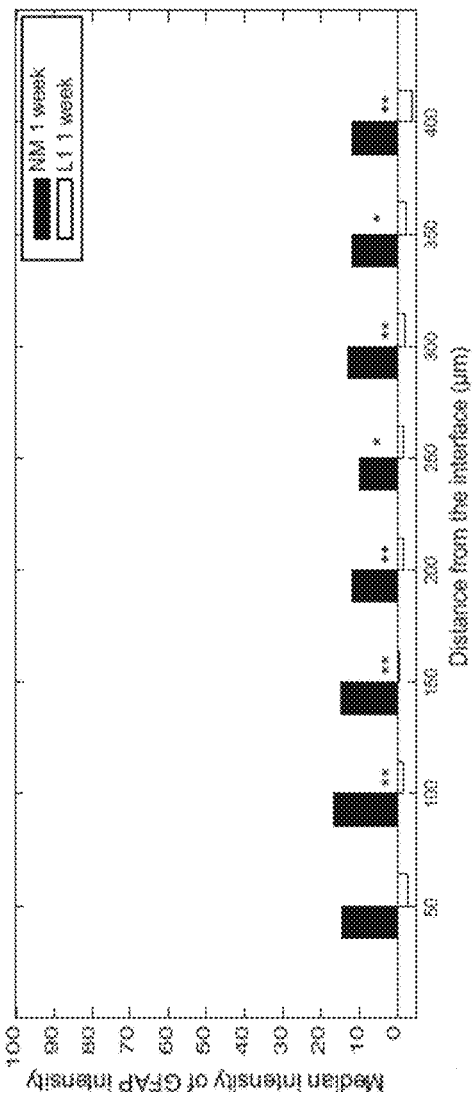
FIGS. 12A and 12B show a set of graphs illustrating GFAP staining intensity as a function of distance from the electrode-tissue interface in the dorsal root ganglion. MATLAB was used to determine the decline in GFAP staining intensity at 1 week (A) and 4 week (B) time points. The perimeter of the implant site was defined using the DAPI-stained images. Threshold values based on 95% of the background staining for each section were established and GFAP staining above this threshold measured as a function of distance from the implant site. The median intensity values were calculated in 50 µm bins and compared via the rank sum test. With L1, significant decreases were observed with the L1 coating at 1 week while significant increases were observed at 4 weeks. *$p<0.05$; **$p<0.01$.
Figure 12B:
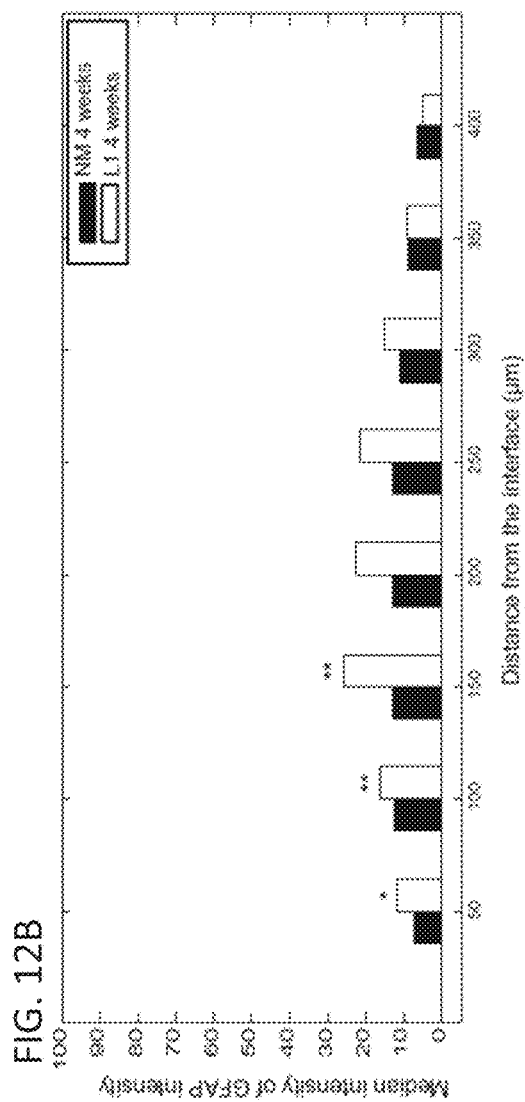

In the DRG, there was a significant decrease in GFAP staining intensity at the 1 week time point with the L1 coating (FIGS. 11 and 12A). However, the intensity of GFAP staining was increased in the DRG at the 4 week time point at distances up to 150 µm from the interface with L1-coated microelectrodes (FIGS. 11 and 12B).

Finally, L1-coated probes in the DRG were associated with a decrease in the percentage of neuronal cell death at both time points analyzed (FIG. 13 and Table 4) as observed in the spinal cord.

TABLE 2

Animals in each treatment group

| Site of Implant | Time Point | Number of Animals (NM) | Number of Animals (L1) |
|---|---|---|---|
| DRG | 1 week | n = 3 | n = 3 |
| DRG | 4 weeks | n = 3 | n = 3 |
| spinal cord | 1 week | n = 3 | n = 3 |
| spinal cord | 4 weeks | n = 4 | n = 3 |

TABLE 3

Antibodies used for histological characterization

| Antibody | Specificity |
|---|---|
| NF200 | Mature axons |
| Iba1 | Microglia/macrophages |
| GFAP | Astrocytes |
| Vimentin | Immature and reactive astrocytes, microglia, endothelial cells, fibroblasts |
| NeuN | Neuronal nuclei |
| Caspase-3 | Cleaved (activated) caspase-3 |

TABLE 4

NeuN/Caspase-3 colocalization

| Location | Time Point (week) | Coating Condition | Percentage of NeuN/Caspase-3 Positive Cells |
|---|---|---|---|
| spinal cord | 1 | NM | 11.3% (18 of 160) |
| | | L1 | 5.1% (12 of 235) |
| | 4 | NM | 21.8% (36 of 165) |
| | | L1 | 7.0% (31 of 440) |
| DRG | 1 | NM | 67.9% (142 of 209) |
| | | L1 | 31.5% (23 of 73) |
| | 4 | NM | 68.9% (51 of 74) |
| | | L1 | 12.4% (31 of 249) |

Discussion

One of the remaining challenges in the development of long-term neural interfaces or neuroprosthetics is maintenance of the cellular environment surrounding the implant. In particular, preventing neuronal cell death, promoting neuronal health and minimizing the inflammatory response are critical for success. Both central and peripheral nervous system sites including the spinal cord and DRG, respectively, are important target implant sites for such devices. In this study, the cellular response in these less well-studied locations was compared at both acute and chronic time points and the ability of L1 surface modifications to improve the tissue-electrode interface was investigated. The results indicate that neuronal density and health are significantly improved in the presence of the L1 surface modification in both central and peripheral locations.

The Cellular Response to Implanted Probes in the Spinal Cord and DRG. As potential sites for interfacing with neural prosthetics, it is important to understand the tissue response to neural probes implanted in the spinal cord and DRG. In the spinal cord, a significant decrease in the amount of staining for neuronal processes was observed immediately surrounding implant sites for non-modified probes (FIG. 2). This kill zone was apparent at both the acute and chronic time points. However, the size of the kill zone was significantly larger at the 1 week time point (median size of 174.56 µm) than at the 4 week time point (median size of 145.56 µm; p<0.001) suggesting some degree of axonal regeneration following injury.

In the central nervous system, microglia are resident cells that are activated along with astrocytes in response to injury. In both central and peripheral tissues, invading cells express Iba1, a calcium binding protein localized exclusively to microglial cells in the nervous system (Ito et al., *Brain Res Mol Brain Res*, 57:1-9, 1998; Patro et al., *Indian J Exp Biol*, 48:110-6, 2010). This protein plays an important role in cell migration and mediates the phagocytic activity of microglia (Ohsawa et al., *J Biomed Mater Res*, 52:460-6, 2000). Iba1 is also up-regulated in a variety of conditions indicating its importance in the activated microglial phenotype (Ito et al., *Brain Res Mol Brain Res*, 57:1-9, 1998; Ohsawa et al., *J Biomed Mater Res*, 52:460-6, 2000; Ito et al., *Stroke*, 32:1208-15, 2001; Mori et al., *Brain Res Mol Brain Res*, 120:52-6, 2003). For the Iba1-mediated component of the inflammatory response, increased staining was observed in the area immediately surrounding the implant with levels reaching that of the background as the distance from the interface increased. Although both acute and chronic time points experienced this decay as a function of distance, the overall intensity of the Iba1 response was significantly greater at the 1 week time point at distances ranging from 0-250 μm (0-50 μm, $p<0.01$; 50-100 μm, $p<0.01$; 100-150 μm, $p<0.05$; 150-200 μm, $p<0.001$; 200-250 μm, $p<0.05$). Astrocyte staining patterns for the uncoated probes were characterized by a sheath a short distance from the interface. Again, the formation of this glial scar was observed at both time points with a decline in staining intensity to background levels as the distance from the interface increased. However, there was a significant increase in the intensity of GFAP staining between 50 and 100 μm at the 4 week point ($p<0.01$) suggesting that the uncoated probes continued to promote astrocyte migration after the acute injury. Vimentin staining was also assessed as this protein is expressed by a number of cell types including immature and reactive astrocytes, microglia, endothelial cells and fibroblasts.

The response observed in the DRG was similar in many ways to that observed in the spinal cord. For example, a decrease in the amount of neuronal process staining in the kill zone was observed in this peripheral site and at both time points studied (FIG. 8). The size of the kill zone was significantly larger at the 1 week time point (median size of 190.18 μm) than at the 4 week time point (median size of 148.65 μm; $p<0.001$) again suggesting a regenerative process following injury.

In peripheral tissues like the DRG, it is believed that immune cells also invade following injury (Bennett et al., *J Neurosci*, 18:3059-72, 1998; Hu et al., *Brain Behav Immun*, 21:599-616, 2007) and some of these cells express Iba1. The Iba1-mediated component of the inflammatory response in the DRG resembled that of the spinal cord. Iba1 staining in the area immediately surrounding the implant was increased and levels reached that of the background with increasing distance from the interface. In comparing the 1 and 4 week time points, the overall intensity of the Iba1 response was significantly greater at the 1 week time point at distances up to 350 μm from the interface (0-50 μm, $p<0.001$; 50-100 μm, $p<0.001$; 100-150 μm, $p<0.001$; 150-200 μm, $p<0.001$; 200-250 μm, $p<0.01$; 250-300 μm, $p<0.05$; 300-350 μm, $p<0.05$). The GFAP staining observed in the DRG can be attributed to satellite glial cells (SGCs) which ensheath the DRG perikarya after injury (Hanani et al., *Brain Res Brain Res Rev*, 48:457-76, 2005) and are thought to control the neuronal microenvironment in the DRG (Keast and Stephensen, *J Comp Neurol*, 424:577-87, 2000). Finally, caspase-3-mediated neuronal apoptosis was also observed in the DRG as in the spinal cord.

Figure 13:
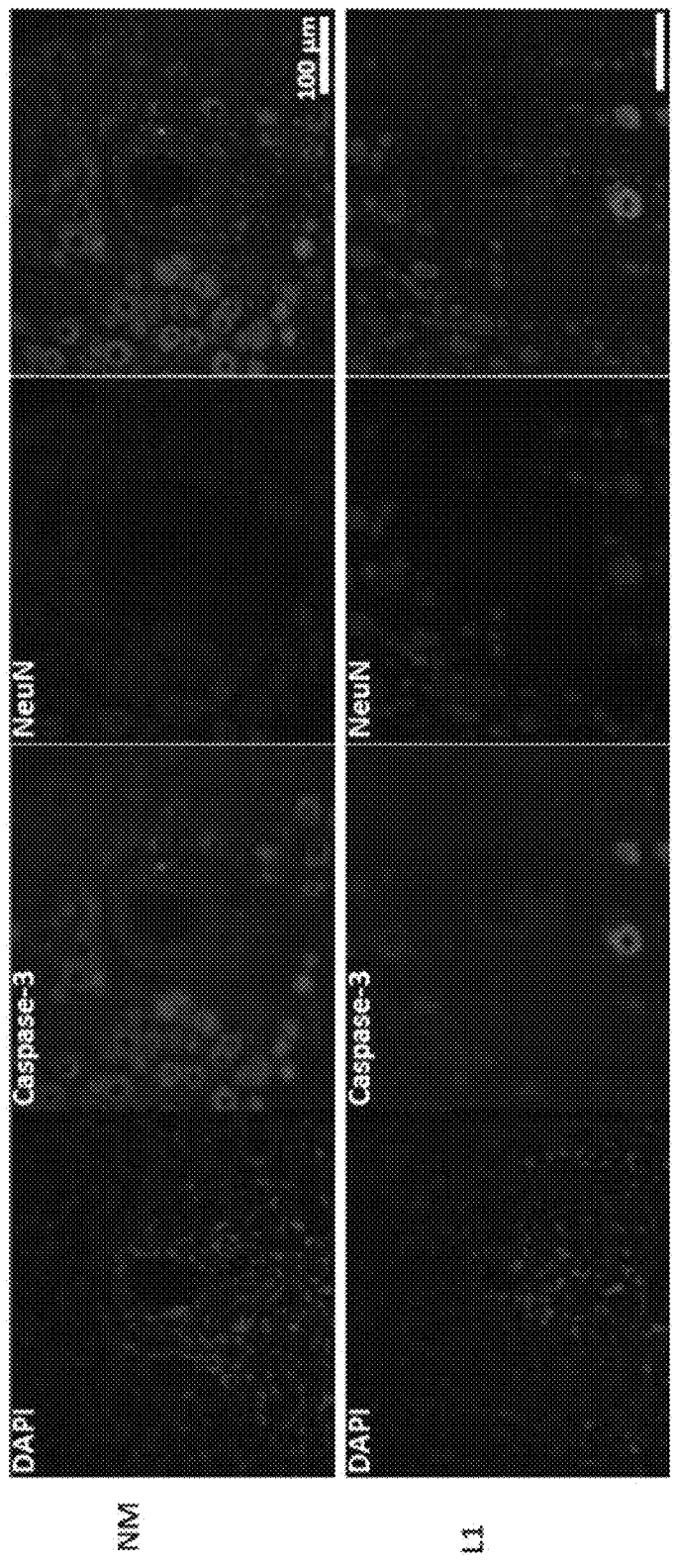
FIG. 13 shows a set of immunofluorescence images illustrating co-localization of NeuN and activated caspase-3 in the DRG. Immunofluorescence images were used to determine the degree of co-localization between NeuN (red) and cleaved caspase-3 (green); representative images are provided. The number of NeuN/caspase-3 positive cells was quantified and reported as a percentage of the total number of NeuN positive cells. Scale bars represent 100 µm.

Effects of the L1 coating. In terms of neuronal presence around the implants, significant decreases were observed in the size of the kill zone with the L1 coating at both 1 week and 4 weeks and in the spinal cord (FIG. 3) and DRG (FIG. 9). In addition, neuronal health appeared to improve in the presence of L1 as a significantly lower percentage of neurons were positive for activated caspase-3, an important cellular mediator of programmed cell death (FIGS. 7 and 13 and Table 4). This may be due to the regenerative responses associated with L1 following nervous system injury. Taken together, these results indicate that the L1 immobilized on the implanted microelectrodes can promote regeneration of injured neurons or axons near the implant site.

In the spinal cord, our analyses indicate that Iba1 staining intensity only differed between NM and L1-coated microelectrodes at distances 50-100 μm from the implant site at the early time point although at the 4 week time point there was a significant decrease in Iba1 staining intensity with the L1 coating at distances 50-300 μm from the implant site. In the DRG, a decrease in Iba1 staining intensity was observed with L1 at the 1 week time point and then an increase in Iba1 intensity with L1 at the 4 week time point.

Reactive astrogliosis is a prominent response of the central nervous system to injury and can be characterized by increased expression of GFAP, cell and process enlargement and proliferation (Sofroniew and Vinters, *Acta Neuropathol*, 119:7-35, 2010). This leads to local accumulation of astrocytes and formation of what is termed the glial scar, characterized by the deposition of a dense extracellular matrix (Irintchev and Schachner, *Neuroscientist*, 18:452-466, 2011). Although a significant difference in GFAP staining intensity was not observed in the spinal cord with the L1 staining, GFAP immunoreactivity for both NM and L1-modified probes increased as a function of time. As reported by other groups, reactive astrocytes progressively displace neurons away from the recording zone, a mechanism that likely accounts for failure during single unit recordings in the brain (Polikov et al., *J Neurosci Methods*, 148:1-18, 2005; Szarowski et al., *Brain Res*, 983:23-35, 2003).

In summary, immobilization of L1 protein significantly promotes neuronal density and neuronal health at the tissue-probe interface at both acute and chronic time points. These results suggest that immobilization of L1 may increase the biocompatibility of neural probes used both centrally and peripherally for rehabilitative and therapeutic purposes.

Example 2

Coating Neural Probes with Brain Derived Neural Adhesion Molecule L1

This example illustrated surface immobilization protocols to coat neuron specific cell adhesion molecule L1 on various neural probes with different surface chemistry.

The cell adhesion molecule L1 was purified by immunoaffinity chromatography as previously described (Lagenaur and Lemmon, Proc. Natl. Acad. Sci. USA, 1987. 84: p. 7753-7757).

For neural probes with silicon oxide surface, silane chemistry and a GMBS crosslinker are used to covalently attach L1 and polyethylene glycol on surfaces. Characterization of the surface using dual polarization interferometry indicates that the surface bound L1 mass is 2.67 ng/mm$^2$ (Azemi et al., Acta Biomaterialia, 2008. 4(5): p. 1208-1217; incorporated by reference herein in its intirety). NeuroNexus probes were coated using this approach and implanted for 1, 4 and 8 weeks. The effects of L1 were evaluated with immunohistochemistry and quantitative image analysis. Whereas non-modified probes induced persistent glial activation and significant decreases of neuronal and axonal densities (FIG. 14), the immediate area (100 μm) around the L1 coated probe showed no loss of neuronal bodies and a significantly increased axonal density relative to background (FIGS. 14A-14D). In this same region, significantly lower activation of microglia and reaction of astrocytes around the L1 modified probes were found when compared to the control probes (FIGS. 14E-14G) (Azemi et al., Biomaterials, 2011. 32(3): p. 681-92).

Several coating strategies were developed to immobilize proteins on a parylene C surface. The first approach utilized air plasma to modify the parylene C surface with polar hydroxyl groups at the surface, as previously described (see Chang et al., Langmuir, 2007. 23(23): p. 11718-25; Sia and Whitesides, Electrophoresis, 2003. 24(21): p. 3563-76, which is incorporated by reference herein in its entirety). The probes are then soaked in L1 containing protein solution for 1 hour. The successful attachment of the L1 protein was characterized by immunostaining and the bioactivity of the L1 coated probe was verified in cell culture (Kolarcik et al., Acta Biomater, 2012. 8(10): p. 3561-75).

Two additional coating methods have also been developed that can covalently attach proteins on parylene C surfaces. The first method involves surface treatment of parylene C with succinic anhydride to add carboxylic acid groups on the surface, which can then react with amine on proteins (FIG. 15E) (succinic anhydride treatment of parylene C has been previously described, see, e.g., Zhang et al., Acta Biomater, 2011. 7(10): p. 3746-56, which is incorporated by reference herein in its entirety).

Figure 15F:
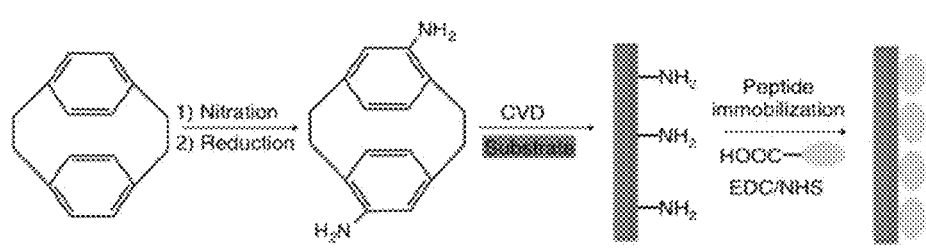

An additional method involves the synthesis of diamino (2.2)paracyclophane by nitration of (2.2)paracyclophane and subsequent reduction of the nitro groups. The diamino (2,2)paracyclophane can then form a parylene coating in a CVD chamber which has amine groups available for protein binding (FIG. 15F) (see, e.g., Lahann et al., Angew Chem Int Ed Engl, 2001. 40(16): p. 2947, which is incorproated by reference herein in its intirety).

To promote neuronal attachment on the tip of the recording electrode, two methods are found to be effective: 1) Direct co-deposition of conducting polymer and L1 on electrode sites (FIGS. 16A-16B); and 2) Polyethylenedioxythiophene (PEDOT) doped with graphene oxide (GO) which can then be covalently linked to protein via carboxylic acid groups on GO (FIGS. 16C-16D) (Luo et al., J Mat. Chem. B, 2013. 1(1): p. 1340-1348, which is incorporated by reference herein in its intirety).

Example 3

L1 Coating Improves Chronic Recording Performance

Figure 17A:
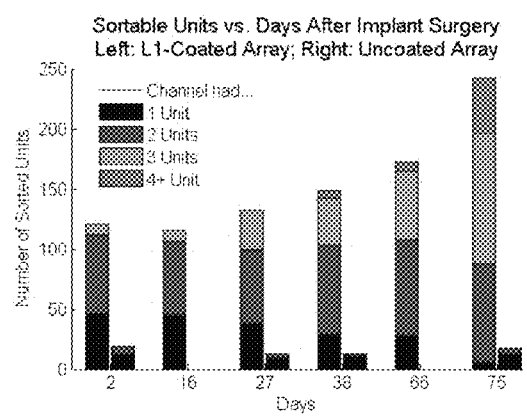
FIGS. 17A-17D show results from chronic recording from L1 coated and non-coated 10×10 Utah arrays (UEA) implanted into the motor cortex of a single monkey. (A) L1 coated array (left) detected significantly greater number of single units compared to non-coated array (right) over time. At 75 days, L1 coated array records over an order of magnitude greater number of sorted units. (B) seven distinguishable single units detected from a single channel of the L1 coated array. (C) representative channel shows stable single-unit (tuning and waveform shape) over days. (D) Histogram of the largest single-unit signal amplitude per channel in the L1-coated UEA 2.5 months after implantation. Two channels have amplitude >1 mV and only 3 channels have amplitude <200 µV.
Figure 17B:
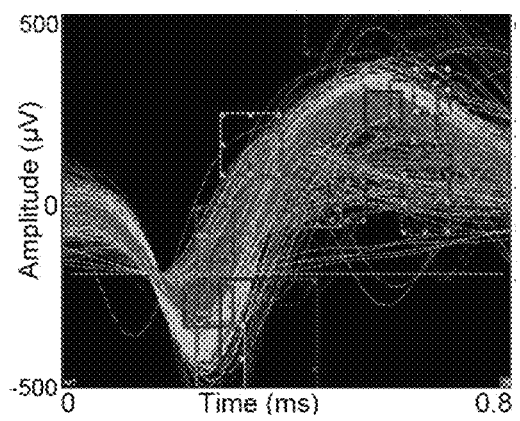
Figure 17C:
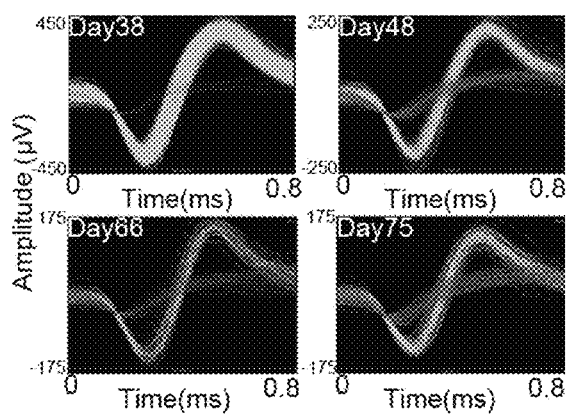
Figure 17D:
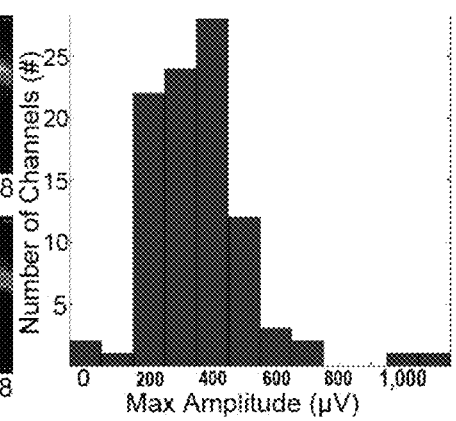
Figure 18A:
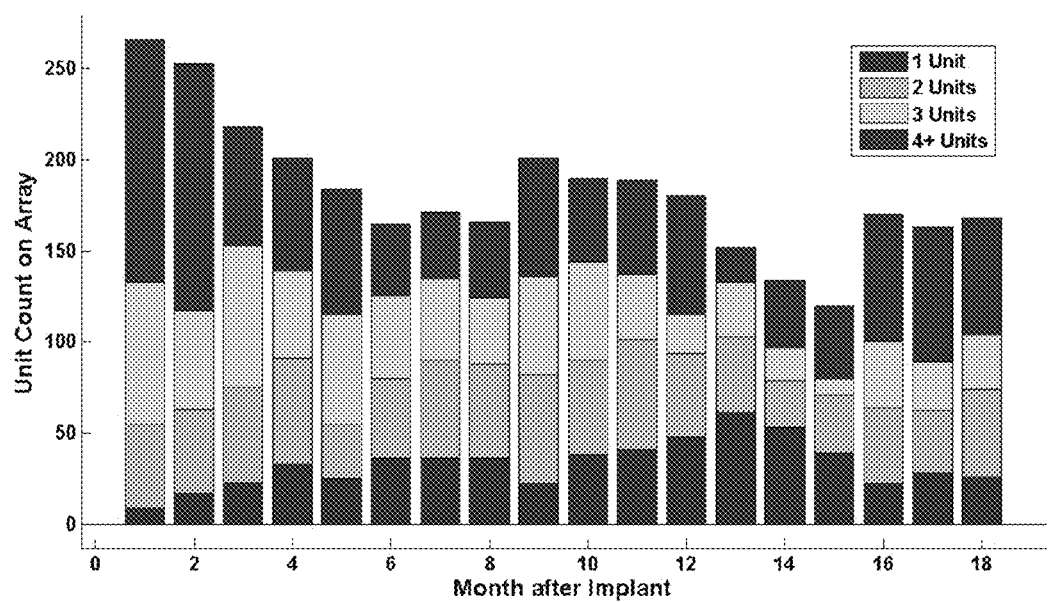
FIGS. 18A and 18B are graphs showing continued results from chronic recording from the L1 coated and non-coated 10×10 Utah arrays (UEA) implanted into the motor cortex of the monkey as shown in FIG. 17. (A) L1 coated array detected single units over 18 months of ongoing chronic recording. (B) On some channels, unit waveforms are very stable and signal amplitudes are extraordinarily large even at day 447.
Figure 18B:
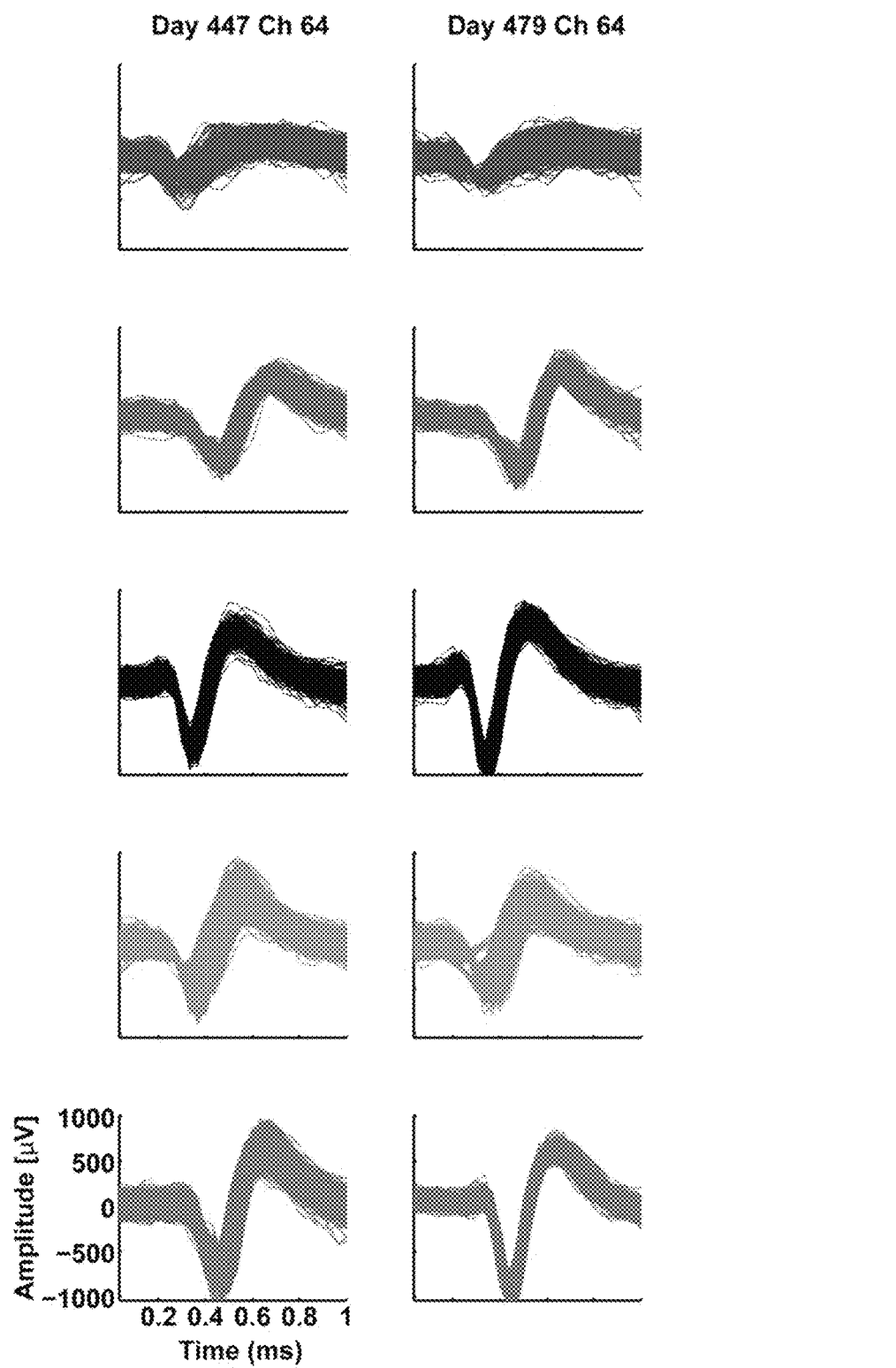

L1 was isolated from rhesus monkey brain (Worldwide Primate) using known methods (see, e.g., Lagenaur and Lemmon, Proc. Natl. Acad. Sci. USA, 1987. 84: p. 7753-7757, incorporated by reference herein in its intirety). An L1 coated 96 channel Blackrock array (coated using protein adsorption of L1 as described herein), and a non-coated array were implanted in the right hemisphere motor cortex of a monkey. The L1 coated arrays detected 120 single-units on day 2 and the unit counts continued to increase to 240 on day 75 (FIG. 17). Remarkably, many channels have more than one and up to 7 well isolated single-units (FIG. 17b). The amplitude of some of the units can be as high as 1 mV (FIG. 17D). The increases continued for extended time periods, with excellent recording performance maintained at 18 months post-implant (FIG. 18A). On some channels, unit waveforms are very stable and signal amplitudes are extraordinarily large even at day 447 (FIG. 18B). This high amplitude suggest that the neuron is directly on the electrode site with very tight cell-electrode seal (Pettersen and Einevoll, Biophys J, 2008. 94(3): p. 784-802.).

Example 4

Production of L1 Coated Probes

This example illustrates exemplary methods of producing and sterilizing L1 coated probes.

Several approaches have been developed to covalently attach the L1 polypeptide to the surface of silicon dioxide or parylene C coated neural probes, and store the probes for future use. However, immobilized protein tends to denature easily in nonphysiological conditions. For example, ethylene oxide sterilization treatment completely destroys the bioactivity of L1 attached to parylene C coverslips as demonstrated by the poor neuronal attachment and neurite growth in culture (FIG. 20B). Drying in air reduces protein activity, though bioactivity is still retained (FIG. 20C). Methods of producing L1 coated probes are described below, concerning coating for both parylene C-insulated and silicon dioxide-insulated probes.

In a first approach, to produce a L1-coated probe that that can be directly sterilized, an L1 protein-polymer conjugate can be synthesized and then conjugated to a modified neural probe. Polymer-protein conjugates have been synthesized which maintain, and in some cases enhance, performance of the conjugated protein, while improving stability during storage as well as sterilization (Thilakarathne et al., 2011. 27(12): p. 7663-7671). L1 can be covalently attached to the carboxyl functional groups of poly(acrylic acid) (PAA) and lightly cross-linked (e.g., with EDC chemistry), resulting in a stable and soluble L1-polymer conjugate. For silicon oxide substrates, the L1-polymer conjugate can then be covalently attached to the silicon oxide surface using traditional silanization/GMBS methods as described above. For parylene C substrates, two exemplary immobilization strategies can be utilized: a) direct attachment to the parylene C surface following oxygen plasma treatment; or b) attachment to the parylene C surface via EDC/NHS cross-linking following oxygen plasma treatment. For these protocols, Clean parylene C substrates are exposed to $O_2$ plasma for 15 s (30 W). Immediately afterwards, the substrates are submerged in a sterile $H_2O$ solution containing 0.2M EDC and 0.2M NHS and incubated at room temperature for 1 hr. After rinsing the substrates, the EDC/NHS functionalized surfaces are incubated in the L1-protein solution (100 μg/mL) for 1 hr. Protein coated parylene C substrates are then rinsed repeatedly prior to subsequent experiments.

Figure 22:
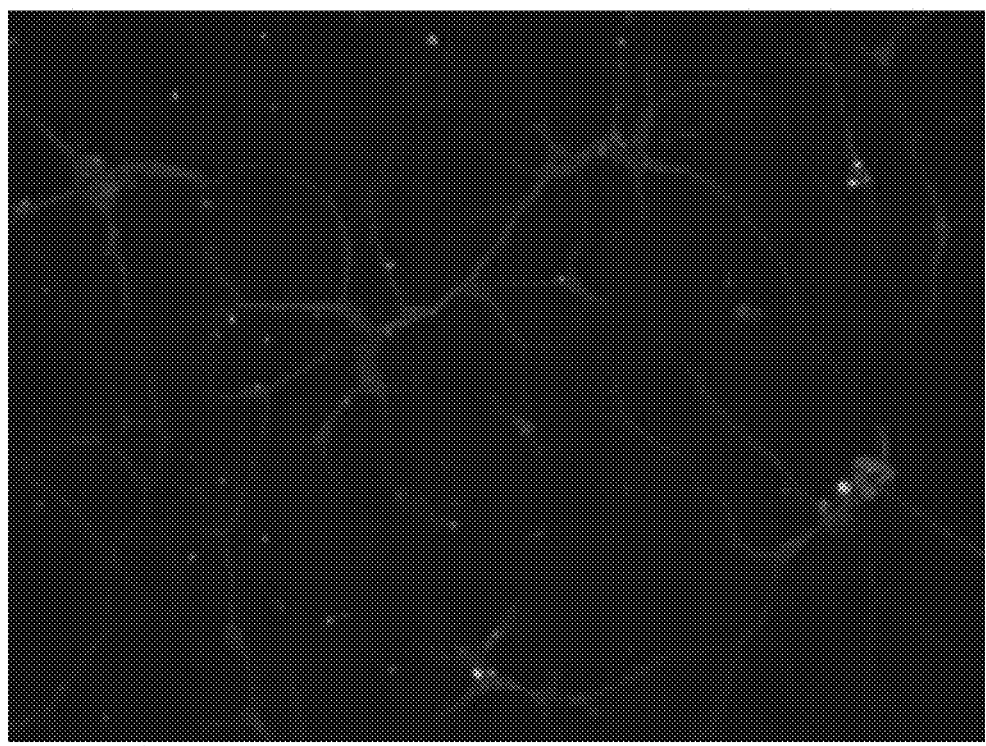
FIG. 22 shows an immunofluorescence image illustrating neuron growth on parylene-C and L1 coated cover slips that were produced by treatment of parylene-C coated coverslips with oxygen plasma, followed by covalent attachment of L1 to the activated parylene C by ethyl(dimethylaminopropyl) carbodiimide (EDC)/N-Hydroxysuccinimide (NHS) crosslinking.

FIGS. 21-22 illustrate conjugation of L1 to a parylene C surface via EDC/NHS cross-linking following oxygen plasma treatment. A parylene C coated coverslip was treated with oxygen plasma as described (see, e.g., Golda et al., 2013. Materials Science and Engineering. 33: 4221-4227, incorporated by reference in its entirety). The treated coverslip was then incubated with succinimide overnight, and EDC/NHS chemistry was used to crosslink the L1 to the parylene C coated coverslip substrate (FIG. 21A). The coupling reaction was monitored as shown in FIGS. 21B and 21C. To monitor coupling, the bioactivity of the coated samples was assessed by determining the bioactivity of the samples, neurons are plated onto the surface and grown for 3 days. On day 3, cells are fixed and examined for cell density and neurite outgrowth. The increase in N 1 s at ~400 indicates successful attachment of succinimidyl ester. Protein functionalization verified by increases in N is and the increase in O/N:Cl ratio. After coupling L1 to the parylene coat on the coverslip using EDC/NHS chemistry following oxygen plasma treatment, neuron growth is promoted and neurite outgrowth is extensive (FIG. 22). However, neuron growth was not observed if the L1 coat was performing the EDC/NHS chemistry without prior oxygen plasma treatment.

In another approach, for production of a sterile coating that is preserved under restricted conditions prior to use, three exemplary protocols are provided:

1: Substrates can be coated with L1 using previously discussed techniques for silicon oxide and parylene C and immediately freeze-dried. Freeze-drying has been used to prolong the activity of proteins in storage at low temperatures for both free and immobilized proteins (see, e.g., Neil et al., Biomacromolecules, 2009. 10(9): p. 2577-2583, which is incorporated by reference herein). Coated samples can be maintained at −20° C. in the presence of desiccant for 1 week (or longer) at which point the samples can be rehydrated with sterile PBS prior to use.

2: Prior to freeze-drying the protein-coated substrates (as in 1 above), each prepared substrate can be lightly cross-linked via free radical oxidation. Low levels of superoxide improved the stability of air-dried, L1-coated substrates (see FIG. 20D), which may be a result of the known cross-linking capabilities of oxidative species and the increased stability of more rigid cross-linked proteins (see, e.g., Brisson et al., Function of Oxidative Cross-Linking of Cell Wall Structural Proteins in Plant Disease Resistance. The Plant Cell Online, 1994. 6(12): p. 1703-1712; Choquet et al., Cell, 1997. 88(1): p. 39-48).

3: A protective coating composed of layer-by-layer-deposited mannitol and polyelectrolytes can be used to seal the prepared L1-coated substrates and to improve stability prior to freeze-drying (as in 1 above). This approach has been previously described in the context of protecting vaccine antigen (see, e.g., Dierendonck et al., ACS Nano, 2011. 5(9): p. 6886-93, which is incorporated by reference herein). Stored L1 coated probes can then be rehydrated with sterile PBS to dissolve the protective coating. Alternatively, polyethylene glycol gel may be applied to preserve the bioactivity of the underlying protein upon freeze-drying and storage, a method that has shown effective in preserving and even increasing the bioactivity of glucose oxidase in glucose sensors.

In an additional approach, for a multi-component shipping strategy, the neural probe (prior to L1 coating) can be prepared using previously described techniques for silicon oxide or parylene C substrates; however, prior to the L1-immobilization step, the "activated" substrates can be 1) air dried; 2) freeze-dried; or 3) inert-gas dried (N2/Ar). The substrates can then be packaged and sent to a user along with an appropriate amount of purified L1 to conjugate to the substrate to generate the L1 coated probe for use. For example, following shipping, the substrates can be submerged in a sterile L1 solution and tested for bioactivity.

Multiple tests can be used to assay the L1-coated probe. For example, the bioactivity of the coating can be determined using neuronal and glial cell cultures. Primary neurons grown on an L1-coated surface have a characteristic growth pattern of very long and straight processes. Therefore, neurite length can be quantified as a metric to determine bioactivity of the L1. Astrocyte attachment, on the other hand, is inhibited by L1, so the amount of astrocyte attachment, which inversely relates to the activity of L1, can also be used as another quantifiable metric. Additionally, the neural recording capability can be assessed by applying the L1 coating to commercially available probes (e.g., Blackrock or NeuroNexus arrays) which are implanted into neural tissue in an animal model (e.g., rat neural cortex). A visually evoked recording model will be used to assess recording quality, stability and longevity against an uncoated control on the contralateral side.

Example 5

Recombinant Human L1 Promotes Neurite Outgrowth

Figure 23A:
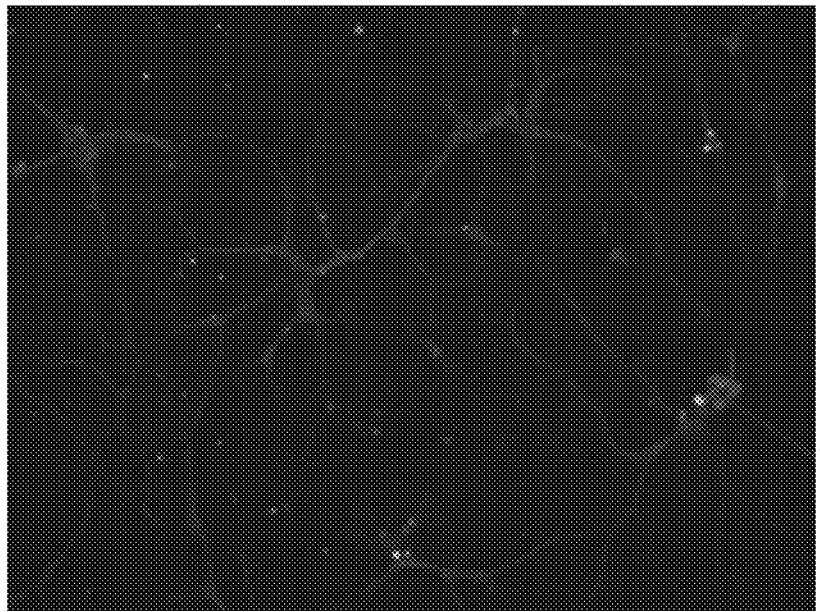
FIGS. 23A and 23B show immunofluorescence images illustrating that L1 purified from rat brain (FIG. 23A) and human L1 produced recombinantly by expression in HEK293 cells (FIG. 23B) can support neuron growth. The L1 preparations were conjugated to parylene-C coated coverslips using the oxygen plasma initiated EDC/NHS coupling method described herein.
Figure 23B:
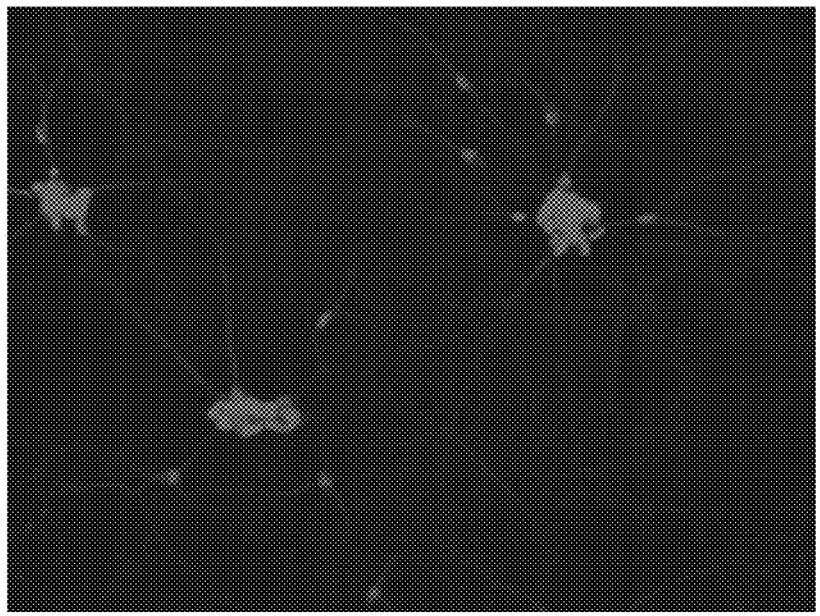

This example illustrates that recombinant L1 promotes neurite outgrowth. Recombinant human L1 was purchased from Millipore (CAT: GF220) and conjugated to parylene-C coated coverslips using the oxygen plasma initiated EDC/NHS coupling method described above. As shown in FIG. 23, L1 isolated fresh from rat pup cortical tissue (FIG. 23A) as well as the recombinant human L1 (expressed in HEK293 cells)(FIG. 23B) both promoted neurite outgrowth using the method.

Example 6

Cross-reactivity of L1 Orthologues

Figure 24:
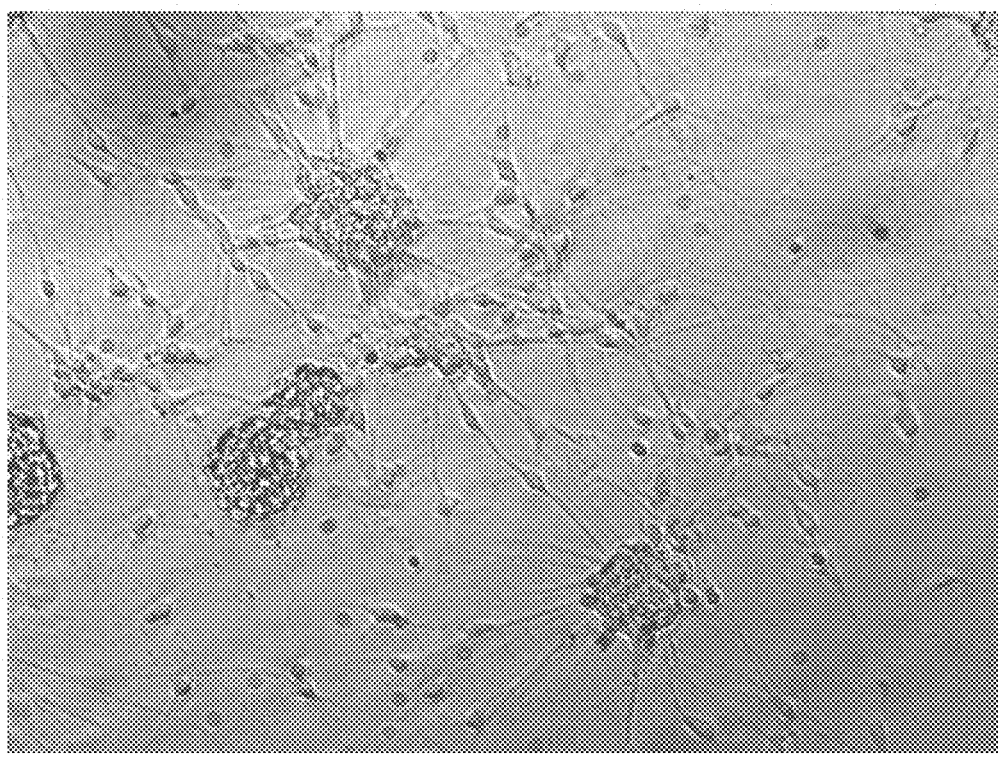
FIG. 24 shows a light microscopy image illustrating growth of neurons on a coverslip coated with parylene C and recombinant human L1 produced in HEK293 cells.

This example illustrates that L1 orthologues can support growth of neurons from multiple species. L1 freshly isolated from monkey brain was covalently linked to parylene-C coated coverslips and primary cortical neuron cultures from rat brain were seeded on to the coverslips. The rat neurons successfully attached to the coverslips and produced extensive neurite outgrowth, indicating that the monkey L1 successfully supports growth of rat neurons (FIG. 24).

It will be apparent that the precise details of the methods or compositions described may be varied or modified without departing from the spirit of the described embodiments. We claim all such modifications and variations that fall within the scope and spirit of the claims below.

We claim:

1. A method of recording neural signals in a subject, comprising:
    implanting a neural probe for recording the neural signals into neuronal tissue in the subject, wherein the neural probe comprises:
      a) a body comprising one or more electrodes exposed to the neuronal tissue, wherein the one or more electrodes are coupled to electrical conductors extending along the body which can be electrically coupled to a recording apparatus via one or more electrical leads;
      b) a parylene C insulating layer coating on the body and electrical conductors but not the one or more electrodes; and
      c) an L1 polypeptide coating conjugated to an exterior surface of the parylene C insulating layer and comprising from 0.1 ng/mm² to 10.0 ng/mm² L1 polypeptide; and
    recording the neural signals from the neuronal tissue after the neural probe has been implanted in the neuronal tissue for at least six months.

2. The method of claim 1, comprising recording at least four sortable units of neural signals from at least one of the one or more electrodes after the neural probe has been implanted in the neuronal tissue for at least six months.

3. The method of claim 1, comprising recording the neural signals after the neural probe has been implanted in the neuronal tissue for at least one year.

4. The method of claim 1, wherein recording the neural signals comprises recording at least four sortable neural units from at least one electrode of the one or more electrodes of the neural probe after the neural probe has been implanted in the neuronal tissue for at least one year.

5. The method of claim 1, wherein the L1 polypeptide is a monkey, rat, mouse or human L1 polypeptide.

6. The method of claim 1, wherein the subject is a human.

7. The method of claim 1, wherein the L1 polypeptide coating comprises from about 0.1 ng/mm² to about 2.0 ng/mm² L1 polypeptide or functional fragment thereof.

8. A neural probe for recording neural signals in a subject, comprising:
    a) a body comprising one or more electrodes exposed to neuronal tissue when the probe is implanted in the brain of a subject, wherein the one or more electrodes are coupled to electrical conductors extending along the body which can be electrically coupled to a recording apparatus via one or more electrical leads;
    b) a parylene C insulating layer coating the body and electrical conductors but not the electrodes; and
    c) a L1 polypeptide coating conjugated to an exterior surface of the parylene C insulating layer and comprising from 0.1 ng/mm² to 10.0 ng/mm² L1 polypeptide.

9. The neural probe of claim 8, wherein the L1 polypeptide is a monkey, rat, mouse or human L1 polypeptide.

10. The neural probe of claim 8, wherein the L1 polypeptide coating of the neural probe comprises from about 0.1 ng/mm² to about 2.0 ng/mm² L1 polypeptide or functional fragment thereof.

* * * * *

SEQUENCE LISTING

<160> NUMBER OF SEQ ID NOS: 4

<210> SEQ ID NO 1
<211> LENGTH: 1257
<212> TYPE: PRT
<213> ORGANISM: homo sapiens

<400> SEQUENCE: 1

Met Val Val Ala Leu Arg Tyr Val Trp Pro Leu Leu Leu Cys Ser Pro
1               5                   10                  15

-continued

Cys Leu Leu Ile Gln Ile Pro Glu Glu Tyr Glu Gly His His Val Met
                20                  25                  30

Glu Pro Pro Val Ile Thr Glu Gln Ser Pro Arg Arg Leu Val Val Phe
            35                  40                  45

Pro Thr Asp Asp Ile Ser Leu Lys Cys Glu Ala Ser Gly Lys Pro Glu
50                      55                  60

Val Gln Phe Arg Trp Thr Arg Asp Gly Val His Phe Lys Pro Lys Glu
65                  70                  75                  80

Glu Leu Gly Val Thr Val Tyr Gln Ser Pro His Ser Gly Ser Phe Thr
                85                  90                  95

Ile Thr Gly Asn Asn Ser Asn Phe Ala Gln Arg Phe Gln Gly Ile Tyr
                100                 105                 110

Arg Cys Phe Ala Ser Asn Lys Leu Gly Thr Ala Met Ser His Glu Ile
                115                 120                 125

Arg Leu Met Ala Glu Gly Ala Pro Lys Trp Pro Lys Glu Thr Val Lys
            130                 135                 140

Pro Val Glu Val Glu Glu Gly Glu Ser Val Val Leu Pro Cys Asn Pro
145                 150                 155                 160

Pro Pro Ser Ala Glu Pro Leu Arg Ile Tyr Trp Met Asn Ser Lys Ile
                165                 170                 175

Leu His Ile Lys Gln Asp Glu Arg Val Thr Met Gly Gln Asn Gly Asn
                180                 185                 190

Leu Tyr Phe Ala Asn Val Leu Thr Ser Asp Asn His Ser Asp Tyr Ile
            195                 200                 205

Cys His Ala His Phe Pro Gly Thr Arg Thr Ile Ile Gln Lys Glu Pro
210                 215                 220

Ile Asp Leu Arg Val Lys Ala Thr Asn Ser Met Ile Asp Arg Lys Pro
225                 230                 235                 240

Arg Leu Leu Phe Pro Thr Asn Ser Ser Ser His Leu Val Ala Leu Gln
                245                 250                 255

Gly Gln Pro Leu Val Leu Glu Cys Ile Ala Glu Gly Phe Pro Thr Pro
            260                 265                 270

Thr Ile Lys Trp Leu Arg Pro Ser Gly Pro Met Pro Ala Asp Arg Val
    275                 280                 285

Thr Tyr Gln Asn His Asn Lys Thr Leu Gln Leu Leu Lys Val Gly Glu
    290                 295                 300

Glu Asp Asp Gly Glu Tyr Arg Cys Leu Ala Glu Asn Ser Leu Gly Ser
305                 310                 315                 320

Ala Arg His Ala Tyr Tyr Val Thr Val Glu Ala Pro Tyr Trp Leu
                325                 330                 335

His Lys Pro Gln Ser His Leu Tyr Gly Pro Gly Glu Thr Ala Arg Leu
                340                 345                 350

Asp Cys Gln Val Gln Gly Arg Pro Gln Pro Glu Val Thr Trp Arg Ile
        355                 360                 365

Asn Gly Ile Pro Val Glu Glu Leu Ala Lys Asp Gln Lys Tyr Arg Ile
        370                 375                 380

Gln Arg Gly Ala Leu Ile Leu Ser Asn Val Gln Pro Ser Asp Thr Met
385                 390                 395                 400

Val Thr Gln Cys Glu Ala Arg Asn Arg His Gly Leu Leu Leu Ala Asn
                405                 410                 415

Ala Tyr Ile Tyr Val Val Gln Leu Pro Ala Lys Ile Leu Thr Ala Asp
            420                 425                 430

Asn Gln Thr Tyr Met Ala Val Gln Gly Ser Thr Ala Tyr Leu Leu Cys

```
            435                 440                 445
Lys Ala Phe Gly Ala Pro Val Pro Ser Val Gln Trp Leu Asp Glu Asp
        450                 455                 460
Gly Thr Thr Val Leu Gln Asp Glu Arg Phe Phe Pro Tyr Ala Asn Gly
465                 470                 475                 480
Thr Leu Gly Ile Arg Asp Leu Gln Ala Asn Asp Thr Gly Arg Tyr Phe
                485                 490                 495
Cys Leu Ala Ala Asn Asp Gln Asn Asn Val Thr Ile Met Ala Asn Leu
            500                 505                 510
Lys Val Lys Asp Ala Thr Gln Ile Thr Gln Gly Pro Arg Ser Thr Ile
        515                 520                 525
Glu Lys Lys Gly Ser Arg Val Thr Phe Thr Cys Gln Ala Ser Phe Asp
    530                 535                 540
Pro Ser Leu Gln Pro Ser Ile Thr Trp Arg Gly Asp Gly Arg Asp Leu
545                 550                 555                 560
Gln Glu Leu Gly Asp Ser Asp Lys Tyr Phe Ile Glu Asp Gly Arg Leu
                565                 570                 575
Val Ile His Ser Leu Asp Tyr Ser Asp Gln Gly Asn Tyr Ser Cys Val
            580                 585                 590
Ala Ser Thr Glu Leu Asp Val Val Glu Ser Arg Ala Gln Leu Leu Val
        595                 600                 605
Val Gly Ser Pro Gly Pro Val Pro Arg Leu Val Leu Ser Asp Leu His
    610                 615                 620
Leu Leu Thr Gln Ser Gln Val Arg Val Ser Trp Ser Pro Ala Glu Asp
625                 630                 635                 640
His Asn Ala Pro Ile Glu Lys Tyr Asp Ile Glu Phe Glu Asp Lys Glu
                645                 650                 655
Met Ala Pro Glu Lys Trp Tyr Ser Leu Gly Lys Val Pro Gly Asn Gln
            660                 665                 670
Thr Ser Thr Thr Leu Lys Leu Ser Pro Tyr Val His Tyr Thr Phe Arg
        675                 680                 685
Val Thr Ala Ile Asn Lys Tyr Gly Pro Gly Glu Pro Ser Pro Val Ser
    690                 695                 700
Glu Thr Val Val Thr Pro Glu Ala Ala Pro Glu Lys Asn Pro Val Asp
705                 710                 715                 720
Val Lys Gly Glu Gly Asn Glu Thr Thr Asn Met Val Ile Thr Trp Lys
                725                 730                 735
Pro Leu Arg Trp Met Asp Trp Asn Ala Pro Gln Val Gln Tyr Arg Val
            740                 745                 750
Gln Trp Arg Pro Gln Gly Thr Arg Gly Pro Trp Gln Glu Gln Ile Val
        755                 760                 765
Ser Asp Pro Phe Leu Val Val Ser Asn Thr Ser Thr Phe Val Pro Tyr
    770                 775                 780
Glu Ile Lys Val Gln Ala Val Asn Ser Gln Gly Lys Gly Pro Glu Pro
785                 790                 795                 800
Gln Val Thr Ile Gly Tyr Ser Gly Glu Asp Tyr Pro Gln Ala Ile Pro
                805                 810                 815
Glu Leu Glu Gly Ile Glu Ile Leu Asn Ser Ser Ala Val Leu Val Lys
            820                 825                 830
Trp Arg Pro Val Asp Leu Ala Gln Val Lys Gly His Leu Arg Gly Tyr
        835                 840                 845
Asn Val Thr Tyr Trp Arg Glu Gly Ser Gln Arg Lys His Ser Lys Arg
    850                 855                 860
```

-continued

```
His Ile His Lys Asp His Val Val Pro Ala Asn Thr Thr Ser Val
865                 870             875             880

Ile Leu Ser Gly Leu Arg Pro Tyr Ser Ser Tyr His Leu Glu Val Gln
                885             890                 895

Ala Phe Asn Gly Arg Gly Ser Gly Pro Ala Ser Glu Pro Thr Phe Ser
            900             905                 910

Thr Pro Glu Gly Val Pro Gly His Pro Glu Ala Leu His Leu Glu Cys
        915             920                 925

Gln Ser Asn Thr Ser Leu Leu Leu Arg Trp Gln Pro Pro Leu Ser His
930             935                 940

Asn Gly Val Leu Thr Gly Tyr Val Leu Ser Tyr His Pro Leu Asp Glu
945                 950             955                 960

Gly Gly Lys Gly Gln Leu Ser Phe Asn Leu Arg Asp Pro Glu Leu Arg
                965             970                 975

Thr His Asn Leu Thr Asp Leu Ser Pro His Leu Arg Tyr Arg Phe Gln
            980             985                 990

Leu Gln Ala Thr Thr Lys Glu Gly Pro Gly Glu Ala Ile Val Arg Glu
        995             1000                1005

Gly Gly Thr Met Ala Leu Ser Gly Ile Ser Asp Phe Gly Asn Ile
    1010            1015            1020

Ser Ala Thr Ala Gly Glu Asn Tyr Ser Val Val Ser Trp Val Pro
    1025            1030            1035

Lys Glu Gly Gln Cys Asn Phe Arg Phe His Ile Leu Phe Lys Ala
    1040            1045            1050

Leu Gly Glu Glu Lys Gly Gly Ala Ser Leu Ser Pro Gln Tyr Val
    1055            1060            1065

Ser Tyr Asn Gln Ser Ser Tyr Thr Gln Trp Asp Leu Gln Pro Asp
    1070            1075            1080

Thr Asp Tyr Glu Ile His Leu Phe Lys Glu Arg Met Phe Arg His
    1085            1090            1095

Gln Met Ala Val Lys Thr Asn Gly Thr Gly Arg Val Arg Leu Pro
    1100            1105            1110

Pro Ala Gly Phe Ala Thr Glu Gly Trp Phe Ile Gly Phe Val Ser
    1115            1120            1125

Ala Ile Ile Leu Leu Leu Leu Val Leu Leu Ile Leu Cys Phe Ile
    1130            1135            1140

Lys Arg Ser Lys Gly Gly Lys Tyr Ser Val Lys Asp Lys Glu Asp
    1145            1150            1155

Thr Gln Val Asp Ser Glu Ala Arg Pro Met Lys Asp Glu Thr Phe
    1160            1165            1170

Gly Glu Tyr Arg Ser Leu Glu Ser Asp Asn Glu Glu Lys Ala Phe
    1175            1180            1185

Gly Ser Ser Gln Pro Ser Leu Asn Gly Asp Ile Lys Pro Leu Gly
    1190            1195            1200

Ser Asp Asp Ser Leu Ala Asp Tyr Gly Gly Ser Val Asp Val Gln
    1205            1210            1215

Phe Asn Glu Asp Gly Ser Phe Ile Gly Gln Tyr Ser Gly Lys Lys
    1220            1225            1230

Glu Lys Glu Ala Ala Gly Gly Asn Asp Ser Ser Gly Ala Thr Ser
    1235            1240            1245

Pro Ile Asn Pro Ala Val Ala Leu Glu
    1250            1255
```

<210> SEQ ID NO 2
<211> LENGTH: 858
<212> TYPE: PRT
<213> ORGANISM: homo sapiens

<400> SEQUENCE: 2

```
Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
    290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Ala Ser Trp Thr Arg Pro Glu Lys Gln Glu Thr Leu Asp Gly His
        355                 360                 365

Met Val Val Arg Ser His Ala Arg Val Ser Ser Leu Thr Leu Lys Ser
    370                 375                 380
```

```
Ile Gln Tyr Thr Asp Ala Gly Glu Tyr Ile Cys Thr Ala Ser Asn Thr
385                 390                 395                 400

Ile Gly Gln Asp Ser Gln Ser Met Tyr Leu Glu Val Gln Tyr Ala Pro
            405                 410                 415

Lys Leu Gln Gly Pro Val Ala Val Tyr Thr Trp Glu Gly Asn Gln Val
        420                 425                 430

Asn Ile Thr Cys Glu Val Phe Ala Tyr Pro Ser Ala Thr Ile Ser Trp
            435                 440                 445

Phe Arg Asp Gly Gln Leu Leu Pro Ser Ser Asn Tyr Ser Asn Ile Lys
        450                 455                 460

Ile Tyr Asn Thr Pro Ser Ala Ser Tyr Leu Glu Val Thr Pro Asp Ser
465                 470                 475                 480

Glu Asn Asp Phe Gly Asn Tyr Asn Cys Thr Ala Val Asn Arg Ile Gly
            485                 490                 495

Gln Glu Ser Leu Glu Phe Ile Leu Val Gln Ala Asp Thr Pro Ser Ser
        500                 505                 510

Pro Ser Ile Asp Gln Val Glu Pro Tyr Ser Ser Thr Ala Gln Val Gln
        515                 520                 525

Phe Asp Glu Pro Glu Ala Thr Gly Gly Val Pro Ile Leu Lys Tyr Lys
530                 535                 540

Ala Glu Trp Arg Ala Val Gly Glu Glu Val Trp His Ser Lys Trp Tyr
545                 550                 555                 560

Asp Ala Lys Glu Ala Ser Met Glu Gly Ile Val Thr Ile Val Gly Leu
            565                 570                 575

Lys Pro Glu Thr Thr Tyr Ala Val Arg Leu Ala Ala Leu Asn Gly Lys
        580                 585                 590

Gly Leu Gly Glu Ile Ser Ala Ala Ser Glu Phe Lys Thr Gln Pro Val
        595                 600                 605

Gln Gly Glu Pro Ser Ala Pro Lys Leu Glu Gly Gln Met Gly Glu Asp
    610                 615                 620

Gly Asn Ser Ile Lys Val Asn Leu Ile Lys Gln Asp Asp Gly Gly Ser
625                 630                 635                 640

Pro Ile Arg His Tyr Leu Val Arg Tyr Arg Ala Leu Ser Ser Glu Trp
            645                 650                 655

Lys Pro Glu Ile Arg Leu Pro Ser Gly Ser Asp His Val Met Leu Lys
            660                 665                 670

Ser Leu Asp Trp Asn Ala Glu Tyr Glu Val Tyr Val Val Ala Glu Asn
        675                 680                 685

Gln Gln Gly Lys Ser Lys Ala Ala His Phe Val Phe Arg Thr Ser Ala
    690                 695                 700

Gln Pro Thr Ala Ile Pro Ala Asn Gly Ser Pro Thr Ser Gly Leu Ser
705                 710                 715                 720

Thr Gly Ala Ile Val Gly Ile Leu Ile Val Ile Phe Val Leu Leu Leu
            725                 730                 735

Val Val Val Asp Ile Thr Cys Tyr Phe Leu Asn Lys Cys Gly Leu Phe
            740                 745                 750

Met Cys Ile Ala Val Asn Leu Cys Gly Lys Ala Gly Pro Gly Ala Lys
        755                 760                 765

Gly Lys Asp Met Glu Glu Gly Lys Ala Ala Phe Ser Lys Asp Glu Ser
    770                 775                 780

Lys Glu Pro Ile Val Glu Val Arg Thr Glu Glu Glu Arg Thr Pro Asn
785                 790                 795                 800
```

-continued

His Asp Gly Gly Lys His Thr Glu Pro Asn Glu Thr Thr Pro Leu Thr
          805                 810                 815

Glu Pro Glu Lys Gly Pro Val Glu Ala Lys Pro Glu Cys Gln Glu Thr
          820                 825                 830

Glu Thr Lys Pro Ala Pro Ala Glu Val Lys Thr Val Pro Asn Asp Ala
          835                 840                 845

Thr Gln Thr Lys Glu Asn Glu Asn Lys Ala
          850                 855

<210> SEQ ID NO 3
<211> LENGTH: 1208
<212> TYPE: PRT
<213> ORGANISM: homo sapiens

<400> SEQUENCE: 3

Met Glu Pro Leu Leu Gly Arg Gly Leu Ile Val Tyr Leu Met Phe
1               5                   10                  15

Leu Leu Leu Lys Phe Ser Lys Ala Ile Glu Ile Pro Ser Ser Val Gln
            20                  25                  30

Gln Val Pro Thr Ile Ile Lys Gln Ser Lys Val Gln Val Ala Phe Pro
            35                  40                  45

Phe Asp Glu Tyr Phe Gln Ile Glu Cys Glu Ala Lys Gly Asn Pro Glu
50                  55                  60

Pro Thr Phe Ser Trp Thr Lys Asp Gly Asn Pro Phe Tyr Phe Thr Asp
65                  70                  75                  80

His Arg Ile Ile Pro Ser Asn Asn Ser Gly Thr Phe Arg Ile Pro Asn
                85                  90                  95

Glu Gly His Ile Ser His Phe Gln Gly Lys Tyr Arg Cys Phe Ala Ser
            100                 105                 110

Asn Lys Leu Gly Ile Ala Met Ser Glu Glu Ile Glu Phe Ile Val Pro
            115                 120                 125

Ser Val Pro Lys Phe Pro Lys Glu Lys Ile Asp Pro Leu Glu Val Glu
            130                 135                 140

Glu Gly Asp Pro Ile Val Leu Pro Cys Asn Pro Pro Lys Gly Leu Pro
145                 150                 155                 160

Pro Leu His Ile Tyr Trp Met Asn Ile Glu Leu Glu His Ile Glu Gln
                165                 170                 175

Asp Glu Arg Val Tyr Met Ser Gln Lys Gly Asp Leu Tyr Phe Ala Asn
            180                 185                 190

Val Glu Glu Lys Asp Ser Arg Asn Asp Tyr Cys Cys Phe Ala Ala Phe
            195                 200                 205

Pro Arg Leu Arg Thr Ile Val Gln Lys Met Pro Met Lys Leu Thr Val
210                 215                 220

Asn Ser Ser Asn Ser Ile Lys Gln Arg Lys Pro Lys Leu Leu Leu Pro
225                 230                 235                 240

Pro Thr Glu Ser Gly Ser Glu Ser Ser Ile Thr Ile Leu Lys Gly Glu
                245                 250                 255

Ile Leu Leu Leu Glu Cys Phe Ala Glu Gly Leu Pro Thr Pro Gln Val
            260                 265                 270

Asp Trp Asn Lys Ile Gly Gly Asp Leu Pro Lys Gly Arg Glu Ala Lys
            275                 280                 285

Glu Asn Tyr Gly Lys Thr Leu Lys Ile Glu Asn Val Ser Tyr Gln Asp
            290                 295                 300

Lys Gly Asn Tyr Arg Cys Thr Ala Ser Asn Phe Leu Gly Thr Ala Thr
305                 310                 315                 320

```
His Asp Phe His Val Ile Val Glu Glu Pro Pro Arg Trp Thr Lys Lys
                325                 330                 335
Pro Gln Ser Ala Val Tyr Ser Thr Gly Ser Asn Gly Ile Leu Leu Cys
                340                 345                 350
Glu Ala Glu Gly Glu Pro Gln Pro Thr Ile Lys Trp Arg Val Asn Gly
                355                 360                 365
Ser Pro Val Asp Asn His Pro Phe Ala Gly Asp Val Val Phe Pro Arg
                370                 375                 380
Glu Ile Ser Phe Thr Asn Leu Gln Pro Asn His Thr Ala Val Tyr Gln
385                 390                 395                 400
Cys Glu Ala Ser Asn Val His Gly Thr Ile Leu Ala Asn Ala Asn Ile
                405                 410                 415
Asp Val Val Asp Val Arg Pro Leu Ile Gln Thr Lys Asp Gly Glu Asn
                420                 425                 430
Tyr Ala Thr Val Val Gly Tyr Ser Ala Phe Leu His Cys Glu Phe Phe
                435                 440                 445
Ala Ser Pro Glu Ala Val Val Ser Trp Gln Lys Val Glu Glu Val Lys
                450                 455                 460
Pro Leu Glu Gly Arg Arg Tyr His Ile Tyr Glu Asn Gly Thr Leu Gln
465                 470                 475                 480
Ile Asn Arg Thr Thr Glu Glu Asp Ala Gly Ser Tyr Ser Cys Trp Val
                485                 490                 495
Glu Asn Ala Ile Gly Lys Thr Ala Val Thr Ala Asn Leu Asp Ile Arg
                500                 505                 510
Asn Ala Thr Lys Leu Arg Val Ser Pro Lys Asn Pro Arg Ile Pro Lys
                515                 520                 525
Leu His Met Leu Glu Leu His Cys Glu Ser Lys Cys Asp Ser His Leu
                530                 535                 540
Lys His Ser Leu Lys Leu Ser Trp Ser Lys Asp Gly Glu Ala Phe Glu
545                 550                 555                 560
Ile Asn Gly Thr Glu Asp Gly Arg Ile Ile Asp Gly Ala Asn Leu
                565                 570                 575
Thr Ile Ser Asn Val Thr Leu Glu Asp Gln Gly Ile Tyr Cys Cys Ser
                580                 585                 590
Ala His Thr Ala Leu Asp Ser Ala Ala Asp Ile Thr Gln Val Thr Val
                595                 600                 605
Leu Asp Val Pro Asp Pro Pro Glu Asn Leu His Leu Ser Glu Arg Gln
610                 615                 620
Asn Arg Ser Val Arg Leu Thr Trp Glu Ala Gly Ala Asp His Asn Ser
625                 630                 635                 640
Asn Ile Ser Glu Tyr Ile Val Glu Phe Glu Gly Asn Lys Glu Glu Pro
                645                 650                 655
Gly Arg Trp Glu Glu Leu Thr Arg Val Gln Gly Lys Lys Thr Thr Val
                660                 665                 670
Ile Leu Pro Leu Ala Pro Phe Val Arg Tyr Gln Phe Arg Val Ile Ala
                675                 680                 685
Val Asn Glu Val Gly Arg Ser Gln Pro Ser Gln Pro Ser Asp His His
                690                 695                 700
Glu Thr Pro Pro Ala Ala Pro Asp Arg Asn Pro Gln Asn Ile Arg Val
705                 710                 715                 720
Gln Ala Ser Gln Pro Lys Glu Met Ile Ile Lys Trp Glu Pro Leu Lys
                725                 730                 735
```

-continued

Ser Met Glu Gln Asn Gly Pro Gly Leu Glu Tyr Arg Val Thr Trp Lys
            740                 745                 750

Pro Gln Gly Ala Pro Val Glu Trp Glu Glu Thr Val Thr Asn His
        755                 760                 765

Thr Leu Arg Val Met Thr Pro Ala Val Tyr Ala Pro Tyr Asp Val Lys
    770                 775                 780

Val Gln Ala Ile Asn Gln Leu Gly Ser Gly Pro Asp Pro Gln Ser Val
785                 790                 795                 800

Thr Leu Tyr Ser Gly Asp Tyr Pro Asp Thr Ala Pro Val Ile His
                805                 810                 815

Gly Val Asp Val Ile Asn Ser Thr Leu Val Lys Val Thr Trp Ser Thr
            820                 825                 830

Val Pro Lys Asp Arg Val His Gly Arg Leu Lys Gly Tyr Gln Ile Asn
        835                 840                 845

Trp Trp Lys Thr Lys Ser Leu Leu Asp Gly Arg Thr His Pro Lys Glu
    850                 855                 860

Val Asn Ile Leu Arg Phe Ser Gly Gln Arg Asn Ser Gly Met Val Pro
865                 870                 875                 880

Ser Leu Asp Ala Phe Ser Glu Phe His Leu Thr Val Leu Ala Tyr Asn
                885                 890                 895

Ser Lys Gly Ala Gly Pro Glu Ser Glu Pro Tyr Ile Phe Gln Thr Pro
            900                 905                 910

Glu Gly Val Pro Glu Gln Pro Thr Phe Leu Lys Val Ile Lys Val Asp
        915                 920                 925

Lys Asp Thr Ala Thr Leu Ser Trp Gly Leu Pro Lys Lys Leu Asn Gly
    930                 935                 940

Asn Leu Thr Gly Tyr Leu Leu Gln Tyr Gln Ile Ile Asn Asp Thr Tyr
945                 950                 955                 960

Glu Ile Gly Glu Leu Asn Asp Ile Asn Ile Thr Thr Pro Ser Lys Pro
                965                 970                 975

Ser Trp His Leu Ser Asn Leu Asn Ala Thr Thr Lys Tyr Lys Phe Tyr
            980                 985                 990

Leu Arg Ala Cys Thr Ser Gln Gly Cys Gly Lys Pro Ile Thr Glu Glu
        995                 1000                1005

Ser Ser Thr Leu Gly Glu Gly Ser Lys Gly Ile Gly Lys Ile Ser
    1010                1015                1020

Gly Val Asn Leu Thr Gln Lys Thr His Pro Val Glu Val Phe Glu
    1025                1030                1035

Pro Gly Ala Glu His Ile Val Arg Leu Met Thr Lys Asn Trp Gly
    1040                1045                1050

Asp Asn Asp Ser Ile Phe Gln Asp Val Ile Glu Thr Arg Gly Arg
    1055                1060                1065

Glu Tyr Ala Gly Leu Tyr Asp Asp Ile Ser Thr Gln Gly Trp Phe
    1070                1075                1080

Ile Gly Leu Met Cys Ala Ile Ala Leu Leu Thr Leu Leu Leu Leu
    1085                1090                1095

Thr Val Cys Phe Val Lys Arg Asn Arg Gly Gly Lys Tyr Ser Val
    1100                1105                1110

Lys Glu Lys Glu Asp Leu His Pro Asp Pro Glu Ile Gln Ser Val
    1115                1120                1125

Lys Asp Glu Thr Phe Gly Glu Tyr Ser Asp Ser Asp Glu Lys Pro
    1130                1135                1140

Leu Lys Gly Ser Leu Arg Ser Leu Asn Arg Asp Met Gln Pro Thr

```
                    1145               1150                1155

Glu  Ser  Ala  Asp  Ser  Leu  Val  Glu  Tyr  Gly  Gly  Asp  His  Gly
          1160                    1165                1170

Leu  Phe  Ser  Glu  Asp  Gly  Ser  Phe  Ile  Gly  Ala  Tyr  Ala  Gly  Ser
     1175                    1180                1185

Lys  Glu  Lys  Gly  Ser  Val  Glu  Ser  Asn  Gly  Ser  Ser  Thr  Ala  Thr
     1190                    1195                1200

Phe  Pro  Leu  Arg  Ala
     1205

<210> SEQ ID NO 4
<211> LENGTH: 1347
<212> TYPE: PRT
<213> ORGANISM: homo sapiens

<400> SEQUENCE: 4

Met  Ala  Arg  Gln  Pro  Pro  Pro  Trp  Val  His  Ala  Ala  Phe  Leu  Leu
1                   5                   10                  15

Cys  Leu  Leu  Ser  Leu  Gly  Gly  Ala  Ile  Glu  Ile  Pro  Met  Asp  Pro
                20                  25                  30

Ile  Gln  Asn  Glu  Leu  Thr  Gln  Pro  Pro  Thr  Ile  Thr  Lys  Gln  Ser  Ala
            35                  40                  45

Lys  Asp  His  Ile  Val  Asp  Pro  Arg  Asp  Asn  Ile  Leu  Ile  Glu  Cys  Glu
50                  55                      60

Ala  Lys  Gly  Asn  Pro  Ala  Pro  Ser  Phe  His  Trp  Thr  Arg  Asn  Ser  Arg
65                  70                  75                  80

Phe  Phe  Asn  Ile  Ala  Lys  Asp  Pro  Arg  Val  Ser  Met  Arg  Arg  Ser
                85                  90                  95

Gly  Thr  Leu  Val  Ile  Asp  Phe  Arg  Ser  Gly  Gly  Arg  Pro  Glu  Glu  Tyr
            100                 105                 110

Glu  Gly  Glu  Tyr  Gln  Cys  Phe  Ala  Arg  Asn  Lys  Phe  Gly  Thr  Ala  Leu
        115                 120                 125

Ser  Asn  Arg  Ile  Arg  Leu  Gln  Val  Ser  Lys  Ser  Pro  Leu  Trp  Pro  Lys
    130                 135                 140

Glu  Asn  Leu  Asp  Pro  Val  Val  Gln  Glu  Gly  Ala  Pro  Leu  Thr  Leu
145                 150                 155                 160

Gln  Cys  Asn  Pro  Pro  Gly  Leu  Pro  Ser  Pro  Val  Ile  Phe  Trp  Met
                165                 170                 175

Ser  Ser  Ser  Met  Glu  Pro  Ile  Thr  Gln  Asp  Lys  Arg  Val  Ser  Gln  Gly
            180                 185                 190

His  Asn  Gly  Asp  Leu  Tyr  Phe  Ser  Asn  Val  Met  Leu  Gln  Asp  Met  Gln
        195                 200                 205

Thr  Asp  Tyr  Ser  Cys  Asn  Ala  Arg  Phe  His  Thr  His  Thr  Ile  Gln
    210                 215                 220

Gln  Lys  Asn  Pro  Phe  Thr  Leu  Lys  Val  Leu  Thr  Thr  Arg  Gly  Val  Ala
225                 230                 235                 240

Glu  Arg  Thr  Pro  Ser  Phe  Met  Tyr  Pro  Gln  Gly  Thr  Ala  Ser  Ser  Gln
                245                 250                 255

Met  Val  Leu  Arg  Gly  Met  Asp  Leu  Leu  Leu  Glu  Cys  Ile  Ala  Ser  Gly
            260                 265                 270

Val  Pro  Thr  Pro  Asp  Ile  Ala  Trp  Tyr  Lys  Lys  Gly  Gly  Asp  Leu  Pro
        275                 280                 285

Ser  Asp  Lys  Ala  Lys  Phe  Glu  Asn  Phe  Asn  Lys  Ala  Leu  Arg  Ile  Thr
    290                 295                 300
```

-continued

Asn Val Ser Glu Glu Asp Ser Gly Glu Tyr Phe Cys Leu Ala Ser Asn
305                 310                 315                 320

Lys Met Gly Ser Ile Arg His Thr Ile Ser Val Arg Val Lys Ala Ala
            325                 330                 335

Pro Tyr Trp Leu Asp Glu Pro Lys Asn Leu Ile Leu Ala Pro Gly Glu
        340                 345                 350

Asp Gly Arg Leu Val Cys Arg Ala Asn Gly Asn Pro Lys Pro Thr Val
    355                 360                 365

Gln Trp Met Val Asn Gly Glu Pro Leu Gln Ser Ala Pro Pro Asn Pro
370                 375                 380

Asn Arg Glu Val Ala Gly Asp Thr Ile Ile Phe Arg Asp Thr Gln Ile
385                 390                 395                 400

Ser Ser Arg Ala Val Tyr Gln Cys Asn Thr Ser Asn Glu His Gly Tyr
                405                 410                 415

Leu Leu Ala Asn Ala Phe Val Ser Val Leu Asp Val Pro Pro Arg Met
            420                 425                 430

Leu Ser Pro Arg Asn Gln Leu Ile Arg Val Ile Leu Tyr Asn Arg Thr
        435                 440                 445

Arg Leu Asp Cys Pro Phe Phe Gly Ser Pro Ile Pro Thr Leu Arg Trp
    450                 455                 460

Phe Lys Asn Gly Gln Gly Ser Asn Leu Asp Gly Gly Asn Tyr His Val
465                 470                 475                 480

Tyr Glu Asn Gly Ser Leu Glu Ile Lys Met Ile Arg Lys Glu Asp Gln
                485                 490                 495

Gly Ile Tyr Thr Cys Val Ala Thr Asn Ile Leu Gly Lys Ala Glu Asn
            500                 505                 510

Gln Val Arg Leu Glu Val Lys Asp Pro Thr Arg Ile Tyr Arg Met Pro
        515                 520                 525

Glu Asp Gln Val Ala Arg Arg Gly Thr Thr Val Gln Leu Glu Cys Arg
    530                 535                 540

Val Lys His Asp Pro Ser Leu Lys Leu Thr Val Ser Trp Leu Lys Asp
545                 550                 555                 560

Asp Glu Pro Leu Tyr Ile Gly Asn Arg Met Lys Lys Glu Asp Asp Ser
                565                 570                 575

Leu Thr Ile Phe Gly Val Ala Glu Arg Asp Gln Gly Ser Tyr Thr Cys
            580                 585                 590

Val Ala Ser Thr Glu Leu Asp Gln Asp Leu Ala Lys Ala Tyr Leu Thr
        595                 600                 605

Val Leu Ala Asp Gln Ala Thr Pro Thr Asn Arg Leu Ala Ala Leu Pro
    610                 615                 620

Lys Gly Arg Pro Asp Arg Pro Arg Asp Leu Glu Leu Thr Asp Leu Ala
625                 630                 635                 640

Glu Arg Ser Val Arg Leu Thr Trp Ile Pro Gly Asp Ala Asn Asn Ser
                645                 650                 655

Pro Ile Thr Asp Tyr Val Val Gln Phe Glu Glu Asp Gln Phe Gln Pro
            660                 665                 670

Gly Val Trp His Asp His Ser Lys Tyr Pro Gly Ser Val Asn Ser Ala
        675                 680                 685

Val Leu Arg Leu Ser Pro Tyr Val Asn Tyr Gln Phe Arg Val Ile Ala
    690                 695                 700

Ile Asn Glu Val Gly Ser Ser His Pro Ser Leu Pro Ser Glu Arg Tyr
705                 710                 715                 720

Arg Thr Ser Gly Ala Pro Pro Glu Ser Asn Pro Gly Asp Val Lys Gly

-continued

```
                725                 730                 735
Glu Gly Thr Arg Lys Asn Asn Met Glu Ile Thr Trp Thr Pro Met Asn
                740                 745                 750
Ala Thr Ser Ala Phe Gly Pro Asn Leu Arg Tyr Ile Val Lys Trp Arg
                755                 760                 765
Arg Arg Glu Thr Arg Glu Ala Trp Asn Asn Val Thr Val Trp Gly Ser
        770                 775                 780
Arg Tyr Val Val Gly Gln Thr Pro Val Tyr Val Pro Tyr Glu Ile Arg
785                 790                 795                 800
Val Gln Ala Glu Asn Asp Phe Gly Lys Gly Pro Glu Pro Ser Val
                805                 810                 815
Ile Gly Tyr Ser Gly Glu Asp Tyr Pro Arg Ala Ala Pro Thr Glu Val
                820                 825                 830
Lys Val Arg Val Met Asn Ser Thr Ala Ile Ser Leu Gln Trp Asn Arg
                835                 840                 845
Val Tyr Ser Asp Thr Val Gln Gly Gln Leu Arg Glu Tyr Arg Ala Tyr
850                 855                 860
Tyr Trp Arg Glu Ser Ser Leu Leu Lys Asn Leu Trp Val Ser Gln Lys
865                 870                 875                 880
Arg Gln Gln Ala Ser Phe Pro Gly Asp Arg Leu Arg Gly Val Val Ser
                885                 890                 895
Arg Leu Phe Pro Tyr Ser Asn Tyr Lys Leu Glu Met Val Val Asn
                900                 905                 910
Gly Arg Gly Asp Gly Pro Arg Ser Glu Thr Lys Glu Phe Thr Thr Pro
        915                 920                 925
Glu Gly Val Pro Ser Ala Pro Arg Arg Phe Arg Val Arg Gln Pro Asn
930                 935                 940
Leu Glu Thr Ile Asn Leu Glu Trp Asp His Pro Glu His Pro Asn Gly
945                 950                 955                 960
Ile Met Ile Gly Tyr Thr Leu Lys Tyr Val Ala Phe Asn Gly Thr Lys
                965                 970                 975
Val Gly Lys Gln Ile Val Glu Asn Phe Ser Pro Asn Gln Thr Lys Phe
        980                 985                 990
Thr Val Gln Arg Thr Asp Pro Val Ser Arg Tyr Arg Phe Thr Leu Ser
        995                 1000                1005
Ala Arg Thr Gln Val Gly Ser Gly Glu Ala Val Thr Glu Glu Ser
        1010                1015                1020
Pro Ala Pro Pro Asn Glu Ala Thr Pro Thr Ala Ala Pro Pro Thr
        1025                1030                1035
Leu Pro Pro Thr Thr Val Gly Ala Thr Gly Ala Val Ser Ser Thr
        1040                1045                1050
Asp Ala Thr Ala Ile Ala Ala Thr Thr Glu Ala Thr Thr Val Pro
        1055                1060                1065
Ile Ile Pro Thr Val Ala Pro Thr Thr Ile Ala Thr Thr Thr Thr
        1070                1075                1080
Val Ala Thr Thr Thr Thr Thr Ala Ala Ala Thr Thr Thr Thr
        1085                1090                1095
Glu Ser Pro Pro Thr Thr Thr Ser Gly Thr Lys Ile His Glu Ser
        1100                1105                1110
Ala Pro Asp Glu Gln Ser Ile Trp Asn Val Thr Val Leu Pro Asn
        1115                1120                1125
Ser Lys Trp Ala Asn Ile Thr Trp Lys His Asn Phe Gly Pro Gly
        1130                1135                1140
```

```
Thr Asp Phe Val Val Glu Tyr Ile Asp Ser Asn His Thr Lys Lys
    1145            1150            1155

Thr Val Pro Val Lys Ala Gln Ala Gln Pro Ile Gln Leu Thr Asp
    1160            1165            1170

Leu Tyr Pro Gly Met Thr Tyr Thr Leu Arg Val Tyr Ser Arg Asp
    1175            1180            1185

Asn Glu Gly Ile Ser Ser Thr Val Ile Thr Phe Met Thr Ser Thr
    1190            1195            1200

Ala Tyr Thr Asn Asn Gln Ala Asp Ile Ala Thr Gln Gly Trp Phe
    1205            1210            1215

Ile Gly Leu Met Cys Ala Ile Ala Leu Leu Val Leu Ile Leu Leu
    1220            1225            1230

Ile Val Cys Phe Ile Lys Arg Ser Arg Gly Gly Lys Tyr Pro Val
    1235            1240            1245

Arg Glu Lys Lys Asp Val Pro Leu Gly Pro Glu Asp Pro Lys Glu
    1250            1255            1260

Glu Asp Gly Ser Phe Asp Tyr Ser Asp Glu Asp Asn Lys Pro Leu
    1265            1270            1275

Gln Gly Ser Gln Thr Ser Leu Asp Gly Thr Ile Lys Gln Gln Glu
    1280            1285            1290

Ser Asp Asp Ser Leu Val Asp Tyr Gly Glu Gly Gly Glu Gly Gln
    1295            1300            1305

Phe Asn Glu Asp Gly Ser Phe Ile Gly Gln Tyr Thr Val Lys Lys
    1310            1315            1320

Asp Lys Glu Glu Thr Glu Gly Asn Glu Ser Ser Glu Ala Thr Ser
    1325            1330            1335

Pro Val Asn Ala Ile Tyr Ser Leu Ala
    1340            1345
```